(12) United States Patent
Chen et al.

(10) Patent No.: US 10,745,716 B2
(45) Date of Patent: *Aug. 18, 2020

(54) CRISPR-BASED GENOME MODIFICATION AND REGULATION

(71) Applicant: SIGMA-ALDRICH CO. LLC, St. Louis, MO (US)

(72) Inventors: Fuqiang Chen, St. Louis, MO (US); Gregory D. Davis, St. Louis, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/188,924

(22) Filed: Jun. 21, 2016

(65) Prior Publication Data

US 2016/0298135 A1  Oct. 13, 2016

Related U.S. Application Data

(63) Continuation of application No. 14/649,777, filed as application No. PCT/US2013/073307 on Dec. 5, 2013, now abandoned.

(60) Provisional application No. 61/734,256, filed on Dec. 6, 2012, provisional application No. 61/758,624, filed on Jan. 30, 2013, provisional application No. 61/761,046, filed on Feb. 5, 2013, provisional application No. 61/794,422, filed on Mar. 15, 2013.

(51) Int. Cl.

| | |
|---|---|
| *C12N 15/90* | (2006.01) |
| *C12N 9/22* | (2006.01) |
| *C12N 15/63* | (2006.01) |
| *C12N 15/85* | (2006.01) |
| *C12N 15/11* | (2006.01) |
| *C12N 15/67* | (2006.01) |
| *C12N 15/10* | (2006.01) |
| *C07K 7/06* | (2006.01) |
| *C12N 7/00* | (2006.01) |
| *C12N 15/86* | (2006.01) |
| *C07K 14/46* | (2006.01) |
| *C12N 9/96* | (2006.01) |
| *A61K 38/00* | (2006.01) |

(52) U.S. Cl.
CPC .............. *C12N 15/907* (2013.01); *C07K 7/06* (2013.01); *C07K 14/463* (2013.01); *C12N 7/00* (2013.01); *C12N 9/22* (2013.01); *C12N 9/96* (2013.01); *C12N 15/102* (2013.01); *C12N 15/11* (2013.01); *C12N 15/63* (2013.01); *C12N 15/67* (2013.01); *C12N 15/85* (2013.01); *C12N 15/86* (2013.01); *C12Y 301/00* (2013.01); *C12Y 301/21004* (2013.01); *A61K 38/00* (2013.01); *C07K 2319/09* (2013.01); *C07K 2319/10* (2013.01); *C07K 2319/81* (2013.01); *C12N 2310/20* (2017.05); *C12N 2310/3513* (2013.01); *C12N 2750/14143* (2013.01); *C12N 2800/22* (2013.01); *C12N 2800/80* (2013.01)

(58) Field of Classification Search
CPC ..................... C12N 15/90–907; C12N 2310/20
See application file for complete search history.

(56) References Cited

U.S. PATENT DOCUMENTS

| | | | |
|---|---|---|---|
| 4,952,496 A | 8/1990 | Studier et al. | |
| 5,766,900 A | 6/1998 | Shillito et al. | |
| 5,767,367 A | 6/1998 | Dudits et al. | |
| 7,534,819 B2 | 5/2009 | Albarran et al. | |
| 7,691,995 B2 | 4/2010 | Zamore et al. | |
| 7,745,609 B2 | 6/2010 | Bennett et al. | |
| 7,947,874 B2 * | 5/2011 | Rozwadowski | A01H 1/02 435/455 |
| 8,546,553 B2 | 10/2013 | Terns et al. | |
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |

(Continued)

FOREIGN PATENT DOCUMENTS

| | | |
|---|---|---|
| CN | 103224947 A | 7/2013 |
| CN | 103233028 A | 8/2013 |

(Continued)

OTHER PUBLICATIONS

Romani et al. Cellular magnesium homeostasis. Archives of Biochemistry and Biophysics, vol. 512, No. 1, pp. 1-23, Aug. 2011.*
Milo et al. "What are the concentrations of different ions in cells?" http://book.bionumbers.org/what-are-the-concentrati"ns-of-different-ions-in-cells, printed as pp. 1/5-5/5 on Dec. 20, 2016 from the online version of Cell Biology by the numbers, published Dec. 7, 2015.*
Ramakrishna et al. Gene disruption by cell-penetrating peptide-mediated delivery of Cas9 protein and guide RNA. Genome Research, vol. 24, pp. 1020-1027, 2014.*

(Continued)

*Primary Examiner* — Jennifer Dunston
(74) *Attorney, Agent, or Firm* — Benjamin J. Sodey; Sigma-Aldrich Co. LLC

(57) ABSTRACT

The present invention provides RNA-guided endonucleases, which are engineered for expression in eukaryotic cells or embryos, and methods of using the RNA-guided endonuclease for targeted genome modification in eukaryotic cells or embryos. Also provided are fusion proteins, wherein each fusion protein comprises a CRISPR/Cas-like protein or fragment thereof and an effector domain. The effector domain can be a cleavage domain, an epigenetic modification domain, a transcriptional activation domain, or a transcriptional repressor domain. Also provided are methods for using the fusion proteins to modify a chromosomal sequence or regulate expression of a chromosomal sequence.

22 Claims, 7 Drawing Sheets

Specification includes a Sequence Listing.

(56) References Cited

U.S. PATENT DOCUMENTS

| | | |
|---|---|---|
| 8,895,308 B1 | 11/2014 | Zhang et al. |
| 8,906,616 B2 | 12/2014 | Zhang et al. |
| 8,921,332 B2 | 12/2014 | Choulika et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,023,649 B2 | 5/2015 | Mali et al. |
| 9,200,266 B2 | 12/2015 | Wang |
| 9,260,723 B2 | 2/2016 | Mali et al. |
| 10,266,850 B2 * | 4/2019 | Doudna ............... C12N 15/102 |
| 2002/0119570 A1 | 8/2002 | Yoon et al. |
| 2002/0182673 A1 | 12/2002 | Chen et al. |
| 2003/0186238 A1 | 10/2003 | Allawi et al. |
| 2003/0232410 A1 | 12/2003 | Liljedahl et al. |
| 2004/0111221 A1 | 6/2004 | Beattie et al. |
| 2005/0026157 A1 | 2/2005 | Baltimore et al. |
| 2005/0208489 A1 | 9/2005 | Carroll et al. |
| 2005/0220796 A1 * | 10/2005 | Dynan ................... C07K 16/40 |
| | | 424/155.1 |
| 2006/0199190 A1 | 9/2006 | Russell et al. |
| 2006/0234247 A1 | 10/2006 | Puttaraju et al. |
| 2006/0253913 A1 | 11/2006 | Huang et al. |
| 2007/0016012 A1 | 1/2007 | Hartlep et al. |
| 2007/0134796 A1 | 6/2007 | Holmes et al. |
| 2007/0141557 A1 * | 6/2007 | Raab ..................... G06F 19/18 |
| | | 435/5 |
| 2007/0218528 A1 | 9/2007 | Miller |
| 2008/0124725 A1 | 5/2008 | Barrangou et al. |
| 2008/0159996 A1 | 7/2008 | Ando et al. |
| 2009/0227029 A1 | 9/2009 | Radman et al. |
| 2010/0034924 A1 | 2/2010 | Fremaux et al. |
| 2010/0047805 A1 | 2/2010 | Wang |
| 2010/0055728 A1 | 3/2010 | Yang et al. |
| 2010/0055793 A1 * | 3/2010 | Chandrasegaran .. A61K 48/005 |
| | | 435/441 |
| 2010/0055798 A1 | 3/2010 | Battersby |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2011/0002889 A1 | 1/2011 | Barrangou et al. |
| 2011/0082093 A1 | 4/2011 | Gregory et al. |
| 2011/0145940 A1 | 6/2011 | Voytas et al. |
| 2011/0182867 A1 | 7/2011 | Orkin et al. |
| 2011/0189776 A1 | 8/2011 | Terns et al. |
| 2011/0201773 A1 | 8/2011 | Bonzi et al. |
| 2011/0207221 A1 | 8/2011 | Cost et al. |
| 2011/0217739 A1 | 9/2011 | Terns et al. |
| 2011/0223638 A1 | 9/2011 | Wiedenheft et al. |
| 2011/0236530 A1 | 9/2011 | Manoury et al. |
| 2011/0257377 A1 * | 10/2011 | Barnett ................. A61K 39/21 |
| | | 530/405 |
| 2011/0287545 A1 | 11/2011 | Cost et al. |
| 2011/0294114 A1 | 12/2011 | Van Der Loo et al. |
| 2011/0300538 A1 | 12/2011 | Barrangou et al. |
| 2011/0301073 A1 | 12/2011 | Gregory et al. |
| 2012/0029891 A1 | 2/2012 | Behlke et al. |
| 2012/0148590 A1 * | 6/2012 | Bonny ................. C07K 14/4743 |
| | | 424/139.1 |
| 2012/0192298 A1 | 7/2012 | Weinstein et al. |
| 2013/0011828 A1 | 1/2013 | Barrangou et al. |
| 2013/0130248 A1 | 5/2013 | Haurwitz et al. |
| 2013/0158245 A1 | 6/2013 | Russell et al. |
| 2013/0196373 A1 | 8/2013 | Gregory et al. |
| 2013/0253040 A1 | 9/2013 | Miller et al. |
| 2013/0288251 A1 | 10/2013 | Horvath et al. |
| 2013/0309670 A1 | 11/2013 | Frendewey et al. |
| 2013/0326645 A1 | 12/2013 | Cost et al. |
| 2013/0326725 A1 | 12/2013 | Shukla et al. |
| 2013/0330778 A1 | 12/2013 | Zeiner et al. |
| 2013/0345400 A1 * | 12/2013 | Eloit ..................... C07K 14/005 |
| | | 530/350 |
| 2014/0017212 A1 | 1/2014 | Rebar |
| 2014/0017214 A1 | 1/2014 | Cost |
| 2014/0045176 A1 | 2/2014 | Kim et al. |
| 2014/0068797 A1 | 3/2014 | Doudna et al. |
| 2014/0080216 A1 | 3/2014 | Cost et al. |
| 2014/0090112 A1 | 3/2014 | Cogan et al. |
| 2014/0090113 A1 | 3/2014 | Cogan et al. |
| 2014/0090116 A1 | 3/2014 | Ainley et al. |
| 2014/0112896 A1 | 4/2014 | Rebar |
| 2014/0123330 A1 | 5/2014 | Carlson et al. |
| 2014/0127752 A1 | 5/2014 | Zhou et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0235933 A1 | 8/2014 | Lee et al. |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273231 A1 | 9/2014 | Zhang et al. |
| 2014/0273232 A1 | 9/2014 | Zhang et al. |
| 2014/0273233 A1 | 9/2014 | Chen et al. |
| 2014/0273234 A1 | 9/2014 | Zhang et al. |
| 2014/0273235 A1 | 9/2014 | Voytas et al. |
| 2014/0287938 A1 | 9/2014 | Zhang et al. |
| 2014/0294773 A1 | 10/2014 | Brouns et al. |
| 2014/0295556 A1 | 10/2014 | Joung et al. |
| 2014/0295557 A1 | 10/2014 | Joung et al. |
| 2014/0298547 A1 | 10/2014 | Sastry-Dent et al. |
| 2014/0304853 A1 | 10/2014 | Ainley et al. |
| 2014/0309487 A1 | 10/2014 | Lee et al. |
| 2014/0310828 A1 | 10/2014 | Lee et al. |
| 2014/0310830 A1 | 10/2014 | Zhang et al. |
| 2014/0315985 A1 | 10/2014 | May et al. |
| 2014/0335063 A1 | 11/2014 | Cannon et al. |
| 2014/0335620 A1 | 11/2014 | Zhang et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349405 A1 | 11/2014 | Sontheimer et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0357530 A1 | 12/2014 | Zhang et al. |
| 2014/0364333 A1 | 12/2014 | Wu et al. |
| 2014/0377868 A1 | 12/2014 | Joung et al. |
| 2015/0020223 A1 | 1/2015 | Zhang et al. |
| 2015/0024499 A1 | 1/2015 | Brouns et al. |
| 2015/0031089 A1 | 1/2015 | Lindstrom |
| 2015/0031134 A1 | 1/2015 | Zhang et al. |
| 2015/0045546 A1 | 2/2015 | Siksnys et al. |
| 2015/0050699 A1 | 2/2015 | Siksnys et al. |
| 2015/0071889 A1 | 3/2015 | Musunuru et al. |
| 2015/0079681 A1 | 3/2015 | Zhang |
| 2015/0128300 A1 | 5/2015 | Warming et al. |
| 2015/0128307 A1 | 5/2015 | Sastry-Dent et al. |
| 2015/0128308 A1 | 5/2015 | Sastry-Dent et al. |
| 2015/0128309 A1 | 5/2015 | Sastry-Dent et al. |
| 2015/0159174 A1 | 6/2015 | Frendewey et al. |
| 2015/0159175 A1 | 6/2015 | Frendewey et al. |
| 2015/0167000 A1 | 6/2015 | Voytas et al. |
| 2015/0184139 A1 | 7/2015 | Zhang et al. |
| 2015/0203872 A1 | 7/2015 | Zhang |
| 2015/0211058 A1 | 7/2015 | Carstens |
| 2015/0225734 A1 | 8/2015 | Voytas et al. |
| 2015/0225801 A1 | 8/2015 | Cai et al. |
| 2015/0232833 A1 | 8/2015 | Mali et al. |
| 2015/0232881 A1 | 8/2015 | Glucksmann et al. |

(56) References Cited

U.S. PATENT DOCUMENTS

| | | | |
|---|---|---|---|
| 2015/0232882 A1 | 8/2015 | Zhang et al. |
| 2015/0240261 A1 | 8/2015 | Siksnys et al. |
| 2015/0240263 A1 | 8/2015 | Holmes et al. |
| 2015/0247150 A1 | 9/2015 | Zhang et al. |
| 2015/0259684 A1 | 9/2015 | Church et al. |
| 2015/0259704 A1 | 9/2015 | Church et al. |
| 2015/0267176 A1 | 9/2015 | Joung et al. |
| 2015/0267205 A1 | 9/2015 | Froelich et al. |
| 2015/0283265 A1 | 10/2015 | Peyman |
| 2015/0284727 A1 | 10/2015 | Kim et al. |
| 2015/0291961 A1 | 10/2015 | Siksnys et al. |
| 2015/0291965 A1 | 10/2015 | Zhang et al. |
| 2015/0291966 A1 | 10/2015 | Zhang et al. |
| 2015/0291969 A1 | 10/2015 | Nair et al. |
| 2015/0322457 A1* | 11/2015 | Kim ............... C12N 9/16 435/462 |
| 2015/0344912 A1* | 12/2015 | Kim ............... C12N 9/16 435/462 |
| 2016/0002670 A1 | 1/2016 | Church et al. |
| 2016/0017366 A1 | 1/2016 | Chen et al. |
| 2016/0130609 A1* | 5/2016 | Doudna ............... C12N 15/102 435/462 |
| 2016/0138008 A1* | 5/2016 | Doudna ............... C12N 15/102 435/91.51 |
| 2016/0298125 A1 | 10/2016 | Chen et al. |
| 2016/0298132 A1 | 10/2016 | Chen et al. |
| 2016/0298133 A1 | 10/2016 | Chen et al. |
| 2016/0298134 A1 | 10/2016 | Chen et al. |
| 2016/0298136 A1 | 10/2016 | Chen et al. |
| 2016/0298137 A1 | 10/2016 | Chen et al. |
| 2016/0298138 A1 | 10/2016 | Chen et al. |
| 2017/0051310 A1 | 2/2017 | Doudna et al. |
| 2017/0073705 A1 | 3/2017 | Chen et al. |
| 2017/0191082 A1 | 7/2017 | Chen et al. |
| 2018/0135073 A1 | 5/2018 | Chen et al. |
| 2018/0230495 A1* | 8/2018 | Doudna ............... C12N 15/102 |
| 2018/0230496 A1* | 8/2018 | Doudna ............... C12N 15/102 |
| 2018/0230497 A1* | 8/2018 | Doudna ............... C12N 15/102 |
| 2018/0251793 A1* | 9/2018 | Doudna ............... C12N 15/102 |
| 2018/0251794 A1* | 9/2018 | Doudna ............... C12N 15/102 |
| 2018/0251795 A1* | 9/2018 | Charpentier ............... C12N 15/102 |
| 2019/0002921 A1* | 1/2019 | Doudna ............... C12N 15/102 |
| 2019/0002922 A1* | 1/2019 | Doudna ............... C12N 15/102 |
| 2019/0002923 A1* | 1/2019 | Doudna ............... C12N 15/102 |
| 2019/0010520 A1* | 1/2019 | Doudna ............... C12N 15/102 |
| 2019/0169645 A1* | 6/2019 | Doudna ............... C12N 15/102 |
| 2019/0169646 A1* | 6/2019 | Doudna ............... C12N 15/102 |
| 2019/0169647 A1* | 6/2019 | Doudna ............... C12N 15/102 |
| 2019/0169648 A1* | 6/2019 | Doudna ............... C12N 15/102 |

FOREIGN PATENT DOCUMENTS

| | | | | |
|---|---|---|---|---|
| CN | 103343120 A | | 10/2013 | |
| CN | 103388006 A | | 11/2013 | |
| EP | 2 341 149 A1 | | 7/2011 | |
| EP | 2 489 275 A1 | | 8/2012 | |
| EP | 2 674 501 A1 | | 12/2013 | |
| EP | 2 784 162 A1 | | 10/2014 | |
| WO | 88/08450 A1 | | 11/1988 | |
| WO | 02/34771 A2 | | 5/2002 | |
| WO | WO-03087341 A2 * | | 10/2003 | ......... A01K 67/0339 |
| WO | 2005/014791 A2 | | 2/2005 | |
| WO | 2007/025097 A2 | | 3/2007 | |
| WO | 2007/136815 A2 | | 11/2007 | |
| WO | 2008/108989 A2 | | 9/2008 | |
| WO | 2010/021692 A1 | | 2/2010 | |
| WO | 2010/054108 A2 | | 5/2010 | |
| WO | 2010/075424 A2 | | 7/2010 | |
| WO | 2010/076057 A1 | | 7/2010 | |
| WO | 2010/117464 A1 | | 10/2010 | |
| WO | 2010/125471 A2 | | 11/2010 | |
| WO | 2011/011767 A1 | | 1/2011 | |
| WO | 2011/049312 A2 | | 4/2011 | |
| WO | 2011/072246 A2 | | 6/2011 | |
| WO | 2011/146121 A1 | | 11/2011 | |
| WO | 2011/156430 A2 | | 12/2011 | |
| WO | 2011/159369 A1 | | 12/2011 | |
| WO | 2012/012738 A1 | | 1/2012 | |
| WO | 2012/164565 A1 | | 12/2012 | |
| WO | 2013/044008 A2 | | 3/2013 | |
| WO | 2013/082519 A2 | | 6/2013 | |
| WO | 2013/098244 A1 | | 7/2013 | |
| WO | 2013/126794 A1 | | 8/2013 | |
| WO | 2013/130824 A2 | | 9/2013 | |
| WO | 2013/141680 A1 | | 9/2013 | |
| WO | 2013/142578 A1 | | 9/2013 | |
| WO | 2013/155572 A1 | | 10/2013 | |
| WO | 2013/160230 A1 | | 10/2013 | |
| WO | 2013/169398 A2 | | 11/2013 | |
| WO | 2013/169802 A1 | | 11/2013 | |
| WO | 2013/176772 A1 | | 11/2013 | |
| WO | 2013/181440 A1 | | 12/2013 | |
| WO | 2013/186754 A2 | | 12/2013 | |
| WO | 2013/188522 A2 | | 12/2013 | |
| WO | 2013/188638 A2 | | 12/2013 | |
| WO | 2013/192278 A1 | | 12/2013 | |
| WO | 2014/011237 A1 | | 1/2014 | |
| WO | 2014/011901 A2 | | 1/2014 | |
| WO | 2014/018423 A2 | | 1/2014 | |
| WO | 2014/022702 A2 | | 2/2014 | |
| WO | 2014/039684 A1 | | 3/2014 | |
| WO | 2014/039692 A2 | | 3/2014 | |
| WO | 2014/039702 A2 | | 3/2014 | |
| WO | 2014/039872 A1 | | 3/2014 | |
| WO | 2014/059255 A1 | | 4/2014 | |
| WO | 2014/065596 A1 | | 5/2014 | |
| WO | 2014/071006 A2 | | 5/2014 | |
| WO | 2014/089290 A1 | | 6/2014 | |
| WO | 2014/093479 A1 | | 6/2014 | |
| WO | 2014/093595 A1 | | 6/2014 | |
| WO | 2014/093622 A2 | | 6/2014 | |
| WO | 2014/093635 A1 | | 6/2014 | |
| WO | 2014/093655 A2 | | 6/2014 | |
| WO | 2014/093661 A2 | | 6/2014 | |
| WO | 2014/093694 A1 | | 6/2014 | |
| WO | 2014/093701 A1 | | 6/2014 | |
| WO | 2014/093709 A1 | | 6/2014 | |
| WO | 2014/093712 A1 | | 6/2014 | |
| WO | 2014/093718 A1 | | 6/2014 | |
| WO | 2014/099744 A1 | | 6/2014 | |
| WO | 2014/099750 A2 | | 6/2014 | |
| WO | 2014/104878 A1 | | 7/2014 | |
| WO | 2014/113493 A1 | | 7/2014 | |
| WO | 2014/127287 A1 | | 8/2014 | |
| WO | 2014/150624 A1 | | 9/2014 | |
| WO | 2014/204725 A1 | | 12/2014 | |
| WO | 2014/204726 A1 | | 12/2014 | |
| WO | 2014/204727 A1 | | 12/2014 | |
| WO | 2014/204728 A1 | | 12/2014 | |
| WO | 2014/204729 A1 | | 12/2014 | |

OTHER PUBLICATIONS

Järver et al. The use of cell-penetrating peptides as a tool for gene regulation. Drug Discovery Today, vol. 9, No. 9, pp. 395-402, May 2004.*

Han et al. Efficient intracellular delivery of GFP by homeodomains of *Drosophila* Fushi-Tarazu and Engrailed proteins. Molecules and Cells, vol. 10, No. 6, pp. 728-732, 2000.*

Zhang et al. MDV-1 VP22: a transporter that can selectively deliver proteins into cells. Archives of Virology, vol. 154, No. 7, pp. 1027-1034, Jun. 2009.*

Matsui et al. Protein therapy: In vivo protein transduction by polyarginine (11R) PTD and subcellular targeting delivery. Current Protein and Peptide Science, vol. 4, pp. 151-157, 2003.*

Gustafsson et al. Codon bias and heterologous protein expression. TRENDS in Biotechnology, vol. 22, No. 7, pp. 346-353, Jul. 2004.*

Sun et al. Recent advances in targeted genome engineering in mammalian systems. Biotechnology Journal, vol. 7, pp. 1074-1087, Jul. 2012.*

(56) References Cited

OTHER PUBLICATIONS

Chen et al. Transfection and expression of plasmid DNA in plant cells by an arginine-rich intracellular delivery peptide without protoplast preparation. FEBS Letters, vol. 581, pp. 1891-1897, 2007.*
Noguchi et al. Recent advances in protein transduction technology. Cell Transplantation, vol. 19, pp. 649-654, Jun. 2010.*
Dong et al. Cell-penetrating peptide PEP-1-mediated transduction of enhanced green fluorescent protein into human colorectal cancer SW480 cells. Chinese Journal of Cancer, vol. 26, No. 2, pp. 1-6, 2007. (Year: 2007).*
GenBank Accession No. YP_005388840.1, publicly available Apr. 6, 2012, printed as pp. 1/2-2/2. (Year: 2012).*
Smith et al. The nuclear localization signal. Proceedings of the Royal Society of London, vol. 226, pp. 43-58, 1985. (Year: 1985).*
Hu et al. Targeting the *Escherichia coli* lac repressor to the mammalian cell nucleus. Gene, vol. 99, pp. 141-150, 1991. (Year: 1991).*
RPMI Media, printed from https://www.signnaaldrich.com/life-science/cell-culture/classical-media-salts/rpmi-media.html, as pp. 1/2-2/2 on Jan. 10, 2018. (Year: 2018).*
Supplementary information for Cho et al. Nature Biotechnology, vol. 31, No. 3, pp. 230-232, Jan. 29, 2013, printed as pp. 1/11-11/11. (Year: 2013).*
GenBank Accession No. WP_014407541.1, publicly available Jun. 2019, printed as p. 1/1. (Year: 2019).*
Chugh et al. Translocation and nuclear accumulation of monomer and dimer of HIV-1 Tat basic domain domain in triticale mesophyll protoplasts. Biochimica et Biophysica Acta, vol. 1768, pp. 419-429, 2007, available online Nov. 30, 2006. (Year: 2006).*
Chugh et al. Translocation of cell-penetrating peptides and delivery of their cargoes in triticale microspores. Plant Cell Reports, vol. 28, pp. 801-810, 2009. (Year: 2009).*
Chugh et al. Cell-penetrating peptides: Nanocarrier for macromolecule delivery in living cells. IUBMB Life, vol. 62, pp. 183-193, Mar. 12, 2010. (Year: 2010).*
Wender et al. The design, synthesis, and evaluation of molecules that enable or enhance cellular uptake: Peptoid molecular transporters. Proceedings of the National Academy of Sciences, USA, vol. 97, No. 24, pp. 13003-13008, Nov. 21, 2000. (Year: 2000).*
Zhang et al. Efficient gene deletion and replacement in Aspergilus niger by modified in vivo CRISPR/Cas9 systems. Bioresources and Bioprocessing, vol. 6, 4, 2019, printed as pp. 1/8-8/8 (Year: 2019).*
Chatterjee et al. In vivo analysis of nuclear protein traffic in mammalian cells. Experimental Cell Research, vol. 236, 346-350, (Year: 1997) 1997.*
Al-Attar et al., "Clustered regularly interspaced short palindromic repeats (CRISPRs): the hallmark of an ingenious antiviral defense mechanism in prokaryotes", Biological Chemistry, 2011, pp. 277-289, vol. 392, No. 4.
Barrangou, "RNA-mediated programmable DNA cleavage", Nature Biotechnology, 2012, pp. 836-838, vol. 30, No. 9.
Bassett et al., "Highly Efficient Targeted Mutagenesis of *Drosophila* with the CRISPR/Cas9 System", Cell Reports, 2013, pp. 220-228, vol. 4.
Beerli et al., "Engineering polydactyl zinc-finger transcription factors", Nature Biotechnology, 2002, pp. 135-141, vol. 20.
Belfort et al., "Homing endonucleases: keeping the house in order", Nucleic Acids Research, 1997, pp. 3379-3388, vol. 25, No. 17.
Bogdanove et al., "TAL Effectors: Customizable Proteins for DNA Targeting", Science, 2011, pp. 1843-1846, vol. 333.
Chalaya et al., "Tissue Specificity of Methylation of Cytosines in Regulatory Regions of Four Genes Located in the Locus FXYD5-COX7A1 of Human Chromosome 19: Correlation with Their Expression Level", Biochemistry (Moscow), 2006, pp. 294-299, vol. 71, No. 3.
Cho et al., "Targeted genome engineering in human cells with the Cas9 RNA-guided endonuclease", Nature Biotechnology, 2013, pp. 230-232, vol. 31, No. 3.
Choo et al., "Advances in zinc finger engineering", Current Opinion in Structural Biology, 2000, pp. 411-416, vol. 10.
Cong et al., "Multiplex Genome Engineering Using CRISPR/Cas Systems", Science, 2013, pp. 819-823, vol. 339.
Cristea et al., "In vivo Cleavage of Transgene Donors Promotes Nuclease-Mediated Targeted Integration", Biotechnology and Bioengineering, 2012, pp. 871-880, vol. 110, No. 3.
Deltcheva et al., "CRISPR RNA maturation by trans-encoded small RNA and host factor RNase III", Nature, 2011, pp. 602-607, vol. 471.
Doyon et al., "Heritable Targeted Gene Disruption in Zebrafish Using Designed Zinc Finger Nucleases", Nature Biotechnology, 2008, pp. 702-708, vol. 26, No. 6.
Doyon et al., "Enhancing zinc-finger-nuclease activity with improved obligate heterodimeric architectures", Nature Methods, 2011, pp. 74-79, vol. 8, No. 1.
Durai et al., "Zinc finger nucleases: custom-designed molecular scissors for genome engineering of plant and mammalian cells", Nucleic Acids Research, 2005, pp. 5978-5990, vol. 33, No. 18.
Friedland et al., "Heritable genome editing in C. elegans via a CRISPR-Cas9 system", Nature Methods, 2013, pp. 741-743, vol. 10, No. 8.
Fu et al., "High-frequency off-target mutagenesis induced by CRISPR-Cas nucleases in human cells", Nature Biotechnology, 2013, pp. 822-826, vol. 31, No. 3.
Gasiunas et al., "Cas9-crRNA ribonucleoprotein complex mediates specific DNA cleavage for adaptive immunity in bacteria", PNAS, 2012, pp. E2579-E2586, vol. 109, No. 39.
Gribskov et al., "Sigma factors from *E. coli*, B. subtilis, phage SP01, and phage T4 are homologous proteins", Nucleic Acids Research, 1986, pp. 6745-6763, vol. 14, No. 16.
Hale et al., "Essential Features and Rational Design of CRISPR RNAs that Function with the Cas RAMP Module Complex to Cleave RNAs", Molecular Cell, 2012, pp. 292-302, vol. 45, No. 3.
Hwang et al., "Efficient genome editing in zebrafish using a CRISPR-Cas system", Nature Biotechnology, 2013, pp. 227-229, vol. 31, No. 3.
International Search Report and Written Opinion from related International Application No. PCT/US2013/073307, dated Feb. 26, 2014; 13 pgs.
International Preliminary Report on Patentability from related International Application No. PCT/US2013/073307, dated Jun. 18, 2015; 10 pgs.
Isalan et al., "A rapid, generally applicable method to engineer zinc fingers illustrated by targeting the HIV-1 promoter", Nature Biotechnology, 2001, pp. 656-660, vol. 19, No. 7.
Iseli et al., "Indexing Strategies for Rapid Searches of Short Words in Genome Sequences", PloS ONE, 2007, e579, 8 pgs., vol. 2, No. 6.
Jiang et al., "RNA-guided editing of bacterial genomes using CRISPR-Cas systems", Nature Biotechnology, 2013, pp. 233-239, vol. 31, No. 3.
Jiang et al., "The structural biology of CRISPR-Cas systems", Current Opinion in Structural Biology, 2015, pp. 100-111, vol. 30.
Jinek et al., "A Programmable Dual-RNA-Guided DNA Endonuclease in Adaptive Bacterial Immunity", Science, 2012, pp. 816-821, vol. 337.
Jinek et al., "RNA-programmed genome editing in human cells", eLIFE, 2013, pp. 1-9, vol. 2, e00471.
Kandavelou et al., "Targeted manipulation of mammalian genomes using designed zinc finger nucleases", Biochemical and Biophysical Research Communications, 2009, pp. 56-61, vol. 388.
Kryukov et al., "A New Database (GCD) on Genome Composition for Eukaryote and Prokaryote Genome Sequences and Their Initial Analyses", Genome Biology and Evolution, 2012, pp. 501-512, vol. 4, No. 4.
Lange et al., "Classical Nuclear Localization Signals: Definition, Function, and Interaction with Importin α", The Journal of Biological Chemistry, 2007, pp. 5101-5105, vol. 282, No. 8.
Li et al. "Harnessing Type I and Type III CRISPR-Cas systems for genome editing", Nucleic Acids Research, 2016, a34, pp. 1-12, vol. 44, No. 4.

(56) References Cited

OTHER PUBLICATIONS

Lombardo et al., "Gene editing in human stem cells using zinc finger nucleases and integrase-defective lentiviral vector delivery", Nature Biotechnology, 2007, pp. 1298-1306, vol. 25, No. 11.

Mak et al., "TAL effectors: function, structure, engineering and applications", Current Opinion in Structural Biology, 2013, pp. 93-99, vol. 23, No. 1.

Makarova et al., "Unification of Cas protein families and a simple scenario for the origin and evolution of CRISPR-Cas systems", Biology Direct, 2011, pp. 1-27, vol. 6, No. 38.

Makarova et al., "Evolution and classification of the CRISPR-Cas systems", Nature Review Microbiology, 2011, pp. 467-477, vol. 9, No. 6.

Mali et al., "CAS9 transcriptional activators for target specificity screening and paired nickases for cooperative genome engineering", Nature Biotechnology, 2013, pp. 833-838, vol. 31.

Mali et al., "RNA-Guided Human Genome Engineering via Cas9", Science, 2013, pp. 823-826, vol. 339.

Manjunath et al., "Newer Gene Editing Technologies toward HIV Gene Therapy", Viruses, 2013, pp. 2748-2766, vol. 5.

Marraffini et al., "CRISPR interference: RNA-directed adaptive immunity in bacteria and archaea", Nature Reviews, Genetics, 2010, pp. 181-190, vol. 11.

Miller et al., "An improved zinc-finger nuclease architecture for highly specific genome editing", Nature Biotechnology, 2007, pp. 778-785, vol. 25, No. 7.

Minczuk et al., "Sequence-specific modification of mitochondrial DNA using a chimeric zinc finger methylase", PNAS, 2006, pp. 19689-19694, vol. 103, No. 52.

Moehle et al., "Targeted gene addition into a specified location in the human genome using designed zinc finger nucleases", PNAS, 2007, pp. 3055-3060, vol. 104, No. 9.

Nakamura et al., "Codon usage tabulated from international DNA sequence databases: status for the year 2000", Nucleic Acids Research, 2000, p. 292, vol. 28, No. 1.

Office Action from related U.S. Appl. No. 14/649,777, dated May 4, 2016; 24 pgs.

Office Action from related U.S. Appl. No. 14/213,895, dated Mar. 14, 2016; 14 pgs.

Office Action from related U.S. Appl. No. 14/292,212, dated Mar. 12, 2015; 12 pgs.

Office Action from related U.S. Appl. No. 14/292,212, dated Nov. 14, 2014; 17 pgs.

Office Action from related U.S. Appl. No. 14/292,212, dated Jul. 28, 2014; 14 pgs.

Orlando et al., "Zinc-finger nuclease-driven targeted integration into mammalian genomes using donors with limited chromosomal homology", Nucleic Acids Research, 2010, pp. 1-15, vol. 38, No. 15:e152.

Pabo et al., "Design and Selection of Novel Cys2 His2 Zinc Finger Proteins", Annual Review of Biochemistry, 2001, pp. 313-340, vol. 70.

Pattanayak et al., "High-throughput profiling of off-target DNA cleavage reveals RNA-programmed Cas9 nuclease specificity", Nature Biotechnology, 2013, pp. 839-843, vol. 31, No. 9.

Qi et al., "RNA processing enables predictable programming of gene expression", Nature Biotechnology, 2012, pp. 1002-1006, vol. 30, No. 10.

Ran et al., "Double Nicking by RNA-Guided CRISPR Cas9 for Enhanced Genome Editing Specificity", Cell, 2013, pp. 1380-1389, vol. 154.

Richter et al., "Exploiting CRISPR/Cas: Interference Mechanisms and Applications", International Journal of Molecular Sciences, 2013, pp. 14518-14531, vol. 14.

Santiago et al., "Targeted gene knockout in mammalian cells by using engineered zinc-finger nucleases", PNAS, 2008, pp. 5809-5814, vol. 105, No. 15.

Segal et al., "Custom DNA-binding proteins come of age: polydactyl zinc-finger proteins", Current Opinion in Biotechnology, 2001, pp. 632-637, vol. 12.

Sigma-Aldrich Product Information, Custom CRISPR Plasmid, 2013, 5 pgs.

Smith et al., "Comparison of Biosequences", Advances in Applied Mathematics, 1981, pp. 482-489, vol. 2.

Szczepek et al., "Structure-based redesign of the dimerization interface reduces the toxicity of zinc-finger nucleases", Nature Biotechnology, 2007, pp. 786-793, vol. 25, No. 7.

Third Party Observation filed in related International Application No. PCT/US2013/ 073307, dated Apr. 13, 2015; 12 pgs.

Third-Party Submission Under 37 CFR 1.290 filed in related U.S. Appl. No. 14/213,895, dated Mar. 16, 2015; 21 pgs.

Third-Party Submission Under 37 CFR 1.290 filed in related U.S. Appl. No. 14/292,212, dated Mar. 16, 2015; 11 pgs.

Third-Party Submission Under 37 CFR 1.290 filed in related U.S. Appl. No. 14/649,777, dated Jul. 26, 2016; 78 pgs.

Urnov et al., "Highly efficient endogenous human gene correction using designed zinc-finger nucleases", Nature, 2005, pp. 646-651, vol. 435.

U.S. Appl. No. 61/736,527, filed Dec. 12, 2012; 306 pgs.

U.S. Appl. No. 61/738,355, filed Dec. 17, 2012; 63 pgs.

U.S. Appl. No. 61/757,640, filed Jan. 28, 2013; 361 pgs.

U.S. Appl. No. 61/781,598, filed Mar. 14, 2013; 31 pgs.

Wang et al., "One-Step Generation of Mice Carrying Mutations in Multiple Genes by CRISPR/Cas-Mediated Genome Engineering", Cell, 2013, pp. 910-918, vol. 153.

Wiedenheft et al., "RNA-guided genetic silencing systems in bacteria and archaea", Nature, 2012, pp. 331-338, vol. 482.

Zhang et al., "Synthetic Zinc Finger Transcription Factor Action at an Endogenous Chromosomal Site: Activation of the Human Erythropoietin Gene", The Journal of Biological Chemistry, 2000, pp. 33850-33860, vol. 275, No. 43.

Bitinaite et al., "FokI dimerization is required for DNA cleavage," PNAS, 1998, pp. 10570-10575, vol. 95.

Carroll et al., "A CRISPR Approach to Gene Targeting," Molecular Therapy, 2012, pp. 1658-1660, vol. 20, No. 9.

European Search Report from related European Application No. 13859964.2, dated Sep. 5, 2016; 8 pgs.

Gunther, "Concentration, compartmentation and metabolic function of intracellular free Mg2+," Magnesium Research, 2006, pp. 225-236, vol. 19, No. 4.

Hsu et al., "DNA targeting specificity of RNA-guided Cas9 nucleases," Nature Biotechnology, 2013, pp. 827-832, vol. 31, No. 9.

Jinek et al., Supplementary Materials for "A Programmable Dual-RNA-Guided DNA Endonuclease in Adaptive Bacterial Immunity," Science, 2012, 37 pgs.

Lamartina et al., "Selective Cleavage of AAVS1 Substrates by the Adeno-Associated Virus Type 2 Rep68 Protein Is Dependent on Topological and Sequence Constraints," Journal of Virology, 2000, pp. 8831-8842, vol. 74, No. 19.

Lambowitz et al., "Group II Introns: Mobile Ribozymes that Invade DNA," Cold Spring Harb Perspect Biol, 2011; 3:a003616; 19 pgs.

Lusk et al., "Magnesium and the Growth of *Escherichia coli*," The Journal of Biological Chemistry, 1968, pp. 2618-2624, vol. 243, No. 10.

Mastroianni et al., "Group II Intron-Based Gene Targeting Reactions in Eukaryotes," PLoS ONE, 2008, e3121, pp. 1-15, vol. 3, No. 9.

Mohr et al., "Rules for DNA target-site recognition by a lactococcal group II intron enable retargeting of the intron to specific DNA sequences," Genes & Development, 2000, pp. 559-573, vol. 14.

Office Action and Search Report from related Singapore Patent Application No. 11201503824S, dated Oct. 14, 2016; 14 pgs.

Office Action from related U.S. Appl. No. 15/188,931, dated Sep. 22, 2016; 32 pgs.

Office Action from related U.S. Appl. No. 15/188,927, dated Sep. 27, 2016; 43 pgs.

Office Action from related U.S. Appl. No. 15/188,911, dated Aug. 12, 2016; 39 pgs.

Office Action from related U.S. Appl. No. 14/292,212, dated Oct. 18, 2016; 30 pgs.

Sapranauskas et al., "The *Streptococcus thermophilus* CRISPR/Cas system provides immunity in *Escherichia coli*," Nucleic Acids Research, 2011, pp. 9275-9282, vol. 39, No. 21.

(56) References Cited

OTHER PUBLICATIONS

Truong et al., "Enhanced group II intron retrohoming in magnesium-deficient *Escherichia coli* via selection of mutations in the ribozyme core," PNAS, 2013, pp. E3800-E3809, vol. 110, No. 40.
Nagarajan et al., "A Hierarchy of Nuclear Localization Signals Governs the Import of the Regulatory Factor X Complex Subunits and MHC Class II Expression," The Journal of Immunology, 2004, pp. 410-419, vol. 173, No. 1.
Nakahara et al., "Genetic Evidence for Single-Strand Lesions Initiating Nbs1-Dependent Homologous Recombination in Diversification of Ig V in Chicken B Lymphocytes," PLoS Genetics, 2009, e1000356, pp. 1-15, vol. 5, No. 1.
Nakai et al., "PSORT: a program for detecting sorting signals in proteins and predicting their subcellular localization," Trends in Biochemical Sciences, 1999, pp. 34-35, vol. 24.
Noguchi et al., "PDX-1 Protein Containing Its Own Antennapedia-Like Protein Transduction Domain Can Transduce Pancreatic Duct and Islet Cells," Diabetes, 2003, pp. 1732-1737, vol. 52, No. 7.
Oakes et al., "Profiling of engineering hotspots identifies an allosteric CRISPR-Cas9 switch," Nature Biotechnology, 2016, pp. 646-651, vol. 34, No. 6.
Office Action from related U.S. Appl. No. 15/188,931, dated Apr. 21, 2017; 41 pgs.
Office Action from related U.S. Appl. No. 15/188,927, dated Apr. 21, 2017; 29 pgs.
Office Action from related U.S. Appl. No. 15/188,911, dated Apr. 17, 2017; 42 pgs.
Office Action from related U.S. Appl. No. 15/456,204, dated May 18, 2017; 47 pgs.
Office Action from related Australian Patent Application No. 2013355214, dated Mar. 9, 2017; 4 pgs.
Office Action from related Canadian Patent Application No. 2,891,347, dated May 30, 2017; 4 pgs.
First Office Action and Search Report from related Chinese Patent Application No. 201380072477.4, dated Mar. 1, 2017; 16 pgs.
Second Office Action from related Chinese Patent Application No. 201380072477.4, dated Aug. 28, 2017; 8 pgs.
Office Action from related Japanese Patent Application No. 2015-545838, dated Aug. 22, 2017; 10 pgs.
Office Action from related European Patent Application No. 16183723.2, dated Jun. 2, 2017; 5 pgs.
Office Action from related European Patent Application No. 16183725.7, dated May 22, 2017; 9 pgs.
Office Action from related Japanese Patent Application No. 2017-115672, dated Aug. 8, 2017; 9 pgs.
Office Action from related Australian Patent Application No. 2017204031, dated Jul. 14, 2017; 3 pgs.
O'Hare et al., "Transformation of mouse fibroblasts to methotrexate resistance by a recombinant plasmid expressing a prokaryotic dihydrofolate reductase," PNAS, 1981, pp. 1527-1531, vol. 78, No. 3.
O'Neill et al., "Nucleosome Arrays Inhibit Both Initiation and Elongation of Transcripts by Bacteriophage T7 RNA Polymerase," J. Mol. Biol., 1992, pp. 67-78, vol. 223, No. 1.
Pandika, "Rising Stars: Jennifer Doudna, CRISPR Code Killer," Ozy (Jan. 7, 2014), http://www.ozy.com/rising-stars/jennifer-doudna-crispr-code-killer/4690, 6 pgs.
Park et al., "Regulation of Ribosomal S6 Kinase 2 by Mammalian Target of Rapamycin," The Journal of Biological Chemistry, 2002, pp. 31423-31429, vol. 277, No. 35.
Patterson et al., "Codon optimization of bacterial luciferase (lux) for expression in mammalian cells," J Ind Microbial Biotechnol, 2005, pp. 115-123, vol. 32.
Perez-Pinera et al., "Advances in Targeted Genome Editing," Curr Opin Chem Biol., 2012, pp. 268-277, vol. 1-6, No. 3-4.
Planey et al., "Inhibition of Glucocorticoid-induced Apoptosis in 697 Pre-B Lymphocytes by the Mineralocorticoid Receptor N-terminal Domain," The Journal of Biological Chemistry, 2002, pp. 42188-42196, vol. 277, No. 44.

Platt et al., "CRISPR-Cas9 Knockin Mice for Genome Editing and Cancer Modeling," Cell, 2014, pp. 440-455, vol. 159.
Porteus et al., "Chimeric Nucleases Stimulate Gene Targeting in Human Cells," Science, 2003, p. 763, vol. 300.
Porteus et al., "Gene targeting using zinc finger nucleases," Nature Biotechnology, 2005, pp. 967-973, vol. 23, No. 8.
Primo et al., "Lentiviral vectors for cutaneous RNA managing," Experimental Dermatology, 2012, pp. 162-170, vol. 21, No. 3.
Radulovich et al., "Modified gateway system for double shRNA expression and Cre/lox based gene expression," BMC Biotechnology, 2011, pp. 1-9, vol. 11, No. 24.
Ran et al., "Genome engineering using the CRISPR-Cas9 system," Nature Protocols, 2013, pp. 2281-2308, vol. 8, No. 11, along with supporting information.
Raymond et al., "High-Efficiency FLP and ΦC31 Site-Specific Recombination in Mammalian Cells," PLoS ONE, 2007, e162, pp. 1-4, Issue 1.
Rebar et al., "Induction of angiogenesis in a mouse model using engineered transcription factors," Nature Medicine, 2002, pp. 1427-1432, vol. 8, No. 12.
Reiss et al., "RecA protein stimulates homologous recombination in plants," PNAS, 1996, pp. 3094-3098, vol. 93, No. 7.
Richter et al., "Function and Regulation of Clustered Regularly Interspaced Short Palindromic Repeats (CRISPR) / CRISPR Associated (Cas) Systems," Viruses, 2012, pp. 2291-2311, vol. 4, No. 10.
Roberts et al., "The Effect of Protein Context on Nuclear Location Signal Function," Cell, 1987, pp. 465-475, vol. 50, No. 3.
Roberts, "Nuclear location signal-mediated protein transport," Biochimica et Biophysica Acta, 1989, pp. 263-280, vol. 1008, No. 3.
Rodrigues et al., "Red Fluorescent Protein (DsRed) as a Reporter in *Saccharomyces cerevisiae*," Journal of Bacteriology, 2001, pp. 3791-3794, vol. 183, No. 12.
Romani et al., "Hormonal regulation of Mg2+ transport and homeostasis in eukaryotic cells," BioMetals, 2002, pp. 271-283, vol. 15.
Sanjana et al., "A transcription activator-like effector toolbox for genome engineering," Nature Protocols, 2012, pp. 171-192, vol. 7, No. 1.
Sato et al., "Generation of Adeno-Associated Virus Vector Enabling Functional Expression of Oxytocin Receptor and Fluorescence Marker Genes Using the Human eIF4G Internal Ribosome Entry Site Element," Bioscience, Biotechnology, and Biochemistry, 2009, pp. 2145-2148, vol. 73, No. 9.
Sauer et al., "Site-specific DNA recombination in mammalian cells by the Cre recombinase of bacteriophage P1," PNAS, 1988, pp. 5166-5170, vol. 85.
Schiml et al., "Revolutionizing plant biology: multiple ways of genome engineering by CRISPR/Cas," Plant Methods, 2016, pp. 1-9, vol. 12, No. 8.
Schramm et al., "Recruitment of RNA polymerase III to its target promoters," Genes & Development, 2002, pp. 2593-2620, vol. 16, No. 20.
Sebo et al., "A simplified and efficient germline-specific CRISPR/Cas9 system for *Drosophila* genomic engineering," Fly, 2014, pp. 52-57, vol. 8, No. 1.
Shieh et al., "Nuclear Targeting of the Maize R Protein Requires Two Nuclear Localization Sequences," Plant Physiol., 1993, pp. 353-361, vol. 101.
Alberts et al., "A Special Nucleotide-Polymerizing Enzyme Synthesizes Short RNA Primer Molecules on the Lagging Strand," Molecular Biology of The Cell, 2002, 4th Ed., Garland Science, New York, NY, p. 244.
Barrangou, "CRISPR-Cas systems and RNA-guided interference," Wiley Interdisciplinary Reviews: RNA, 2013, pp. 267-278, vol. 4, No. 3.
Bikard et al., "Programmable repression and activation of bacterial gene expression using an engineered CRISPR-Cas system," Nucleic Acids Research, 2013, pp. 7429-7437, vol. 41, No. 15.
Charpentier et al., "Biotechnology: Rewriting a genome," Nature, 2013, pp. 50-51, vol. 495, No. 7439.
Christian et al., "Targeting DNA Double-Strand Breaks with TAL Effector Nucleases," Genetics, 2010, pp. 757-761, vol. 186, No. 2, including 8 pgs. of Supporting Information.

(56) References Cited

OTHER PUBLICATIONS

Deng et al., "Structural Basis for Sequence-Specific Recognition of DNA by TAL Effectors," Science, 2012, pp. 720-723, vol. 335.
European Search Report from related European Application No. 13859964.2, dated Jan. 31, 2017; 24 pgs.
European Search Report from related European Application No. 16183717.4, dated Feb. 3, 2017; 12 pgs.
European Search Report from related European Application No. 16183719.0, dated Feb. 1, 2017; 12 pgs.
European Search Report from related European Application No. 16183720.8, dated Feb. 10, 2017; 11 pgs.
European Search Report from related European Application No. 16183723.2, dated Feb. 7, 2017; 15 pgs.
European Search Report from related European Application No. 16183724.0, dated Feb. 3, 2017; 15 pgs.
European Search Report from related European Application No. 16183725.7, dated Feb. 3, 2017; 17 pgs.
Farzadfard et al., "Tunable and Multifunctional Eukaryotic Transcription Factors Based on CRISPR/Cas," ACS Synthetic Biology, 2013, pp. 604-613, vol. 2, No. 10.
Fonfara et al., "Creating highly specific nucleases by fusion of active restriction endonucleases and catalytically inactive homing endonucleases," Nucleic Acids Research, 2011, pp. 1-14.
Gilbert et al., "CRISPR-Mediated Modular RNA-Guided Regulation of Transcription in Eukaryotes," Cell, 2013, pp. 442-451, vol. 154, No. 2, including 5 pgs. of Supplemental Information.
Haft et al., "A Guild of 45 CRISPR-Associated (Cas) Protein Families and Multiple CRISPR/Cas Subtypes Exist in Prokaryotic Genomes," PLoS Computational Biology, 2005, e60, pp. 0474-0483, vol. 1, No. 6.
Katada et al., "Chemical and biological approaches to improve the efficiency of homologous recombination in human cells mediated by artificial restriction DNA cutter," Nucleic Acids Research, 2012, e81, 8 pgs., vol. 40, No. 11.
Kim et al., "Hybrid restriction enzymes; Zinc finger fusions to Fok I cleavage domain," PNAS, 1996, pp. 1156-1160, vol. 93.
Kim et al., "Precision genome engineering with programmable DNA-nicking enzymes," Genome Research, 2012, pp. 1327-1333, vol. 22, No. 7.
Office Action from related U.S. Appl. No. 14/213,895, dated Jan. 19, 2017; 15 pgs.
Office Action from related U.S. Appl. No. 15/188,931, dated Nov. 30, 2016; 22 pgs.
Office Action from related U.S. Appl. No. 15/188,927, dated Dec. 1, 2016; 16 pgs.
Office Action from related U.S. Appl. No. 15/188,911, dated Dec. 30, 2016; 53 pgs.
Office Action from related U.S. Appl. No. 15/188,909, dated Dec. 30, 2016; 24 pgs.
Office Action from related U.S. Appl. No. 15/188,902, dated Jan. 3, 2017; 28 pgs.
Office Action from related U.S. Appl. No. 15/188,899, dated Dec. 30, 2016; 27 pgs.
Qi et al., "Repurposing CRISPR as an RNA-Guided Platform for Sequence-Specific Control of Gene Expression," Cell, 2013, pp. 1173-1183, vol. 152, No. 5.
Ryu et al., "Enhanced Uptake of a Heterologous Protein with an HIV-1 Tat Protein Transduction Domains (PTD) at Both Termini," Molecules and Cells, 2003, pp. 385-391, vol. 16, No. 3.
Shen et al., "Generation of gene-modified mice via Cas9/RNA-mediated gene targeting," Cell Research, 2013, pp. 720-723, vol. 23, No. 5.
Andreas et al., "Enhanced efficiency through nuclear localization signal fusion on phage oC31-integrase: activity comparison with Cre and FLPe recombinase in mammalian cells," Nucleic Acids Research, 2002, pp. 2299-2306, vol. 30, No. 11.
Au et al., "Characterization of a baculovirus nuclear localization signal domain in the late expression factor 3 protein," Virology, 2009, pp. 209-217, vol. 385, No. 1.
Baiker et al., "The Immediate-Early 63 Protein of Varicella-Zoster Virus: Analysis of Functional Domains Required br Replication In Vitro and for T-Cell and Skin Tropism in the SCIDhu Model In Vivo," Journal of Virology, 2004, pp. 1181-1194, vol. 78, No. 3.
Baker, "Gene editing at CRISPR speed," Nature Biotechnology, 2014, pp. 309-312, vol. 32, No. 4.
Birch, "Plant Transformation: Problems and Strategies for Practical Application," Annu. Rev. Plant Physiol. Plant Mol. Biol., 1997, pp. 297-326, vol. 48.
Bobis-Wozowicz et al., "Targeted genome editing in pluripotent stem cells using zinc-finger nucleases," Methods, 2011, pp. 339-346, vol. 53.
Boden et al., "Efficient Gene Transfer of HIV-1-Specific Short Hairpin RNA into Human Lymphocytic Cells Using Recombinant Adeno-associated Virus Vectors," Molecular Therapy, 2004, pp. 396-402, vol. 9, No. 3.
Bouard et al., "Themed Section: Vector Design and Drug Delivery Review—Viral vectors: from virology to transgene expression," British Journal of Pharmacology, 2009, pp. 153-165, vol. 157.
Brouns, "A Swiss Army Knife of Immunity," Science, 2012, pp. 808-809, vol. 337, No. 6096.
Campeau et al., "A Versatile Viral System for Expression and Depletion of Proteins in Mammalian Cells," PLoS ONE, 2009, e6529, pp. 1-18, vol. 4, No. 8.
Carlson et al., "Targeting DNA With Fingers and TALENs," Molecular Therapy-Nucleic Acids, 2012, e3, pp. 1-4, vol. 1.
Carney et al., "Induction of DNA Double-Strand Breaks by Electroporation of Restriction Enzymes into Mammalian Cells," Methods in Molecular Biology, 1999, pp. 465-471, vol. 113.
Carr et al., "Genome engineering," Nature Biotechnology, 2009, pp. 1151-1162, vol. 27, No. 12.
Carroll, "Zinc-finger Nucleases as Gene Therapy Agents," Gene Ther., 2008, pp. 1463-1468, vol. 15, No. 22.
Cermak et al., "Efficient design and assembly of custom TALEN and other TAL effector-based constructs for DNA targeting," Nucleic Acids Research, 2011, e82, pp. 1-11, vol. 39, No. 12.
Certo et al., "Tracking genome engineering outcome at individual DNA breakpoints," Nature Methods, 2011, pp. 671-676, vol. 8, No. 8.
Chan et al., "Characterization of the Kinetochore Binding Domain of CENP-E Reveals Interactions with the Kinetochore Proteins CENP-F and hBUBR1," The Journal of Cell Biology, 1998, pp. 49-63, vol. 143, No. 1.
Hang et al., "Genome editing with RNA-guided Cas9 nuclease in Zebrafish embryos," Cell Research, 2013, pp. 465-472, vol. 23, No. 4.
Cheng et al., "Multiplexed activation of endogenous genes by CRISPR-on, an RNA-guided transcriptional activator system," Cell Research, 2013, pp. 1163-1171, vol. 23, No. 10.
Chiu et al., "Engineered GFP as a vital reporter in plants," Current Biology, 1996, pp. 325-330, vol. 6, No. 3.
Cho et al., "Heritable Gene Knockout in Caenorhabditis elegans by Direct Injection of Cas9-sgRNA Ribonucleoproteins," Genetics, 2013, pp. 1177-1180, vol. 195.
Choulika et al., "Transfer of Single Gene-Containing Long Terminal Repeats into the Genome of Mammalian Cells by a Retroviral Vector Carrying the cre Gene and the loxP Site," Journal of Virology, 1996, pp. 1792-1798, vol. 70, No. 3.
Chylinski et al., "The tracrRNA and Cas9 families of type II CRISPR-Cas immunity systems," RNA Biology, 2013, pp. 726-737, vol. 10, No. 5.
Clark et al., "A TALE of Two Nucleases: Gene Targeting for the Masses?," Zebrafish, 2011, pp. 147-149, vol. 8, No. 3.
"The CRISPR Revolution," Catalyst, Spring/Summer 2014, vol. 9, pp. 18-20, College of Chemistry, University of California, Berkeley, available at: http://catalyst.berkeley.edu/slideshow/the-crispr-revolution/.
Dai et al., "The Transcription Factors GATA4 and dHAND Physically Interact to Synergistically Activate Cardiac Gene Expression through a p300-dependent Mechanism," The Journal of Biological Chemistry, 2002, pp. 24390-24398, vol. 277, No. 27.

(56) References Cited

OTHER PUBLICATIONS

DiCarlo et al., "Genome engineering in *Saccharomyces cerevisiae* using CRISPR-Cas systems," Nucleic Acids Research, 2013, pp. 4336-4343, vol. 41, No. 7.
Dingwall et al., "A Polypeptide Domain That Specifies Migration of Nucleoplasmin into the Nucleus," Cell, 1982, pp. 449-458, vol. 30, No. 2.
Dingwall et al., "The Nucleoplasmin Nuclear Location Sequence Is Larger and More Complex than That of SV-40 Large T Antigen," The Journal of Cell Biology, 1988, pp. 841-849, vol. 107, No. 3.
Do et al., "Identification of multiple nuclear localization signals in murine Elf3, an ETS transcription factor," FEBS Letters, 2006, pp. 1865-1871, vol. 580, No. 7.
Dworetzky et al., "The Effects of Variations in the Number and Sequence of Targeting Signals on Nuclear Uptake," The Journal of Cell Biology, 1988, pp. 1279-1287, vol. 107, No. 4.
Espinoza et al., "Characterization of the structure, function, and mechanism of B2 RNA, an ncRNA repressor of RNA polymerase II transcription," RNA, 2007, pp. 583-596, vol. 13, No. 4.
Feng et al., "Expanding CRISPR/Cas9 Genome Editing Capacity in Zebrafish Using SaCas9," G3-Genes/Genomes/Genetics, 2016, pp. 2517-2521, vol. 6, No. 8.
Fieck et al., "Modifications of the *E.coli* Lac repressor for expression in eukaryotic cells: effects of nuclear signal sequences on protein activity and nuclear accumulation," Nucleic Acids Research, 1992, pp. 1785-1791, vol. 20, No. 7.
Fischer-Fantuzzi et al., "Cell-Dependent Efficiency of Reiterated Nuclear Signals in a Mutant Simian Virus 40 Oncoprotein Targeted to the Nucleus," Molecular and Cellular Biology, 1988, pp. 5495-5503, vol. 8, No. 12.
Foecking et al., "Powerful and versatile enhancer-promoter unit for mammalian expression vectors," Gene, 1986, pp. 101-105, vol. 45.
Singer et al., "Applications of Lentiviral Vectors for shRNA Delivery and Transgenesis," Curr Gene Ther., 2008, pp. 483-488, vol. 8, No. 6.
Smith et al., "Generation of a nicking enzyme that stimulates site-specific gene conversion from the I-AniI LAGLIDADG homing endonuclease," PNAS, 2009, pp. 5099-5104, vol. 106, No. 13.
Sung et al. "Mouse genetics: Catalogue and scissors," BMB Reports, 2012, pp. 686-692, vol. 45, No. 12.
Swarthout et al., "Zinc Finger Nucleases: A new era for transgenic animals," Annals of Neurosciences, 2011, pp. 25-28, vol. 18, No. 1.
Tinland et al., "The T-DNA-linked VirD2 protein contains two distinct functional nuclear localization signals," PNAS, 1992, pp. 7442-7446, vol. 89.
Tsai et al., "Dimeric CRISPR RNA-guided FokI nucleases for highly specific genome editing," Nature Biotechnology, 2014, pp. 569-576, vol. 32, No. 6.
Urnov et al., "Genome editing with engineered zinc finger nucleases," Nature Reviews/Genetics, 2010, pp. 636-646, vol. 11.
Van den Ackerveken et al., "Recognition of the Bacterial Avirulence Protein AvrBs3 Occurs inside the Host Plant Cell," Cell, 1996, pp. 1307-1316, vol. 87, No. 7.
Villion et al., "The double-edged sword of CRISPR-Cas systems," Cell Research, 2013, pp. 15-17, vol. 23, No. 1.
Wagner et al., "Efficient CRISPR/Cas9-mediated genome editing in P. falciparum," Nature Methods, 2014, pp. 915-918, vol. 11, No. 9.
Welch et al., "Designing Genes for Successful Protein Expression," Methods in Enzymology, Chapter Three, 2011, pp. 43-66, vol. 498.
Wirtz et al., "Regulated processive transcription of chromatin by T7 RNA polymerase in Trypanosoma brucei," Nucleic Acids Research, 1998, pp. 4626-4634, vol. 26, No. 20.
Wolff et al., "Nuclear security breached," Nature Biotechnology, 2001, pp. 1118-1120, vol. 19.
Xiao et al., "Chromosomal deletions and inversions mediated by TALENs and CRISPR/Cas in zebrafish," Nucleic Acids Research, 2013, e141, pp. 1-11, vol. 41, No. 14.
Xie et al., "RNA-Guided Genome Editing in Plants Using a CRISPR-Cas System," Molecular Plant, 2013, pp. 1975-1983, vol. 6, No. 6.
Xie et al., "Boosting CRISPR/Cas9 multiplex editing capability with the endogenous tRNA-processing system," PNAS, 2015, pp. 3570-3575, vol. 112, No. 11.
Xu, "The Next Generation Biotechnology for Apple Improvement and Beyond: The CRISPR/Cas9 Story," New York Fruit Quarterly, 2013, pp. 19-22, vol. 21, No. 4.
Yang et al., "One-Step Generation of Mice Carrying Reporter and Conditional Alleles by CRISPR/Cas Mediated Genome Engineering," Cell, 2013, pp. 1370-1379, vol. 154.
Yi et al., "Current Advances in Retroviral Gene Therapy," Current Gene Therapy, 2011, pp. 218-228, vol. 11, No. 3.
Yoshioka et al., "Development of a mono-promoter-driven CRISPR/Cas9 system in mammalian cells," Nature Scientific Reports, 2015, 18341, pp. 1-8, vol. 5.
Yu et al., "Highly Efficient Genome Modifications Mediated by Crispr/Cas9 in *Drosophila*," Genetics, 2013, vol. 195, No. 1, pp. 289-291, and Supporting Information.
Zolkiewska, "ADAM Proteases: Ligand Processing and Modulation of the Notch Pathway," Cell Mol Life Sci., 2008, pp. 2056-2068, vol. 65, No. 13.
Freitas et al., "Mechanisms and Signals for the Nuclear Import of Proteins," Current Genomics, 2009, pp. 550-557, vol. 10, No. 8.
Gaj et al., "Targeted gene knockout by direct delivery of zinc-finger nuclease proteins," Nature Methods, 2012, pp. 805-809, vol. 9, No. 8.
Gaj et al., "ZFN, TALEN, and CRISPR/Cas-based methods for genome engineering," Trends in Biotechnology, 2013, pp. 397-405, vol. 31, No. 7.
Galli et al., "Effects of DNA Double-Strand and Single-Strand Breaks on Intrachromosomal Recombination Events in Cell-Cycle-Arrested Yeast Cells," Genetics, 1998, pp. 1235-1250, vol. 149.
Garcia-Bustos et al. "Nuclear protein localization," Biochimica et Biophysica Acta, 1991, pp. 83-101, vol. 1071, No. 1.
Garg et al., "Engineering synthetic TAL effectors with orthogonal target sites," Nucleic Acids Research, 2012, pp. 7584-7595, vol. 40, No. 15.
Garneau et al., "The CRISPR/Cas bacterial immune system cleaves bacteriophage and plasmid DNA," Nature, 2010, pp. 67-71, vol. 468.
Golic, "RNA-Guided Nucleases: A New Era for Engineering the Genomes of Model and Nonmodel Organisms," Genetics, 2013, pp. 303-308, vol. 195.
Goncalves et al., "Concerted nicking of donor and chromosomal acceptor DNA promotes homology-directed gene argeting in human cells," Nucleic Acids Research, 2012, pp. 3443-3455, vol. 40, No. 8.
Gratz et al., "Genome Engineering of *Drosophila* with the CRISPR RNA-Guided Cas9 Nuclease," Genetics, 2013, vol. 194, No. 4, pp. 1029-1035, and Supporting Information.
Greenspan et al., "Two Nuclear Location Signals in the Influenza Virus NS1 Nonstructural Protein," Journal of Virology, 1988, pp. 3020-3026, vol. 62, No. 8.
Handel et al., "Versatile and Efficient Genome Editing in Human Cells by Combining Zinc-Finger Nucleases With Adeno-Associated Viral Vectors," Human Gene Therapy, 2012, pp. 321-329, vol. 23, No. 3.
Hicks et al., "Protein Import Into the Nucleus: An Integrated View," Annual Review of Cell and Developmental Biology, 1995, pp. 155-188, vol. 11.
Hockemeyer et al., "Highly efficient gene targeting of expressed and silent genes in human ESCs and iPSCs using zinc finger nucleases," Nature Biotechnology, 2009, pp. 851-857, vol. 27, No. 9.
Imagawa et al., "Two nuclear localization signals are required for nuclear translocation of nuclear factor 1-A," FEBS Letters, 2000, pp. 118-124, vol. 484, No. 2.
Jensen et al.! "An update on targeted gene repair in mammalian cells: methods and mechanisms," Journal of Biomedical Science, 2011, pp. 1-14, vol. 18, No. 10.
Jenuwein et al., "The immunoglobulin µ enhancer core establishes local factor access in nuclear chromatin independent of transcriptional stimulation," Genes & Development, 1993, pp. 2016-2032, vol. 7, No. 10.

(56) References Cited

OTHER PUBLICATIONS

Joung et al., "TALENs: a widely applicable technology for targeted genome editing," Nat Rev Mol Cell Biol., 2013, pp. 49-55, vol. 14, No. 1.
Kalderon et al., "A Short Amino Acid Sequence Able to Specify Nuclear Location," Cell, 1984, pp. 499-509, vol. 39, No. 3.
Kiani et al., "Cas9 gRNA engineering for genome editing, activation and repression," Nature Methods, 2015, pp. 1051-1054, vol. 12, No. 11.
Kondo et al., "Highly Improved Gene Targeting by Germline-Specific Cas9 Expression in *Drosophila*," Genetics, 2013, vol. 195, No. 3, pp. 715-721, with Supporting Information.
Koseki et al., "Factors Governing the Activity In Vivo of Ribozymes Trascribed by RNA Polymerase III," Journal of Virology, 1999, pp. 1868-1877, vol. 73, No. 3.
Kosugi et al., "Six Classes of Nuclear Localization Signals Specific to Different Binding Grooves of Importin α," The Journal of Biological Chemistry, 2009, pp. 478-485, vol. 284, No. 1.
Krauer et al., "Identification of the nuclear localization signals within the Epstein-Barr virus EBNA-6 protein," Journal of General Virology, 2004, pp. 165-172, vol. 85, No. 1.
Lanford et al., "Induction of Nuclear Transport with a Synthetic Peptide Homologous to the SV40 T Antigen Transport Signal," Cell, 1986, pp. 575-582, vol. 46, No. 4.
Lee et al., "RAG Proteins Shepherd Double-Strand Breaks to a Specific Pathway, Suppressing Error-Prone Repair, but RAG Nicking Initiates Homologous Recombination," Cell, 2004, pp. 171-184, vol. 117, No. 2.
Lee et al., "Correction of the ΔF508 Mutation in the Cystic Fibrosis Transmembrane Conductance Regulator Gene by Zinc-Finger Nuclease Homology-Directed Repair," BioResearch Open Access, 2012, pp. 99-108, vol. 1, No. 3.
Lemay et al. "Folding of the Adenine Riboswitch," Chemistry & Biology, 2006, pp. 857-868, vol. 13, No. 8.
Li et al. "Modularly assembled designer TAL effector nucleases for targeted gene knockout and gene replacement in eukaryotes", Nucleic Acids Research, 2011, pp. 6315-6325, vol. 39, No. 14.
Lieber, "The Mechanism of Double-Strand DNA Break Repair by the Nonhomologous DNA End Joining Pathway," Annu Rev Biochem., 2010, pp. 181-211, vol. 79.
Link et al., "Engineering ligand-responsive gene control elements: Lessons learned from natural riboswitches," Gene Therapy, 2009, pp. 1189-1201, vol. 16, No. 10.
Liu et al., "Epstein-Barr Virus DNase Contains Two Nuclear Localization Signals, Which Are Different in Sensitivity to the Hydrophobic Regions," Virology, 1998, pp. 62-73, vol. 247.
Los et al., "Halotag™ Technology: Cell Imaging and Protein Analysis," Cell Notes, 2006, pp. 10-14, vol. 14.
Luo et al., "Multiple Nuclear Localization Sequences Allow Modulation of 5-Lipoxygenase Nuclear Import," Traffic, 2004, pp. 847-854, vol. 5, No. 11.
Lyssenko et al., "Cognate putative nuclear localization signal effects strong nuclear localization of a GFP reporter and facilitates gene expression studies in Caenorhabditis elegans," BioTechniques, 2007, pp. 596-600, vol. 43, No. 5.
Mahfouz et al., "De novo-engineered transcription activator-like effector (TALE) hybrid nuclease with novel DNA binding specificity creates double-strand breaks," PNAS, 2011, pp. 2623-2628, vol. 108, No. 6.
Marfori et al., "Molecular basis for specificity of nuclear import and prediction of nuclear localization," Biochimica et Biophysica Acta, 2011, pp. 1562-1577, vol. 1813, No. 9.
Marraffini et al., "CRISPR Interference Limits Horizontal Gene Transfer in Staphylococci by Targeting DNA," Science, 2008, pp. 1843-1845, vol. 322, No. 5909.
McCall et al., "Probes for chromatin accessibility in the *Drosophila bithorax* complex respond differently to Polycomb-mediated repression," The EMBO Journal, 1996, pp. 569-580, vol. 15, No. 3.
Mei et al., "Recent Progress in CRISPR/Cas9 Technology," Journal of Genetics and Genomics, 2016, pp. 63-75, vol. 43, No. 2.
Metzger et al., "Single-strand nicks induce homologous recombination with less toxicity than double-strand breaks using an AAV vector template," Nucleic Acids Research, 2011, pp. 926-935, vol. 39, No. 3.
Miller et al., "A Tale nuclease architecture for efficient genome editing," Nature Biotechnology, 2011, pp. 143-148, vol. 29, No. 2.
Morin et al., "Nuclear Localization of the Adenovirus DNA-Binding Protein: Requirement for Two Signals and Complementation during Viral Infection," Molecular and Cellular Biology, 1989, pp. 4372-4380, vol. 9, No. 10.
Mussolino et al., "A novel TALE nuclease scaffold enables high genome editing activity in combination with low toxicity," Nucleic Acids Research, 2011, pp. 9283-9293, vol. 39, No. 21.
Mussolino et al., "TALE nucleases: tailored genome engineering made easy," Current Opinion in Biotechnology, 2012, pp. 644-650, vol. 23.
Aguirre et al., "Genomic Copy Numner Dictates a Gene-Independent Cell Response to CRISPR/Cas9 Targeting," Cancer Discovery, 2016, pp. 915-929, vol. 6.
Agus et al., "Modulation of Cardiac Ion Channels by Magnesium," Annu. Rev. Physiol., 1991, pp. 299-307, vol. 53.
Alberts et al., Molecular Biology of the Cell, 3rd Edition, Garland Publishing 1994, Chapter 11, p. 508, Table 11-1.
Brieger et al., "C-Terminal Fluorescent Labeling Impairs Functionality of DNA Mismatch Repair Proteins," PLoS ONE, 2012, e31863, pp. 1-8, vol. 7, No. 2.
Brothers et al., "Unexpected Effects of Epitope and Chimeric Tags on Gonadotropin-Releasing Hormone Receptors: Implications for Understanding the Molecular Etiology of Hypogonadotropic Hypogonadism," The Journal of Clinical Endocrinology & Metabolism, 2003, pp. 6107-6112, vol. 88, No. 12.
Cady et al., "The CRISPR/Cas Adaptive Immune System of Pseudomonas aeruginosa Mediates Resistance to Naturally Occurring and Engineered Phages," Journal of Bacteriology, 2012, pp. 5728-5738, vol. 194, No. 21.
Chiba et al., "Endogenous Telomerase Reverse Transcriptase N-Terminal Tagging Affects Human Telomerase Function at Telomeres In Vivo," Molecular and Cellular Biology, 2017, e00541-16, pp. 1-18, vol. 37, No. 3.
Corkey et al., "Regulation of Free and Bound Magnesium in Rat Hepatocytes and Isolated Mitochondria," The Journal of Biological Chemistry, 1986, pp. 2567-2574, vol. 261, No. 6.
DeKelver et al., "Functional genomics, proteomics, and regulatory DNA analysis in isogenic settings using zinc finger nuclease-driven transgenesis into a safe harbor locus in the human genome," Genome Research, 2010, pp. 1133-1142, vol. 20.
Elbashir et al., "Duplexes of 21-nucleotide RNAs mediate RNA interference in cultured mammalian cells," Nature, 2001, pp. 494-498, vol. 411.
Ellis, "Macromolecular crowding: obvious but underappreciated," TRENDS in Biochemical Sciences, 2001, pp. 597-604, vol. 26, No. 10.
Goldberg, "Protein degradation and protection against misfolded or damaged proteins," Nature, 2003, pp. 895-899, vol. 426.
Guo et al., "Group II Introns Designed to Insert into Therapeutically Relevant DNA Target Sites in Human Cells," Science, 2000, pp. 452-457, vol. 289.
Hocine et al., "RNA Processing and Export," Cold Spring Harb Perspect Biol, 2010; 2:a000752, pp. 1-20.
Hockemeyer et al., "Genetic engineering of human pluripotent cells using TALE nucleases," Nature Biotechnology, 2011, pp. 731-734, vol. 29, No. 8.
Huang et al., "Sensitivity and selectivity of the DNA damage sensor responsible for activating p53-dependent G1 arrest," PNAS, 1996, pp. 4827-4832, vol. 93.
Ihry et al., "P53 toxicity is a hurdle to CRISPR/CAS9 screening and engineering in human pluripotent stem cells," pp. 1-23, and 28 pgs. of Supplemental Information, doi:https://doi.org/10.1101/168443, Jul. 2017.
Jiang et al., "Successful Transient Expression of Cas9 and Single Guide RNA Genes in Chlamydomonas reinhardtii," Eukaryotic Cell, 2014, pp. 1465-1469, vol. 13, No. 11.

(56) References Cited

OTHER PUBLICATIONS

Kadonaga, "Regulation of RNA Polymerase II Transcription by Sequence-Specific DNA Binding Factors," Cell, 2004, pp. 247-257, vol. 116.

Karberg et al., "Group II introns as controllable gene targeting vectors for genetic manipulation of bacteria," Nature Biotechnology, 2001, pp. 1162-1167, vol. 19.

Karpala et al., "Immune responses to dsRNA: Implications for gene silencing technologies," Immunology and Cell Biology, 2005, pp. 211-216, vol. 83.

Khanna et al., "DNA double-strand breaks: signaling, repair and the cancer connection," Nature Genetics, 2001, pp. 247-254, vol. 27.

Kimchi-Sarfaty et al., "A "Silent" Polymorphism in the MDR1 Gene Changes Substrate Specificity," Science, 2007, pp. 525-528, vol. 315.

Lim et al., "Ribozyme suppression of endogenous thyroid hormone receptor activity in Xenopus laevis cells," Nucleic Acids Research, 2002, pp. 3490-3496, vol. 30, No. 15.

Link et al., "Engineering ligand-responsive gene-control elements: lessons learned from natural riboswitches," Gene Therapy, 2009, pp. 1189-1201, vol. 16.

London, "Methods for Measurement of Intracellular Magnesium: NMR and Fluorescence," Annu. Rev. Physiol., 1991, pp. 241-258, vol. 53.

Mertens et al., "Gene optimization mechanisms: A multi-gene study reveals a high success rate of full-length human proteins expressed in *Escherichia coli*," Protein Science, 2010, pp. 1312-1326, vol. 19.

Mak et al., "The Crystal Structure of TAL Effector PthXo1 Bound to Its DNA Target," Science, 2012, pp. 716-719, vol. 335.

Mandal et al., "Gene Regulation by Riboswitches," Nature Reviews, Molecular Cell Biology, 2004, pp. 451-463, vol. 5.

Martin et al., "Introns and the origin of nucleus-cytosol compartmentalization," Nature, 2006, pp. 41-45, vol. 440.

Mauro et al., "A critical analysis of codon optimization in human therapeutics," Trends in Molecular Medicine, 2014, pp. 604-613, vol. 20, No. 11.

Minton, "How can biochemical reactions within cells differ from those in test tubes?," Journal of Cell Science, 2006, pp. 2863-2869, vol. 119, No. 14.

Nishimasu et al., "Crystal Structure of Cas9 in Complex with Guide RNA and Target DNA," Cell, 2014, pp. 935-949, vol. 156, No. 5, and Supplemental Information, pp. S1-S8.

Pavletich et al., "Zinc Finger-DNA Recognition: Crystal Structure of a Zif268-DNA Complex at 2.1 Å," Science,1991, pp. 809-817, vol. 252.

Pyle, "Ribozymes: A Distinct Class of Metalloenzymes," Science, 1993, pp. 709-714, vol. 261.

Semenova et al., "Interference by clustered regularly interspaced short palindromic repeat (CRISPR) RNA is governed by a seed sequence," PNAS, 2011, pp. 10098-10103, vol. 108, No. 25.

Turner et al., "Carboxyl-terminal Vesicular Stomatitis Virus G Protein-tagged Intestinal Na+-dependent Glucose Cotransporter (SGLT1): Maintenance of Surface Expression and Global Transport Function With Selective Perturbation of Transport Kinetics and Polarized Expression," The Journal of Biological Chemistry, 1996, pp. 7738-7744, vol. 271, No. 13.

Urnov et al., "Chromatin remodeling and transcriptional activation: the cast (in order of appearance)," Oncogene, 2001, pp. 2991-3006, vol. 20.

Urnov et al., "A Necessary Good: Nuclear Hormone Receptors and Their Chromatin Templates," Molecular Endocrinology, 2001, pp. 1-16, vol. 15, No. 1.

Wah et al. "Structure of FokI has implications for DNA cleavage," PNAS, 1998, pp. 10564-10569, vol. 95.

Wang et al., "Targeted gene addition to a predetermined site in the human genome using a ZFN-based nicking enzyme," Genome Research, 2012, pp. 1316-1326, vol. 22.

Zhong et al., "Targeted and random bacterial gene disruption using a group II intron (targetron) vector containing a retrotransposition-activated selectable marker," Nucleic Acids Research, 2003, pp. 1656-1664, vol. 31, No. 6.

Zhuang et al., "Linear group II intron RNAs can retrohome in eukaryotes and may use nonhomologous end-joining for cDNA ligation," PNAS, 2009, pp. 18189-18194, vol. 106, No. 43.

Office Action from related Canadian Patent Application No. 2,977,152, dated Sep. 20, 2017; 4 pgs.

"Decision on Motions", Patent Interference No. 106,048, *The Broad Institute, Inc., et al. v. The Regents of the University of California, et al.*, Before the Patent Trial and Appeal Board of the United States Patent and Trademark Office, dated Feb. 15, 2017; 51 pgs.

"Brief for Appellants", Appeal No. 2017-1907, *Regents of the University of California, et al. v. The Broad Institute, Inc., et al.*, United States Court of Appeals for the Federal Circuit, Appeal from the Patent Trial and Appeal Board of the United States Patent and Trademark Office in Interference No. 106,048, dated Jul. 25, 2017; 134 pgs.

"Brief for Appellees", Appeal No. 2017-1907, *Regents of the University of California, et al. v. The Broad Institute, Inc., et al.*, United States Court of Appeals for the Federal Circuit, Appeal from the Patent Trial and Appeal Board of the United States Patent and Trademark Office in Interference No. 106,048, dated Oct. 25, 2017; 80 pgs.

Aagaard et al., "RNAi therapeutics: Principles, prospects and challenges", Advanced Drug Delivery Reviews, 2007, pp. 75-86, vol. 59.

Aguilera et al., "Systemic in vivo distribution of activatable cell penetrating peptides is superior to cell penetrating peptides", Integr. Biol. (Camb.), 2009, pp. 371-381, vol. 1, Nos. 5-6.

Ahuja et al., "SV40 large T antigen targets multiple cellular pathways to elicit cellular transformation", Oncogene, 2005, pp. 7729-7745, vol. 24.

Akopian et al., "Chimeric recombinases with designed DNA sequence recognition", PNAS, 2003, pp. 8688-8691, vol. 100, No. 15.

Anders et al., "Structural basis of PAM-dependent target DNA recognition by the Cas9 endonuclease", Nature, 2014, pp. 569-573, vol. 513, with Supplemental Information.

Anderson et al., "A simple method for the rapid generation of recombinant adenovirus vectors", Gene Therapy, 2000, pp. 1034-1038, vol. 7.

Aravind et al., "Survey and Summary: Holliday junction resolvases and related nucleases: identification of new families, phyletic distribution and evolutionary trajectories", Nucleic Acids Research, 2000, pp. 3417-3432, vol. 28, No. 18.

Asuri et al., "Directed Evolution of Adeno-associated Virus for Enhanced Gene Delivery and Gene Targeting in Human Pluripotent Stem Cells", Molecular Therapy, 2012, pp. 329-338, vol. 20, No. 2.

Aziz et al., "Transposases are the most abundant, most ubiquitous genes in nature", Nucleic Acids Research, 2010, pp. 4207-4217, vol. 38. No. 13.

Babineau et al., "The FLP Protein of the 2-micron Plasmid of Yeast. Purification of the protein from *Escherichia coli* cells expressing the cloned FLP gene", The Journal of Biological Chemistry, 1985, pp. 12313-12319, vol. 260, No. 22.

Banaszewska et al., "Proprotein Convertase Subtilisin/Kexin Type 9: A New Target Molecule for Gene Therapy", Cellular & Molecular Biology Letters, 2012, pp. 228-239, vol. 17, No. 2.

Barranger et al., "Gene Transfer Approaches to the Lysosomal Storage Disorders", Neurochemical Research, 1999, pp. 601-615, vol. 24, No. 4.

Barrangou et al., "CRISPR-Cas Systems: Prokaryotes Upgrade to Adaptive Immunity", Molecular Cell, 2014, pp. 234-244, vol. 54.

Barras, "Right on Target—A breakthrough in genetic engineering is set to transform biology and medicine", New Scientist, 2014, pp. 1-7, vol. 221, No. 2953.

Beerli et al., "Toward controlling gene expression at will: Specific regulation of the erbB-2/HER-2 promoter by using polydactyl zinc finger proteins constructed from modular building blocks", PNAS, 1998, pp. 14628-14633, vol. 95.

(56) References Cited

OTHER PUBLICATIONS

Behr et al., "Efficient gene transfer into mammalian primary endocrine cells with lipopolyamine-coated DNA", PNAS, 1989, pp. 6982-6986, vol. 86.
Beloglazova et al., "A Novel Family of Sequence-specific Endoribonucleases Associated with the Clustered Regularly Interspaced Short Palindromic Repeats", The Journal of Biological Chemistry, 2008, pp. 20361-20371, vol. 283, No. 29.
Beres et al., "Genome sequence of a serotype M3 strain of group A Streptococcus: Phage-encoded toxins, the high-virulence phenotype, and clone emergence", PNAS, 2002, pp. 10078-10083, vol. 99, No. 15.
Bergemann et al., "Excision of specific DNA-sequences from integrated retroviral vectors via site-specific recombination", Nucleic Acids Research, 1995, pp. 4451-4456, vol. 23, No. 21.
Bhaya et al., "CRISPR-Cas Systems in Bacteria and Archaea: Versatile Small RNAs for Adaptive Defense and Regulation", Annual Review of Genetics, 2011, pp. 273-297, vol. 45.
Biffi et al. "Metachromatic leukodystrophy: an overview of current and prospective treatments", Bone Marrow Transplantation, 2008, pp. S2-S6, vol. 42.
Biffi, "Genetically-Modified Hematopoietic Stem Cells and their Progeny for Widespread and Efficient Protein Delivery to Diseased Sites: The Case of Lysosomal Storage Disorders", Current Gene Therapy, 2012, pp. 381-388, vol. 12, No. 5.
Bikard et al., "CRISPR Interference Can Prevent Natural Transformation and Virulence Acquisition during In Vivo Bacterial Infection", Cell Host & Microbe, 2012, pp. 177-186, vol. 12.
Blancafort et al., "Designing Transcription Factor Architectures for Drug Discovery", Molecular Pharmacology, 2004, pp. 1361-1371, vol. 66, No. 6.
Boch et al., "Xanthomonas AvrBs3 Family-Type III Effectors: Discovery and Function", Annual Review of Phytopathology, 2010, pp. 419-436, vol. 48.
Boehm et al., "One of three nuclear localization signals of maize Activator (Ac) transposase overlaps the DNA-binding domain", The Plant Journal, 1995, pp. 441-451, vol. 7, No. 3.
Bolotin et al., "Clustered regularly interspaced short palindrome repeats (CRISPRs) have spacers of extrachromosomal origin", Microbiology, 2005, pp. 2551-2561, vol. 151.
Bolotin et al., "Complete sequence and comparative genome analysis of the dairy bacterium Streptococcus thermophilus", Nature Biotechnology, 2004, pp. 1554-1558, vol. 22, No. 12.
Briner et al., "Guide RNA Functional Modules Direct Cas9 Activity and Orthogonality", Molecular Cell, 2014, pp. 333-339, vol. 56.
Brisson et al., "A novel T7 RNA polymerase autogene for efficient cytoplasmic expression of target genes", Gene Therapy, 1999, pp. 263-270, vol. 6.
Brodkin et al., "Prediction of distal residue participation in enzyme catalysis", Protein Science, 2015, pp. 762-778, vol. 24.
Brouns et al., "Small CRISPR RNAs Guide Antiviral Defense in Prokaryotes", Science, 2008, pp. 960-964, vol. 321.
Brzostek-Racine et al., "The DNA Damage Response Induces IFN", The Journal of Immunology, 2011, pp. 5336-5345, vol. 187.
Buchholz et al., "Different thermostabilities of FLP and Cre recombinases: implications for applied site-specific recombination", Nucleic Acids Research, 1996, pp. 4256-4262, vol. 24, No. 21.
Buchholz et al., "Improved properties of FLP recombinase evolved by cycling mutagenesis", Nature Biotechnology, 1998, pp. 657-662, vol. 16.
Carroll, "Genome Engineering with Targetable Nucleases", Annual Review of Biochemistry, 2014, pp. 409-439, vol. 83.
Carroll, "Genome Engineering with Zinc-Finger Nucleases", Genetics, 2011, pp. 773-782, vol. 188.
Carte et al., "Cas6 is an endoribonuclease that generates guide RNAs for invader defense in prokaryotes", Genes & Development, 2008, pp. 3489-3496, vol. 22.
Cate et al., "Crystal Structure of a Group I Ribozyme Domain: Principles of RNA Packing", Science, 1996, pp. 1678-1685, vol. 273.
Chaikind et al., "A programmable Cas9-serine recombinase fusion protetin that operates on DNA sequences in mammalian cells", Nucleic Acids Research, 2016, pp. 9758-9770, vol. 44, No. 20.
Chandrasegaran et al., "Origins of Programmable Nucleases for Genome Engineering", Journal of Molecular Biology, 2016, pp. 963-989, vol. 428.
Meleady and O'Connor, "General Procedures for Cell Culture", Chapter 2 of "Cell Biology a Laboratory Handbook", edited by Julio E. Celis, Third Edition, vol. 1 (2006), pp. 13-20.
Huser et al., "Integration Preferences of Wildtype AAV-2 for Consensus Rep-Binding Sites at Numerous Loci in the Human Genome", PLoS Pathogens, 2010, e1000985, pp. 1-14, vol. 6, No. 7.
Judgment of the Court (Grand Chamber), Court of Justice of the European Union Decision in case C-34/10, dated Oct. 18, 2011; 12 pgs.
EPO Boards of Appeal Decision, Case No. T2488/12, dated Jan. 26, 2016; 21 pgs.
Jasin et al., "Commentary: Targeted transgenesis", PNAS, 1996, pp. 8804-8808, vol. 93.
Opposition by HGF Limited against EP 2 800 811 (EP 13793997.1), filed Feb. 9, 2018; 69 pgs.
Opposition by Sandra Pohlman against European Patent No. EP 2 800 811 B1 (European Appl. No. 13 793 997.1), filed Mar. 15, 2013; 84 pgs.
Opposition by Glyn John Truscott against European Patent No. EP 2800811B1 (Application No. 13793997.1), filed Feb. 9, 2018; 43 pgs.
Declaration of Professor Matthias W. Hentze, dated Feb. 1, 2018, filed by Sandra Pohlman in opposition against EP2800811; pp. 1-26.
Grounds of Opposition by Onno Griebling against European Patent No. EP 2 800 811—application 13793997.1, filed Feb. 9, 2018; 33 pgs.
Grounds of Opposition by TL Brand & Co Ltd, against European Patent No. EP 2800811, Application No. 13793997.1, filed Feb. 7, 2018; 23 pgs.
Opposition by Jones Day, against European Patent No. EP 2 800 811 (13793997.1), filed Feb. 9, 2018; 61 pgs.
Opposition by Allergen, International Ltd., against European Patent No. EP 2 800 811, filed Feb. 11, 2018; 41 pgs.
Declaration of Technical Expert, Paul Simons, PhD, dated Dec. 22, 2015; 76 pgs.
Declaration of Bryan R. Cullen, Ph.D., dated Jun. 24, 2016; 16 pgs.
United States Court of Appeals for the Federal Circuit, Case No. 2017-1907, Appeal from the United States Patent and Trademark Office, Patent Trial and Appeal Board, regarding Interference No. 106,048 (DK), Decision dated: Sep. 10, 2018; 16 pgs.
Opposition Division Preliminary Opinion for EP2784162 (Application No. 14 170 383.5), dated Jun. 5, 2018; 15 pgs.
Opposition Division Preliminary Opinion for EP2896697 (Application No. 15 154 539.9), dated Jun. 1, 2018; 14 pgs.
Richard et al., "Cell-penetrating Peptides—A Reevaluation of the Mechanism of Cellular Uptake", The Journal of Biological Chemistry, 2003, pp. 585-590, vol. 278, No. 1.
Holt et al., "Human hematopoietic stem/progenitor cells modified by zinc-finger nucleases targeted to CCR5 control HIV-1 in vivo", Nature Biotechnology, 2010, pp. 839-847, vol. 28, No. 8.
Deeks et al., "Can HIV be cured with stem cell therapy?", Nature Biotechnology 2010, pp. 807-810, vol. 28, No. 8.
Yanez et al., "Therapeutic gene targeting", Gene Therapy, 1998, pp. 149-159, vol. 5.
Radecke et al., "Zinc-finger Nuclease-induced Gene Repair With Oligodeoxynucleotides: Wanted and Unwanted Target Locus Modifications", Molecular Therapy, 2010, pp. 743-753, vol. 18, No. 4.
Petek et al., "Frequent Endonuclease Cleavage at Off-target Locations In Vivo", Molecular Therapy, 2010, pp. 983-986, vol. 18, No. 5.
Beumer et al., "Efficient Gene Targeting in Drosophila With Zinc-Finger Nucleases", Genetics, 2006, pp. 2391-2403, vol. 172.

(56) References Cited

OTHER PUBLICATIONS

Straimer et al., "Site-specific genome editing in Plasmodium falciparum using engineered zinc-finger nucleases", Nature Methods, 2012, pp. 993-998, vol. 9, No. 10.
Wikipedia—Annual Reviews (publisher), Mar. 27, 2019; pp. 1-4.
Chen et al., "A Facile System for Encoding Unnatural Amino Acids in Mammalian Cells", Angew Chem Int Ed Engl., 2009, pp. 4052-4055, vol. 48, No. 22.
Chen et al., "Dynamic Imaging of Genomic Loci in Living Human Cells by an Optimized CRISPR/Cas System", Cell, 2013, pp. 1479-1491, vol. 155.
Chen et al., "Genome-wide CRISPR Screen in a Mouse Model of Tumor Growth and Metastasis", Cell, 2015, pp. 1-15, vol. 160.
Chen et al., "A critical stem-loop structure in the CR4-CR5 domain of mammalian telomerase RNA", Nucleic Acids Research, 2002, pp. 592-597, vol. 30, No. 2.
Choudhury et al., "CRISPR-dCas9 mediated TET1 targeting for selective DNA demethylation at BRCA1 promoter", Oncotarget, 2016, pp. 46545-46556, vol. 7, No. 29.
Cong et al., "Comprehensive Interrogation of Natural TALE DNA Binding Modules and Transcriptional Repressor Domains", Nature Communications, 2013, pp. 1-13, vol. 3.
Coppoolse et al., "Cre recombinase expression can result in phenotypic aberrations in plants", Plant Molecular Biology, 2003, pp. 263-279, vol. 51.
Corrigan-Curay et al., "Genome Editing Technologies: Defining a Path to Clinic", Molecular Therapy, 2015, pp. 796-806, vol. 23, No. 5.
Cost et al., "BAK and BAX Deletion Using Zinc-Finger Nucleases Yields Apoptosis-Resistant CHO Cells", Biotechnology and Bioengineering, 2010, pp. 330-340, vol. 105, No. 2.
Costa et al., "Rules for RNA recognition of GNRA tetraloops deduced by in vitro selection: comparison with in vivo evolution", The EMBO Journal, 1997, pp. 3289-3302, vol. 16, No. 11.
Courtin et al., "Interactions between microorganisms in a simple ecosystem: yogurt bacteria as a study model", Lait, 2004, pp. 125-134, vol. 84.
Cox, "The FLP protein of the yeast 2-μm plasmid: Expression of a eukaryotic genetic recombination system in *Escherichia coli*", PNAS, 1983, pp. 4223-4227, vol. 80.
Cradick et al., "ZFN-Site searches genomes for zinc finger nuclease target sites and off-target sites", BMC Bioinformatics, 2011, pp. 1-9, vol. 12.
Crasto et al., "LINKER: a program to generate linker sequences for fusion proteins", Protein Engineering, 2000, pp. 309-312, vol. 13, No. 5.
Dagnino et al., "Molecular Diagnosis of Analbuminemia: A New Case Caused by a Nonsense Mutation in the Albumin Gene", International Journal of Molecular Sciences, 2011, pp. 7314-7322, vol. 12.
Daigle et al., "Nuclear pore complexes form immobile networks and have a very low turnover in live mammalian cells", The Journal of Cell Biology, 2001, pp. 71-84, vol. 154, No. 1.
Dang et al., "Identification of the Human c-myc Protein Nuclear Translocation Signal", Molecular and Cellular Biology, 1988, pp. 4048-4054, vol. 8, No. 10.
Danielsson et al., "Thermodynamics of protein destabilization in live cells", PNAS, 2015, pp. 12402-12407, vol. 112, No. 40.
Datsenko et al., "Molecular memory of prior infections activates the CRISPR/Cas adaptive bacterial immunity system", Nature Communications, 2012, pp. 1-7, vol. 3.
Davies et al., "Site Specific Mutation of the Zic2 Locus by Microinjection of TALEN mRNA in Mouse CD1, C3H and C57BL/6J Oocytes", PLOS ONE, 2013, e60216, pp. 1-7, vol. 8, No. 3.
Davis et al., "Zinc Finger Nucleases as tools to understand and treat human diseases", BMC Medicine, 2010, pp. 1-11, vol. 8.
Davis et al., "Role of metal ions in the tetraloop-receptor complex as analyzed by NMR", RNA, 2007, pp. 76-86, vol. 13, No. 1.

Davis et al., "Zinc Finger Nucleases for Genome Editing", Genetic Engineering & Biotechnology News, Jul. 2010, pp. 40, vol. 30, No. 13.
Day et al., The fluorescent protein palette: tools for cellular imaging, Chem Soc Rev., 2009, pp. 2887-2921, vol. 38, No. 10.
Deveau et al., "CRISPR/Cas System and Its Role in Phage-Bacteria Interactions", Annual Review of Microbiology, 2010, pp. 475-493, vol. 64.
Deveau et al., "Phage Response to CRISPR-Encoded Resistance in *Streptococcus thermophilus*", Journal of Bacteriology, 2008, pp. 1390-1400, vol. 190, No. 4.
Ding et al., "Enhanced Efficiency of Human Pluripotent Stem Cell Genome Editing through Replacing TALENs with CRISPRs", Cell Stem Cell, 2013, pp. 393-394, vol. 12.
Drag et al., "Critical Review—DeSUMOylating Enzymes—SENPs", IUBMB Life, 2008, pp. 734-742, vol. 60, No. 11.
Dulon et al., "The bacterial Neo gene confers neomycin resistance to mammalian cochlear hair cells", NeuroReport, 1999, pp. 1189-1193, vol. 10, No. 6.
Dykxhoorn et al., "Killing the Messenger: Short RNAS That Silence Gene Expression", Molecular Cell Biology, 2003, pp. 457-467, vol. 4.
Ellis et al., "Zinc-finger nuclease-mediated gene correction using single AAV vector transduction and enhancement by Food and Drug Administration-approved drugs", Gene Therapy, 2013, pp. 35-42, vol. 20.
Enyeart et al., "Biotechnological applications of mobile group II introns and their reverse transcriptases: gene targeting, RNA-seq, and non-coding RNA analysis", Mobile DNA, 2014, pp. 1-19, vol. 5.
Esvelt et al., "Orthogonal Cas9 Proteins for RNA-Guided Gene Regulation and Editing", Nature Methods, 2013, pp. 1116-1121, vol. 10, No. 11.
Fatholahi et al., "Relationship between Total and Free Cellular Mg2+ during Metabolic Stimulation of Rat Cardiac Myocytes and Perfused Hearts", Archives of Biochemistry and Biophysics, 2000, pp. 395-401, vol. 374, No. 2.
Fechheimer et al., "Transfection of mammalian cells with plasmid DNA by scrape loading and sonication loading", PNAS, 1987, pp. 8463-8467, vol. 84.
Ferre-D'Amare et al., "A General Module for RNA Crystallization", Journal of Molecular Biology, 1998, pp. 621-631, vol. 279.
Ferretti et al., "Complete genome sequence of an M1 strain of *Streptococcus pyogenes*", PNAS, 2001, pp. 4658-4663, vol. 98, No. 8.
Fonfara et al., "Phylogeny of Cas9 determines functional exchangeability of dual-RNA and Cas9 among orthologous type II CRISPR-Cas systems", Nucleic Acids Research, 2014, pp. 2577-2590, vol. 42, No. 4.
Foo et al., "Mutation of outer-shell residues modulates metal ion co-ordination strength in a metalloenzyme", Biochemical Journal, 2010, pp. 313-321, vol. 429, with Supplementary Data.
Forster et al., "External Guide Sequences for an RNA Enzyme", Science, 1990, pp. 783-786, vol. 249.
Freier et al., "Improved free-energy parameters for predictions of RNA duplex stability", PNAS, 1986, pp. 9373-9377, vol. 83.
Friedland et al., "Characterization of *Staphylococcus aureus* Cas9: a smaller Cas9 for all-in-one adeno-associated virus delivery and paired nickase applications", Genome Biology, 2015, pp. 1-10, vol. 16.
Fritz et al., "Direct Vpr-Vpr Interaction in Cells monitored by two Photon Fluorescence Correlation Spectroscopy Fluorescence and Lifetime Imaging", Retrovirology, 2008, pp. 1-17, vol. 5.
Fu et al., "Improving CRISPR-Cas nuclease specificity using truncated guide RNAs", Nature Biotechnology, 2014, pp. 279-284, vol. 32, No. 3.
Fuerst et al., "Use of a Hybrid Vaccinia Virus-T7 RNA Polymerase System for Expression of Target Genes", Molecular and Cellular Biology, 1987, pp. 2538-2544, vol. 7, No. 7.
Watson et al., "Transferring Genes into Mammalian Cells", Recombinant DNA, 1992, Second Edition, Chapter 12, pp. 213-234.

(56) References Cited

OTHER PUBLICATIONS

Puchta et al., "Two different but related mechanisms are used in plants for the repair of genomic double-strand breaks by homologous recombination", PNAS, 1996, pp. 5055-5060, vol. 93.
Townsend et al., "High frequency modification of plant genes using engineered zinc finger nucleases", Nature, 2009, pp. 442-445, vol. 459.
Townsend et al., "High frequency modification of plant genes using engineered zinc finger nucleases", Nature, 2009, Supplementary Figures and Tables; 12 pgs.
Tzfira et al., "Genome modifications in plant cells by custom-made restriction enzymes", Plant Biotechnology Journal, 2012, pp. 373-389, vol. 10.
Zhang et al., "Transcription Activator-Like Effector Nucleases Enable Efficient Plant Genome Engineering", Plant Physiology, 2013, pp. 20-27, vol. 161.
Zhang et al., "Transcription Activator-Like Effector Nucleases Enable Efficient Plant Genome Engineering", Plant Physiology, 2013, Supplementary materials; 7 pgs.
Sadelain et al., "Safe harbours for the integration of new DNA in the human genome", Nature Reviews/Cancer, 2012, pp. 51-58, vol. 12.
Schiel et al., "Fluorescent tagging of an endogenous gene by homology-directed repair using Dharmacon Edit-R CRISPR-Cas9 reagents", GE Healthcare; 5 pgs.—cited by Opponent BASF SE on Jun. 19, 2018, in Opposition to European Patent No. EP 3138910.
ROMPP (Georg Thieme Verlag KG) entry for the term "in vivo" (Status: Apr. 2009).
ROMPP (Georg Thieme Verlag KG) entry for the term "in vitro" (Status: Apr. 2009).
Bassett et al., "CRISPR/Cas9 and Genome Editing in *Drosophila*", Journal of Genetics and Genomics, 2014, pp. 7-19, vol. 41.
European Search Opinion related to Application No. 13 849 670.8, dated Mar. 14, 2017; 6 pgs.
Claim basis document as filed Aug. 11, 2016; 1 page.
Annotated amended claims as filed Apr. 11, 2017; 3 pgs.
U.S. Appl. No. 61/765,576, filed Feb. 15, 2013; 143 pgs.
Reyon et al., "FLASH assembly of TALENs for high-throughput genome editing", Nature Biotechnology, 2012, pp. 460-465, vol. 30.
Zambrowicz et al., "Disruption of overlapping transcripts in the ROSA ßgeo 26 gene trap strain leads to widespread expression of ß-galastosidase in mouse embryos and hematopoietic cells", PNAS, 1997, pp. 3789-3794, vol. 94.
Expert Opinion of Professor Marco Herold (In the matter of European Patent EP 3 138 910), dated Jun. 15, 2018; 27 pgs.
Curriculum Vitae of Professor Marco Herold; filed with Expert Opinion on Jun. 15, 2018; 9 pgs.
Liao et al., "In Vivo Target Gene Activation via CRISPR/Cas9-Mediated Trans-epigenetic Modulation", Cell, 2017, pp. 1495-1507, vol. 171, and Supplemental materials.
Yao et al., "Homology-mediated end joining-based targeted integration using CRISPR/Cas9", Cell Research, 2017, pp. 801-814, vol. 27.
Wikipedia entry for "Genome editing", dated Sep. 6, 2012; 7 pgs.
Lewin et al., "Nuclear localization sequences target proteins to the nucleus", textbook excerpt from Cells (2007), Chapter 5; p. 224.
Kouranova et al., "CRISPRs for Optimal Targeting: Delivery of CRISPR Components as DNA, RNA, and Protein into Cultured Cells and Single-Cell Embryos", Human Gene Therapy, 2016, pp. 464-475, vol. 27, No. 6.
Wikipedia entry for "Transcription activator-like effector nuclease", dated Nov. 16, 2012; 5 pgs.
Le Provost et al., "Zinc finger nuclease technology heralds a new era in mammalian transgenesis", Trends in Biotechnology, 2009, pp. 134-141, vol. 28, No. 3.
Gantz et al., "Targeted Genomic Integration of a Selectable Floxed Dual Fluorescence Reporter in Human Embryonic Stem Cells", PLoS ONE, 2012, e46971, pp. 1-9, vol. 7, No. 10.
Hockemeyer et al., "Gene Targeting in Human Pluripotent Cells", Cold Spring Harbor Symposia on Quantitative Biology, 2010, pp. 201-209, vol. 75.
Hu et al., "Comparison of Various Nuclear Localization Signal-Fused Cas9 Proteins and Cas9 mRNA for Genome Editing in Zebrafish", Genes/Genomes/Genetics, 2018, pp. 823-831, vol. 8.
Altshuler et al., National Institute of Diabetes and Digestive and Kidney Diseases, NIH, submitted by the Broad Institute (Oct. 8, 2012); 108 pgs.
National Institute of General Medical Sciences/"Freedom of Information Act" for obtaining an NIH research grant, downloaded Jun. 11, 2015 from http://www.nigms.nih.gov/Pages/FOIA.aspx; 2 pgs.
NIH RePORTER Project Information for research grant, downloaded Jun. 11, 2015 from http://projectreporter.nih.gov/project_info_details.cfm?aid=84122 . . . 2 pgs.
Evidence of response from NIH RePORT Support Team, dated Oct 20, 2015; 1 page.
Ramachandra et al., "Efficient recombinase-mediated cassette exchange at the AAVS1 locus in human embryonic stem cells using baculoviral vectors", Nucleic Acids Research, 2011, e107, pp. 1-13, vol. 39, No. 16.
Westra et al., "The CRISPRs, They Are A-Changin': How Prokaryotes Generate Adaptive Immunity", Annual Review of Genetics, 2012, pp. 311-339, vol. 46.
Fineran et al., "Memory of viral infections by CRISPR-Cas adaptive immune systems: Acquisition of new information," Virology, 2012, pp. 202-209, vol. 434.
Declaration of Professor Paula Cannon, In the Matter of Oppositions against European Patent. No. 3138910, Patentee: Sigma-Aldrich Co. LLC; dated Mar. 27, 2019; 31 pgs.
Mojica and Garrett, "Discovery and Seminal Developments in the CRISPR Field", Chapter 1 of "CRISPR-Cas Systems: RNA-mediated Adaptive Immunity in Bacteria and Archaea", Pub. Springer Sciences & Business Media (2012), eds. Barrangou & van der Oost; pp. 1-31.
Pourcel and Drevet, "Occurrence, Diversity of CRISPR-Cas Systems and Genotyping Implications", Chapter 2 of "CRISPR-Cas Systems: RNA-mediated Adaptive Immunity in Bacteria and Archaea", Pub. Springer Sciences & Business Media (2012), eds. Barrangou & van der Oost; pp. 33-59.
Makarova and Koonin, "Evolution and Classification of CRISPR-Cas Systems and Cas Protein Families", Chapter 3 of "CRISPR-Cas Systems: RNA-mediated Adaptive Immunity in Bacteria and Archaea", Pub. Springer Sciences & Business Media (2012), eds. Barrangou & van der Oost; pp. 61-91.
Charpentier et al., "crRNA Biogenesis", Chapter 5 of "CRISPR-Cas Systems: RNA-mediated Adaptive Immunity in Bacteria and Archaea", Pub. Springer Sciences & Business Media (2012), eds. Barrangou & van der Oost; pp. 115-144.
Dupuis and Moineau, "Type II: *Streptococcus thermophilus*", Chapter 7 of "CRISPR-Cas Systems: RNA-mediated Adaptive Immunity in Bacteria and Archaea", Pub. Springer Sciences & Business Media (2012), eds. Barrangou & van der Oost; pp. 171-200.
Horvath et al., "Applications of the Versatile CRISPR-Cas Systems", Chapter 11 of "CRISPR-Cas Systems: RNA-mediated Adaptive Immunity in Bacteria and Archaea", Pub. Springer Sciences & Business Media (2012), eds. Barrangou & van der Oost; pp. 267-286.
Extract from "Henderson's Dictionary of Biological Terms", 11th edition, edited by Eleanor Lawrence, Pub. Longman Group Limited (1995); 3 pgs.
Addgene, Plasmid #43945, p3s-Cas9HC, Depositing Lab: Jin-Soo Kim, https://www.addgene.org/43945/, printed as pp. 1/4-4/4 on Mar. 23, 2018.
Agilent Technologies, Instruction Manual for pSG5 Vector (Catalog #216201), Revision A, 2008; 9 pgs.(Year: 2008).
Alexeyev et al., "a-Complementation-Enabled T7 Expression Vectors and Their Use for the Expression of Recombinant Polypeptides for Protein Transduction Experiments", Methods in Molecular Biology, 2004, pp. 91-100, vol. 267.
Deltcheva et al., "CRISPR RNA maturation by trans-encoded small RNA and host factor RNase III", Nature, 2011, pp. 602-607, vol. 471, including pp. 1/2-2/2 of Online Methods, pp. 1/35-35/35 of Supplementary Figures, and pp. 1/22-22/22 of Supplementary Tables.
European Search Report from European Application No. 18156734.8, dated May 16, 2018; 17 pgs.

(56) References Cited

OTHER PUBLICATIONS

European Search Report from European Application No. 18160519.7, dated May 16, 2018; 17 pgs.
Gao et al., "UpGene: Application of a Web-Based DNA Codon Optimization Algorithm", Biotechnology Progress, 2004, pp. 443-448, vol. 20, No. 2.
Gupta et al., "Zinc finger protein-dependent and -independent contributions to the in vivo off-target activity of zinc finger nucleases", Nucleic Acids Research, 2011, pp. 381-392, vol. 39, No. 1.
Lacoste et al., "An Efficient and Reversible Transposable System for Gene Delivery and Lineage-Specific Differentiation in Human Embryonic Stem Cells", Cell Stem Cell, 2009, pp. 332-342, vol. 5, including Supplemental Data.
Lukavsky et al., "Large-scale preparation and purification of polyacrylamide-free RNA oligonucleotides", RNA, 2004, pp. 889-893, vol. 10, No. 5.
Notice of Opposition to Australian Patent Application No. 2013355214, filed by Grant Fisher on Sep. 15, 2017; Statement of Grounds and Particulars in Support of Opposition filed Dec. 15, 2017—Withdrawn May 23, 2018.
Notice of Opposition to Australian Patent Application No. 2013355214, filed by Innovation Equity Pty Ltd on Sep. 15, 2017—Withdrawn Nov. 6, 2017.
Notice of Opposition to Australian Patent Application No. 2013355214, filed by Jones Tulloch Pty Ltd on Sep. 15, 2017—Withdrawn Oct. 30, 2017.
Notice of Opposition to Australian Patent Application No. 2013355214, filed by Steven Borovec on Sep. 15, 2017—Dismissed by APO on Jan. 11, 2018.
Office Action from European Patent Application No. 16183724.0, dated Nov. 29, 2017; 5 pgs.
Office Action from European Patent Application No. 16183725.7, dated Dec. 15, 2017; 7 pgs.
Office Action from Japanese Patent Application No. 2017-115672, dated Jan. 9, 2018; 9 pgs.
Office Action from Canadian Patent Application No. 2,977,152, dated Jan. 10, 2018; 4 pgs.
Office Action from U.S. Appl. No. 15/188,911, dated Feb. 8, 2018; 118 pgs.
Office Action from U.S. Appl. No. 15/456,204, dated Feb. 13, 2018; 108 pgs.
Office Action from U.S. Appl. No. 15/188,931, dated Mar. 22, 2018; 60 pgs.
Office Action from U.S. Appl. No. 15/188,927, dated Mar. 22, 2018; 47 pgs.
Office Action from U.S. Appl. No. 15/188,933, dated Apr. 12, 2018; 33 pgs.
Office Action and Search Report from Canadian Patent Application No. 2,977,152, dated May 2, 2018; 5 pgs.
Office Action from European Patent Application No. 16183725.7, dated Jun. 22, 2018; 3 pgs.
Office Action from European Patent Application No. 16183724.0, dated Jun. 25, 2018; 3 pgs.
Office Action from European Patent Application No. 13859964.2, dated Jun. 26, 2018; 4 pgs.
Office Action from Israel Patent Application No. 257178, dated Jul. 31, 2018; 5 pgs.
Office Action and Search Report from Canadian Patent Application No. 2,977,152, dated Aug. 28, 2018; 5 pgs.
Office Action from Australian Patent Application No. 2018229489, dated Nov. 12, 2018; 2 pgs.
Office Action from Korean Patent Application No. 10-2018-7001934, dated Nov. 20, 2018; 6 pgs.
Office Action from U.S. Appl. No. 15/188,911, dated Dec. 14, 2018; 100 pgs.
Office Action from U.S. Appl. No. 15/456,204, dated Dec. 17, 2018; 95 pgs.
Office Action from Canadian Patent Application No. 2,977,152, dated Jan. 2, 2019; 3 pgs.
Office Action from European Patent Application No. 18156734.8, dated Jan. 17, 2019; 3 pgs.
Office Action from European Patent Application No. 18160519.7, dated Jan. 17, 2019; 3 pgs.
Office Action from U.S. Appl. No. 15/653,136, dated Mar. 7, 2019; 18 pgs.
PcDNA™3.1(+), pcDNA™3.1(−) User Manual, Invitrogen Catalog Nos. V790-20 and V795-20, Version K; Nov. 10, 2010, pp. i-v and 1-17.
Pernstich et al., "Illuminating the reaction pathway of the FokI restriction endonuclease by fluorescence resonance energy transfer", Nucleic Acids Research, 2012, pp. S1203-1213, vol. 40, No. 3.
U.S. Appl. No. 61/716,256, filed Oct. 19, 2012; 275 pgs.
CNLS Mapper Result—report of predicted NLSs in the S. pyogenes Cas9 sequence generated using the online CNLS mapper algorithm (www.nlsmapper.iab.keio.ac.jp), 5 pgs.—cited by Opponent George Schlich on Jun. 20, 2018, in Opposition to European Patent No. EP 3138910.
U.S. Appl. No. 61/835,931, filed Jun. 27, 2013; 298 pgs.
Derossi et al., "Cell Internalization of the Third Helix of the Antennapedia Homeodomain Is Receptor-independent", The Journal of Biological Chemistry, 1996, pp. 18188-18193, vol. 271, No. 30.
Yang et al., "HIV-1 TAT-mediated protein transduction and subcellular localization using novel expression vectors", FEBS Letters, 2002, pp. 36-44, vol. 532.
Extract downloaded from http://ww.addgene.org/vector-database/4288/; 2 pgs.—cited by Opponent Vossius & Partner on Jun. 20, 2018, in Opposition to European Patent No. EP 3138910.
European Publication No. EP 2 800 811 B1, published May 10, 2017; 245 pgs.
Joung et al., "TALENs: a widely applicable technology for targeted genome editing", Nat Rev Mol Cell Biol., 2013, Supplementary information; 15 pgs.
Joung et al., "TALENs: a widely applicable technology for targeted genome editing", Nat Rev Mol Cell Biol., 2013, further supplementary materials; 2 pgs.
Puchta, "The repair of double-strand breaks in plants: mechanisms and consequences for genome evolution", Journal of Experimental Botany, 2005, pp. 1-14, vol. 56, No. 409.
Chapman et al., "Playing the End Game: DNA Double-Strand Break Repair Pathway Choice", Molecular Cell, 2012, pp. 497-510, vol. 47.
Salomon et al., "Capture of genomic and T-DNA sequences during double-strand break repair in somatic plant cells", The EMBO Journal, 1998, pp. 6086-6095, vol. 17, No. 20.
Bibikova et al., "Enhancing Gene Targeting with Designed Zinc Finger Nucleases", Science, 2003, p. 764, vol. 300.
Rudin et al., "Efficient Repair of HO-Induced Chromosomal Breaks in *Saccharomyces cerevisiae* by Recombination between Flanking Homologous Sequences", Molecular and Cellular Biology, 1988, pp. 3918-3928, vol. 8, No. 9.
Rouet et al., "Introduction of Double-Strand Breaks into the Genome of Mouse Cells by Expression of a Rare-Cutting Endonuclease", Molecular and Cellular Biology, 1994, pp. 8096-8106, vol. 14, No. 12.
Carroll et al., "Design, construction and in vitro testing of zinc finger nucleases", Nature Protocols, 2006, pp. 1329-1341, vol. 1, No. 3.
Bedell et al., "In vivo genome editing using a high-efficiency TALEN system", Nature, 2012, pp. 114-118, vol. 491.
Declaration by Dr. Ignacio Anegon, made in relation to EP-B1 3 138 910, dated Jun. 15, 2018; 24 pgs.—filed by Opponent Vossius & Partner on Jun. 20, 2018, in Opposition to European Patent No. EP 3138910.
Cui et al., "Targeted integration in rat and mouse embryos with zinc-finger nucleases", Nature Biotechnology, 2011, pp. 64-67, vol. 29, No. 1.
Maresca et al., "Obligate Ligation-Gated Recombination (ObLiGaRe): Custom-designed nuclease-mediated targeted integration through nonhomologous end joining", Genome Research, 2013, pp. 539-546, vol. 23.

(56) References Cited

OTHER PUBLICATIONS

Laumonier et al., "Lentivirus Mediated HO-1 Gene Transfer Enhances Myogenic Precursor Cell Survival After Autologous Transplantation in Pig", Molecular Therapy, 2008, pp. 404-410, vol. 16, No. 2.

Bizzarri et al., "Fluorescence recovery after photobleaching reveals the biochemistry of nucleocytoplasmic exchange", Anal Bioanal Chem, 2012, pp. 2339-2351, vol. 403.

Souilhol et al., "NAS Transgenic Mouse Line Allows Visualization of Notch Pathway Activity In Vivo", Genesis, 2006, pp. 277-286, vol. 44.

Furutama et al., "Expression of the IP3R1 Promoter-Driven nls-LacZ Transgene in Purkinje Cell Parasagittal Arrays of Developing Mouse Cerebellum", Journal of Neuroscience Research, 2010, pp. 2810-2825, vol. 88.

McConnell et al., "Nuclear and cytoplasmic LIMK1 enhances human breast cancer progression", Molecular Cancer, 2011, pp. 1-13, vol. 10.

Beumer et al., "Efficient gene targeting in *Drosophila* by direct embryo injection with zinc-finger nucleases", PNAS, 2008, pp. 19821-19826, vol. 105, No. 50.

Hodel et al., "Nuclear Localization Signal Receptor Affinity Correlates with in Vivo Localization in *Saccharomyces cerevisiae*", The Journal of Biological Chemistry, 2006, pp. 23545-23556, vol. 281, No. 33.

Miller et al., "Human Gene Targeting by Adeno-Associated Virus Vectors Is Enhanced by DNA Double-Strand Breaks", Molecular and Cellular Biology, 2003, pp. 3550-3557, vol. 23, No. 10.

Chang et al., "Microtubule-based localization of a synaptic calcium-signaling complex is required for left-right neuronal asymmetry in C. elegans", Development, 2011, pp. 3509-3518, vol. 138.

Liang et al., "Homology-directed repair is a major double-strand break repair pathway in mammalian cells", PNAS, 1998, pp. 5172-5177, vol. 95.

Ward et al., "Targeted integration of a rAAV vector into the AAVS1 region", Virology, 2012, pp. 356-366, vol. 433.

Irion et al., "Identification and targeting of the ROSA26 locus in human embryonic stem cells", Nature Biotechnology, 2007, pp. 1477-1482, vol. 25, No. 12.

Minami et al., "Ets Motifs Are Necessary for Endothelial Cell-Specific Expression of a 723-bp Tie-2 Promoter/ Enhancer in Hprt Targeted Transgenic Mice", Arteriosclerosis, Thrombosis, and Vascular Biology, Journal of the American Heart Association, 2003, pp. 2041-2047, vol. 23.

Zhang et al., "Applications of mRNA injections for analyzing cell lineage and asymmetric cell divisions during segmentation in the leech *Helobdella robusta*", Development, 2005, pp. 2103-2113, vol. 132.

U.S. Appl. No. 61/652,086, filed May 25, 2012; 179 pgs.

U.S. Appl. No. 61/717,324, filed Oct. 23, 2012; 20 pgs.

Goldfarb et al., "Importin a: a multipurpose nuclear-transport receptor", TRENDS in Cell Biology, 2004, pp. 505-514, vol. 14, No. 9.

Geurts et al., "Knockout Rats Produced Using Designed Zinc Finger Nucleases", Science, 2009, pp. 1-3, vol. 325.

Tesson et al., "Knockout rats generated by embryo microinjection of TALENs", Nature Biotechnology, 2011, pp. 695-696, vol. 29, No. 8.

Karran, "DNA double strand break repair in mammalian cells", Current Opinion in Genetics & Development, 2000, pp. 144-150, vol. 10.

Remy et al., "Zinc-finger nucleases: a powerful tool for genetic engineering of animals", Transgenic Research, 2010, pp. 363-371, vol. 19.

EP Register extract for WO2013/176772; 1 page, downloaded on Jun. 18, 2018—cited by Opponent Cohausz & Florack on Jun. 20, 2018, in Opposition to European Patent No. EP 3138910.

Screenshot of http://www.nature.com/nprot/journal/v7/n1/full/nprot. 2011.431.html#access showing the publication date of Jan. 5, 2012, of SANJANA reference, Nature Protocols, vol. 7, No. 1.

Alberts et al., Molecular Biology of the Cell, 2002, 4th Ed., pp. 671-676.

PSORT data, downloaded Dec. 31, 2015; 13 pgs.—cited by Opponent HGF Limited on Jun. 13, 2018, in Opposition to European Patent No. EP 3138910.

Lieber et al., "Stable High-Level Gene Expression in Mammalian Cells by T7 Phage RNA Polymerase", Methods in Enzymology, 1993, pp. 47-66, vol. 217.

Lieber et al., "High level gene expression in mammalian cells by a nuclear T7-phage RNA polymerase", Nucleic Acids Research, 1989, pp. 8485-8493, vol. 17, No. 21.

Lintner et al., "Structural and Functional Characterization of an Archaeal Clustered Regularly Interspaced Short Palindromic Repeat (CRISPR)-associated Complex for Antiviral Defense (CAS-CADE)", The Journal of Biological Chemistry, 2011, pp. 21643-21656, vol. 286, No. 24, with Supporting Online Materials.

Liu et al., "Editing DNA Methylation in the Mammalian Genome", Cell, 2016, pp. 233-247, vol. 167, and Supplementary Material.

Liu et al., "Inhibition of viral gene expression by the catalytic RNA subunit of RNase P from *Escherichia coli*", Genes & Development, 1995, pp. 471-480, vol. 9.

Lo et al., "Precise and Heritable Genome Editing in Evolutionarily Diverse Nematodes Using TALENs and CRISPR/Cas9 to Engineer Insertions and Deletions", Genetics, 2013, pp. 331-348, vol. 195, with supplementary information.

Loonstra et al., "Growth inhibition and DNA damage induced by Cre recombinase in mammalian cells", PNAS, 2001, pp. 9209-9214, vol. 98, No. 16.

Luo et al., "Highly parallel identification of essential genes in cancer cells", PNAS, 2008, pp. 20380-20385, vol. 105, No. 51.

Ma et al., "A Guide RNA Sequence Design Platform for the CRISPR/Cas9 System for Model Organism Genomes", BioMed Research International, 2013, Article ID 270805, pp. 1-4, vol. 31.

Ma et al., "CRISPR-Cas9 nuclear dynamics and target recognition in living cells", The Journal of Cell Biology, 2016, pp. 529-537, vol. 214, No. 5.

Ma et al., "Single-Stranded DNA Cleavage by Divergent CRISPR-Cas9 Enzymes", Molecular Cell, 2015, pp. 398-407, vol. 60.

Ma et al., "Structural basis for overhang-specific small interfering RNA recognition by the PAZ domain", Nature, 2004, pp. 318-322, vol. 429.

MacRae et al., "Structural Basis for Double-Stranded RNA Processing by Dicer", Science, 2006, pp. 195-198, vol. 311.

Maeder et al., "CRISPR RNA-guided activation of endogenous human genes", Nature Methods, 2013, pp. 977-979, vol. 10, No. 10, and Supplementary Material.

Maeder et al., "Robust, synergistic regulation of human gene expression using TALE activators", Nature Methods, 2013, pp. 243-245, vol. 10, No. 3, and Supplementary Material.

Mahfouz et al., "Targeted transcriptional repression using a chimeric TALE-SRDX repressor protein", Plant Molecular Biology, 2012, pp. 311-321, vol. 78.

Makarova et al., "A putative RNA-interference-based immune system in prokaryotes: computational analysis of the predicted enzymatic machinery, functional analogies with eukaryotic RNAi, and hypothetical mechanisms of action", Biology Direct, 2006, pp. 1-26, vol. 1, No. 7.

Makarova et al., "An updated evolutionary classification of CRISPR-Cas systems", Nature Reviews/Microbiology, 2015, pp. 722-736, vol. 13.

Malanowska et al., "CTnDOT integrase performs ordered homology-dependent and homology-independent strand exchanges", Nucleic Acids Research, 2007, pp. 5861-5873, vol. 35, No. 17.

Mandell et al., "Zinc Finger Tools: custom DNA-binding domains for transcription factors and nucleases", Nucleic Acids Research, 2006, pp. W516-W-523, vol. 34.

Mangold et al., "Synthesis of group A streptococcal virulence factors is controlled by a regulatory RNA molecule", Molecular Microbiology, 2004, pp. 1515-1527, vol. 53, No. 5.

Marraffini et al., "Self versus non-self discrimination during CRISPR RNA-directed immunity", Nature, 2010, pp. 568-571, vol. 463.

Martin, "Requirement for GroEL/GroES-Dependent Protein Folding under Nonpermissive Conditions of Macromolecular Crowding", Biochemistry, 2002, pp. 5050-5055, vol. 41, No. 15.

(56) References Cited

OTHER PUBLICATIONS

Mathews, "Revolutions in RNA Secondary Structure Prediction", Journal of Molecular Biology, 2006, pp. 526-532, vol. 359.
Maury et al., "Technical advances to genetically engineering human embryonic stem cells", Integrative Biology, 2011, pp. 717-723, vol. 3.
McClain et al., "Model Substrates for an RNA Enzyme", Science, 1987, pp. 527-530, vol. 238.
McIntyre et al., "Design and cloning strategies for constructing shRNA expression vectors", BMC Biotechnology, 2006, pp. 1-8, vol. 6.
Meister et al., "Human Argonaute2 Mediates RNA Cleavage Targeted by miRNAs and siRNAs", Molecular Cell, 2004, pp. 185-197, vol. 15.
Mercier et al., "A Transcription Factor Cascade Involving Fep1 and the CCAAT-Binding Factor Php4 Regulates Gene Expression in Response to Iron Deficiency in the Fission Yeast *Schizosaccharomyces pombe*", Eukaryotic Cell, 2006, pp. 1866-1881, vol. 5, No. 11.
Meshorer et al., "Chromatin in pluripotent embryonic stem cells and differentiation", Nature Reviews/Molecular Cell Biology, 2006, pp. 540-546, vol. 7.
Miao et al., "Targeted mutagenesis in rice using CRISPR-Cas system", Cell Research, 2013, pp. 1233-1236, vol. 23, No. 10.
Mittelman et al., "Zinc-finger directed double-strand breaks within CAG repeat tracts promote repeat instability in human cells", PNAS, 2009, pp. 9607-9612, vol. 106. No. 24.
Mojica et al., "Intervening Sequences of Regularly Spaced Prokaryotic Repeats Derive from Foreign Genetic Elements", Journal of Molecular Evolution, 2005, pp. 174-182, vol. 60.
Mojica et al., "Short motif sequences determine the targets of the prokaryotic CRISPR defence system", Microbiology, 2009, pp. 733-740, vol. 155.
Mojica et al., "Transcription at different salinities of Haloferax mediterranei sequences adjacent to partially modified PstI sites", Molecular Microbiology, 1993, pp. 613-621, vol. 9, No. 3.
Mojica et al., "Long stretches of short tandem repeats are present in the largest replicons of the Archaea Haloferax mediterranei and Haloferax volcanii and could be involved in replicon partitioning", Molecular Microbiology, 1995, pp. 85-93, vol. 17, No. 1.
Mojica et al., "MicroCorrespondence—Biological significance of a family of regularly spaced repeats in the genomes of Archaea, Bacteria and mitochondria", Molecular Microbiology, 2000, pp. 244-246, vol. 36, No. 1.
Molinaro et al., "Use of ultra stable UNCG tetraloop hairpins to fold RNA structures: thermodynamic and spectroscopic applications", Nucleic Acids Research, 1995, pp. 3056-3063, vol. 23, No. 15.
Moore et al., "Short Hairpin RNA (shRNA): Design, Delivery, and Assessment of Gene Knockdown", Methods in Molecular Biology, 2010, pp. 141-158, vol. 629.
Moore et al., "Improved Somatic Mutagenesis in Zebrafish Using Transcription Activator-Like Effector Nucleases (TALENs)", PLoS ONE, 2012, e37877, 9 pgs., vol. 7, No. 5.
Morgan et al., "Inducible Expression and Cytogenetic Effects of the EcoRl Restriction Endonuclease in Chinese Hamster Ovary Cells", Molecular and Cellular Biology, 1988, pp. 4204-4211, vol. 8, No. 10.
Mosberg et al., "Improving Lambda Red Genome Engineering in *Escherichia coli* via Rational Removal of Endogenous Nucleases", PLOS ONE, 2012, e44638, pp. 1-12, vol. 7, No. 9.
Moscou et al., "A Simple Cipher Governs DNA Recognition by TAL Effectors", Science, 2009, p. 1501, vol. 326.
Mukhopadhyay, "On the Same Wavelength", ASBMBTODAY, Aug. 2014, pp. 21-28, vol. 13, No. 7.
Mullen et al., "Transfer of the bacterial gene for cytosine deaminase to mammalian cells confers lethal sensitivity to 5-fluorocytosine: A negative selection system", PNAS, 1992, pp. 33-37, vol. 89.
Mulligan et al., "Expression of a Bacterial Gene in Mammalian Cells", Science, 1980, pp. 1422-1427, vol. 209.
Muzykantov, "Drug delivery by red blood cells: vascular carriers designed by Mother Nature", Expert Opinion on Drug Delivery, 2010, pp. 403-427, vol. 7, No. 4.
Saito et al., "Identification of four acidic amino acids that constitute the catalytic center of the RuvC Holliday junction resolvase", PNAS, 1995, pp. 7470-7474, vol. 92.
Sampson et al., "A CRISPR-CAS System Mediates Bacterial Innate Immune Evasion and Virulence", Nature, 2013, pp. 254-257, vol. 497, No. 7448.
Sanders et al., "Use of a macromolecular crowding agent to dissect interactions and define functions in transcriptional activation by a DNA-tracking protein: Bacteriophage T4 gene 45 protein and late transcription", PNAS, 1994, pp. 7703-7707, vol. 91.
Sanders, "Cheap and easy technique to snip DNA could revolutionize gene therapy", UC Berkeley News Center, Jan. 7, 2013, 5 pgs., retrieved Jul. 18, 2018.
Sanders, "New DNA-editing technology spawns bold UC initiative", UC Berkeley News Center, Mar. 18, 2014, 5 pgs., retrieved Jul. 18, 2018.
Sandy et al., "Mammalian RNAi: a practical guide", BioTechniques, 2005, pp. 215-224, vol. 39, No. 2.
Sashital et al., "Mechanism of Foreign DNA Selection in a Bacterial Adaptive Immune System", Molecular Cell, 2012, pp. 606-615, vol. 46.
Sauer, "Functional Expression of the cre-lox Site-Specific Recombination System in the Yeast *Saccharomyces cerevisiae*", Molecular and Cellular Biology, 1987, pp. 2087-2096, vol. 7, No. 6.
Sawitzke et al., "Recombineering: In Vivo Genetic Engineering in *E. coli*, *S. enterica*, and Beyond", Methods in Enzymology, 2007, pp. 171-199, vol. 421.
Schmidt et al., "Illegitimate Cre-dependent chromosome rearrangements in transgenic mouse spermatids", PNAS, 2000, pp. 13702-13707, vol. 97, No. 25.
Schultz et al., "The interferon system of non-mammalian vertebrates", Developmental & Comparative Immunology, 2004, pp. 499-508, vol. 28.
Seksek et al., "Nuclear pH gradient in mammalian cells revealed by laser microspectrofluorimetry", Journal of Cell Science, 1996, pp. 257-262, vol. 109.
Serganov et al., "Ribozymes, riboswitches and beyond: regulation of gene expression without proteins", Nature Reviews/Genetics, 2007, pp. 776-790, vol. 8.
Shalem et al., "Genome-Scale CRISPR-Cas9 Knockout Screening in Human Cells", Science, 2014, pp. 84-87, vol. 343.
Sims et al., "High-throughput RNA interference screening using pooled shRNA libraries and next generation sequencing", Genome Biology, 2011, R104. pp. 1-13, vol. 12.
Smith et al., "Efficient and Allele-Specific Genome Editing of Disease Loci in Human iPSCs", Molecular Therapy, 2015, pp. 570-577, vol. 23, No. 3.
Snowden et al., "Gene-Specific Targeting of H3K9 Methylation Is Sufficient for Initiating Repression In Vivo", Current Biology, 2002, pp. 2159-2166, vol. 12.
Song et al., "Cautionary Tail: The Presence of an N-Terminal Tag on Dynein Light-Chain Roadblock/LC7 Affects Its Interaction with a Functional Partner", Protein & Peptide Letters, 2007, pp. 265-268, vol. 14, No. 3.
Sorek et al., "CRISPR-Mediated Adaptive Immune Systems in Bacteria and Archaea", Annual Review of Biochemistry, 2013, pp. 237-266, vol. 82.
Sorek et al., "CRISPR—a widespread system that provides acquired resistance against phages in bacteria and archaea", Nature Reviews/Microbiology, 2008, pp. 181-186, vol. 6.
Soukup et al., "Design of allosteric hammerhead ribozymes activated by ligand-induced structure stabilization", Structure, 1999, pp. 783-791, vol. 7, No. 7.
Stern et al., "Self-targeting by CRISPR: gene regulation or autoimmunity?", Trends in Genetics, 2010, pp. 335-340, vol. 26, No. 8.
Sternberg et al., "Bacteriophage P1 Site-specific Recombination—I. Recombination Between loxP Sites", J. Mol. Biol., 1981, pp. 467-486, vol. 150.
Sternberg et al., "DNA interrogation by the CRISPR RNA-guided endonuclease Cas9", Nature, 2014, pp. 62-67, vol. 507.

(56) References Cited

OTHER PUBLICATIONS

Sternberg et al., "Mechanism of substrate selection by a highly specific CRISPR endoribonuclease", RNA, 2012, pp. 661-672, vol. 18, No. 4.
Stolfi et al., "Tissue-specific genome editing in Ciona embryos by CRISPR/Cas9", Development, 2014, pp. 4115-4120, vol. 141.
Sturm, "Invertases. Primary Structures, Functions, and Roles in Plant Development and Sucrose Partitioning", Plant Physiology, 1999, pp. 1-7, vol. 121.
Sudbeck et al., "Two Independent Nuclear Localization Signals Are Present in the DNA-binding High-mobility Group Domains of SRY and SOX9", The Journal of Biological Chemistry, 1997, pp. 27848-27852, vol. 272, No. 44.
Sun et al., "Optimized TAL effector nucleases (TALENs) for use in treatment of sickle cell disease", Molecular BioSystems, 2012, pp. 1255-1263, vol. 8.
Sung et al., "Highly efficient gene knockout in mice and zebrafish with RNA-guided endonucleases", Genome Research, 2014, pp. 125-131, vol. 24, with Supplemental Material.
Swarts et al., "CRISPR Interference Directs Strand Specific Spacer Acquisition", PLoS ONE, 2012, e35888, pp. 1-7, vol. 7, No. 4.
Swiech et al., "In vivo interrogation of gene function in the mammalian brain using CRISPR-Cas9", Nature Biotechnology, 2015, pp. 102-106, vol. 33, No. 1.
Symington et al., "Double-Strand Break End Resection and Repair Pathway Choice", Annual Review of Genetics, 2011, pp. 247-271, vol. 45.
Tan et al., "Precision Editing of Large Animal Genomes", Advances in Genetics, 2012, pp. 37-97, vol. 80.
Tan et al., "Fusion Proteins Consisting of Human Immunodeficiency Virus Type 1 Integrase and the Designed Polydactyl Zinc Finger Protein E2C Direct Integration of Viral DNA into Specific Sites", Journal of Virology, 2004, pp. 1301-1313, vol. 78, No. 3.
Tan et al., "Human Immunodeficiency Virus Type 1 Incorporated with Fusion Proteins Consisting of Integrase and the Designed Polydactyl Zinc Finger Protein E2C Can Bias Integration of Viral DNA into a Predetermined Chromosomal Region in Human Cells", Journal of Virology, 2006, pp. 1939-1948, vol. 80, No. 4.
Tan et al., "Zinc-finger protein-targeted gene regulation: Genomewide single-gene specificity", PNAS, 2003, pp. 11997-12002, vol. 100, No. 21.
Tanaka et al., "Conformational variations in an infectious protein determine prion strain differences", Nature, 2004, pp. 323-328, vol. 428.
Terns et al., "The CRISPR-Cas system: small RNA-guided invader silencing in prokaryotes", The FASEB Journal, 2012, Abstract 353.3, 1 p., vol. 26.
Terns et al., "CRISPR-based adaptive immune systems", Current Opinion in Microbiology, 2011, pp. 321-327, vol. 14.
Terpe, "Overview of tag protein fusions: from molecular and biochemical fundamentals to commercial systems", Appl. Microbiol Biotechnol, 2003, pp. 523-533, vol. 60.
Tinoco et al., "Estimation of Secondary Structure in Ribonucleic Acids", Nature, 1971, pp. 362-367, vol. 230.
Tiscornia et al., "Development of Lentiviral Vectors Expressing siRNA", Gene Transfer: Delivery and Expression of DNA and RNA, Chapter 3, Copyright 2007 Cold Spring Harbor Laboratory Press, pp. 23-34.
Titz et al., "Transcriptional activators in yeast", Nucleic Acids Research, 2006, pp. 955-967, vol. 34, No. 3.
Tkachenko et al., "Cellular Trajectories of Peptide-Modified Gold Particle Complexes: Comparison of Nuclear Localization Signals and Peptide Transduction Domains", Bioconjugate Chem., 2004, pp. 482-490, vol. 15, No. 3.
Tolia et al., "Slicer and the Argonautes", Nature Chemical Biology, 2007, pp. 36-43, vol. 3, No. 1.
Declaration of Feng Zhang, filed in the United States Patent and Trademark Office, in U.S. Appl. No. 14/054,414, filed Jan. 30, 2014; 40 pgs.
Notice of Allowance in U.S. Appl. No. 14/054,414, dated Feb. 20, 2014; 12 pgs.
Declaration of Dana Carroll, Ph.D., In Support of Suggestion of Interference Pursuant to 37 C.F.R. 41.202, filed in the United States Patent and Trademark Office, in U.S. Appl. No. 13/842,859, filed Apr. 10, 2015; 122 pgs.
Supplemental Declaration of Dana Carroll, Ph.D., In Support of Supplemental Suggestion of Interference Pursuant to 37 C.F.R. 41.202, filed in the United States Patent and Trademark Office, in U.S. Appl. No. 13/842,859, filed Nov. 4, 2015; 32 pgs.
Declaration of Dana Carroll, Ph.D., dated May 23, 2016, filed in the United States Patent and Trademark Office, Before the Patent Trial and Appeal Board, in the case of *The Broad Institute, Inc., et al. v. The Regents of the University of California, et al.*, Patent Interference No. 106,048 (DK); 875 pgs.
Second Declaration of Dana Carroll, Ph.D., dated Aug. 15, 2016, filed in the United States Patent and Trademark Office, Before the Patent Trial and Appeal Board, in the case of *The Broad Institute, Inc., et al. v. The Regents of the University of California, et al.*, Patent Interference No. 106,048 (DK); 90 pgs.
Declaration of Carol Greider, Ph.D., dated May 23, 2016, filed in the United States Patent and Trademark Office, Before the Patent Trial and Appeal Board, in the case of *The Broad Institute, Inc., et al. v. The Regents of the University of California, et al.*, Patent Interference No. 106,048 (DK); 873 pgs.
Second Declaration of Carol Greider, Ph.D., dated Aug. 15, 2016, filed in the United States Patent and Trademark Office, Before the Patent Trial and Appeal Board, in the case of *The Broad Institute, Inc., et al. v. The Regents of the University of California, et al.*, Patent Interference No. 106,048 (DK); 89 pgs.
First Declaration of Technical Expert Paul Simons in Support of Broad et al., dated May 23, 2016, filed in the United States Patent and Trademark Office, Before the Patent Trial and Appeal Board, in the case of *The Broad Institute, Inc., et al. v. The Regents of the University of California, et al.*, Patent Interference No. 106,048 (DK); 91 pgs.
Second Declaration of Technical Expert Paul Simons in Support of Broad et al., dated Jun. 22, 2016, filed in the United States Patent and Trademark Office, Before the Patent Trial and Appeal Board, in the case of *The Broad Institute, Inc., et al. v. The Regents of the University of California, et al.*, Patent Interference No. 106,048 (DK); 20 pgs.
Third Declaration of Technical Expert Paul Simons in Support of Broad et al., dated Aug. 15, 2016, filed in the United States Patent and Trademark Office, Before the Patent Trial and Appeal Board, in the case of *The Broad Institute, Inc., et al. v. The Regents of the University of California, et al.*, Patent Interference No. 106,048 (DK); 116 pgs.
Broad et al. Substantive Motion 2, filed May 23, 2016, in the United States Patent and Trademark Office, Before the Patent Trial and Appeal Board, in the case of *The Broad Institute, Inc., et al. v. The Regents of the University of California, et al.*, Patent Interference No. 106,048 (DK); 38 pgs.
Uc et al. Opposition 2, filed Aug. 15, 2016, in the United States Patent and Trademark Office, Before the Patent Trial and Appeal Board, in the case of *The Broad Institute, Inc., et al. v. The Regents of the University of California, et al.*, Patent Interference No. 106,048 (DK); 65 pgs.
Broad et al. Reply 2, filed Sep. 28, 2016, in the United States Patent and Trademark Office, Before the Patent Trial and Appeal Board, in the case of *The Broad Institute, Inc., et al. v. The Regents of the University of California, et al.*, Patent Interference No. 106,048 (DK); 44 pgs.
Decision on Motions, filed Feb. 15, 2017, in the United States Patent and Trademark Office, Before the Patent Trial and Appeal Board, in the case of *The Broad Institute, Inc., et al. v. The Regents of the University of California, et al.*, Patent Interference No. 106,048 (DK); 51 pgs.
Appellants' Brief, filed Jul. 25, 2017, in the United States Court of Appeals for the Federal Circuit, in the case of *Regents of the University of California, et al. v. The Broad Institute, Inc., et al.*, Appeal No. 2017-1907; 134 pgs.

(56) References Cited

OTHER PUBLICATIONS

Appellants' Reply Brief, filed Nov. 22, 2017, in the United States Court of Appeals for the Federal Circuit, in the case of *Regents of the University of California, et al.* v. *The Broad Institute, Inc., et al.*, Appeal No. 2017-1907; 43 pgs.
Appellees' Corrected Brief, filed Dec. 1, 2017, in the United States Court of Appeals for the Federal Circuit, in the case of *Regents of the University of California, et al.* v. *The Broad Institute, Inc., et al.*, Appeal No. 2017-1907; 80 pgs.
Decision in the case of *Regents of the Univ. of Cal.* v. *Broad Inst., Inc.*, United States Court of Appeals for the Federal Circuit, Decided Sep. 10, 2018, 903 F.3d 1286, ; 8 pgs.
Berkeley Lab webpage of Dr. James H. Doudna Cate, available at: http://nbd.lbl.gov/scientists/jamie-cate/ on Sep. 22, 2015; 6 pgs.
Bothmer et al., "Characterization of the interplay between DNA repair and CRISPR/Cas9-induced DNA lesions at an endogenous locus", Nature Communications, 2017 8:13905, pp. 1-12.
Brule et al., "Synonymous codons: Choose wisely for expression", Trends Genet., 2017, pp. 283-297, vol. 33, No. 4.
Dingwall et al., "Nuclear targeting sequences—a consensus?", Trends Biochem Sci., 1991, pp. 478-481, vol. 16.
Doudna et al., "The new frontier of genome engineering with CRISPR-Cas9", Science, 2014, 1258096, 10 pgs., 346, No. 6213. vol.
Ellenberger, "Getting a grip on DNA recognition: structures of the basic region leucine zipper, and the basic region helix-loop-helix DNA-binding domains", Current Opinion in Structural Biology, 1994, pp. 12-21, vol. 4.
Ganji et al., "DNA binding proteins explore multiple local configurations during docking via rapid rebinding", Nucleic Acids Research 2016, pp. 8376-8384, vol. 44, No. 17.
Gorlich et al., "Transport Between the Cell Nucleus and the Cytoplasm", Annual Review of Cell and Developmental Biology, 1999, pp. 607-660, vol. 15.
Midoux et al., "Chemical vectors for gene delivery: a current review on polymers, peptides and lipids containing histidine or imidazole as nucleic acids carriers", British Journal of Pharmacology, 2009, pp. 166-178, vol. 157.
Peng et al., "CRISPR-Cas9-Mediated Single-Gene and Gene Family Disruption in Trypanosoma cruzi", mBio, 2015, e02097-14, pp. 1-11, vol. 6, No. 1.
Prelich, "Gene Overexpression: Uses, Mechanisms, and Interpretation", Genetics, 2012, pp. 841-854, vol. 190.
Sternberg et al., "DNA interrogation by the CRISPR RNA-guided endonuclease Cas9", Nature, 2014, pp. 62-67, and Supplemental Information, vol. 507.
Weill et al., "Assessment of GFP Tag Position on Protein Localization and Growth Fitness in Yeast", Journal of Molecular Biology, 2019, pp. 636-641, vol. 431.
Office Action from U.S. Appl. No. 12/565,589, dated Aug. 26, 2010; 36 pgs.
Final Office Action from U.S. Appl. No. 12/565,589, dated Apr. 7, 2011; 14 pgs.
Notice of Abandonment from U.S. Appl. No. 12/565,589, dated May 30, 2012, 2 pgs.
Nagy, "Cre Recombinase: The Universal Reagent for Genome Tailoring", Genesis, 2000, pp. 99-109, vol. 26.
Nam et al., "Cas5d Protein Processes Pre-crRNA and Assembles into a Cascade-like Interference Complex in Subtype I-C/Dvulg CRISPR-Cas System", Structure, 2012, pp. 1574-1584, vol. 20.
Neef et al., "Deletion of a Cation Transporter Promotes Lysis in *Streptococcus pneumoniae*", Infection and Immunity, 2011, pp. 2314-2323, vol. 79, No. 6.
Nekrasov et al., "Targeted mutagenesis in the model plant Nicotiana benthamiana using Cas9 RNA-guided endonuclease", Nature Biotechnology, 2013, pp. 691-693, vol. 31, No. 8.
Neumann et al., "Gene transfer into mouse lyoma cells by electroporation in high electric fields", The EMBO Journal, 1982, pp. 841-845, vol. 1, No. 7.

Nishida et al., "Targeted nucleotide editing using hybrid prokaryotic and vertebrate adaptive immune systems", Science, 2016, pp. 8729-1-8729-8, vol. 353, No. 6305.
Nishimasu et al., "Crystal Structure of *Staphylococcus aureus* Cas9", Cell, 2015, pp. 1113-1126, vol. 162.
Nomura et al., "Low-density lipoprotein receptor gene therapy using helper-dependent adenovirus produces long-term protection against atherosclerosis in a mouse model of familial hypercholesterolemia", Gene Therapy, 2004, pp. 1540-1548, vol. 11.
Nomura et al., "In Vivo Site-Specific DNA Methylation with a Designed Sequence-Enabled DNA Methylase", Journal of the American Chemical Society, 2007, pp. 8676-8677, vol. 129, No. 28.
O'Gorman et al., "Recombinase-Mediated Gene Activation and Site-Specific Integration in Mammalian Cells", Science, 1991, pp. 1351-1355, vol. 251.
Olson et al., "In vivo characterization of activatable cell penetrating peptides for targeting protease activity in cancer", Integrative Biology, 2009, pp. 382-393, vol. 1.
Orillard et al., "Biochemical and Cellular Characterization of Helicobacter pylon RecA, a Protein with High-Level Constitutive Expression", Journal of Bacteriology, 2011, pp. 6490-6497, vol. 193, No. 23.
Ousterout et al., "Multiplex CRISPR/Cas9-Based Genome Editing for Correction of Dystrophin Mutations that Cause Duchenne Muscular Dystrophy", Nature Communications, 2015, pp. 1-32, vol. 6.
Paddison et al., "Short hairpin RNAs (shRNAs) induce sequence-specific silencing in mammalian cells", Genes & Development, 2002, pp. 948-958, vol. 16.
Papapetrou et al., "Genomic safe harbors permit high β-globin transgene expression in thalassemia induced pluripotent stem cells", Nature Biotechnology, 2011, pp. 73-78, vol. 29, No. 1.
Papworth et al., "Designer zinc-finger proteins and their applications", Gene, 2006, pp. 27-38, vol. 366.
Papworth et al., "Inhibition of herpes simplex virus 1 gene expression by designer zinc-finger transcription factors", PNAS, 2003, pp. 1621-1626, vol. 100, No. 4.
Pattanayak et al., "Revealing Off-Target Cleavage Specificities of Zinc Finger Nucleases by In Vitro Selection", Nature Methods, 2011, pp. 765-770, vol. 8, No. 9.
Paul et al., "Localized Expression of Small RNA Inhibitors in Human Cells", Molecular Therapy, 2003, pp. 237-247, vol. 7, No. 2.
Peebles et al., "A Self-Splicing RNA Excises an Intron Lariat", Cell, 1986, pp. 213-223, vol. 44.
Pennisi, "The CRISPR Craze", Science, 2013, pp. 833-836, vol. 341.
Perez et al., "Establishment of HIV-1 resistance in CD4+ T cells by genome editing using zinc-finger nucleases", Nature Biotechnology, 2008, pp. 1-9, vol. 26, with Supporting Material.
Perez-Pinera et al., "RNA-guided gene activation by CRISPR-Cas9-based transcription factors", Nature Methods, 2013, pp. 973-976, vol. 10, No. 10.
Perez-Rodriguez et al., "Envelope stress is a trigger of CRISPR RNA-mediated DNA silencing in *Escherichia coli*", Molecular Microbiology, 2011, pp. 584-599, vol. 79, No. 3.
Piatek et al., "RNA-guided transcriptional regulation in planta via synthetic dCas9-based transcription factors", Plant Biotechnology Journal, 2015, pp. 578-589, vol. 13.
Plehn-Dujowich et al., "Effective inhibition of influenza virus production in cultured cells by external guide sequences and ribonuclease P", PNAS, 1998, pp. 7327-7332, vol. 95.
Polisky et al., "Specificity of substrate recognition by the EcoRl restriction endonuclease", PNAS, 1975, pp. 3310-3314, vol. 72, No. 9.
Pougach et al., "Transcription, processing and function of CRISPR cassettes in *Escherichia coli*", Molecular Microbiology, 2010, pp. 1367-1379, vol. 77, No. 6.
Pourcel et al., "CRISPR elements in Yersinia pestis acquire new repeats by preferential uptake of bacteriophage DNA, and provide additional tools for evolutionary studies", Microbiology, 2005, pp. 653-663, vol. 151.

(56) References Cited

OTHER PUBLICATIONS

Qin et al., "Systematic Comparison of Constitutive Promoters and the Doxycycline-Inducible Promoter", PLoS ONE, 2010, e10611, pp. 1-4, vol. 5, No. 5.
Qiu et al., "Mutation detection using Surveyor nuclease", BioTechniques, 2004, pp. 702-707, vol. 36, No. 4.
Qureshi, "ß-Lactamase: an ideal reporter system for monitoring gene expression in live eukaryotic cells", BioTechniques, 2007, pp. 91-95, vol. 42, No. 1.
Ramirez et al., "Engineered zinc finger nickases induce homology-directed repair with reduced mutagenic effects", Nucleic Acids Research, 2012, pp. 5560-5568, vol. 40, No. 12.
Ramsubir et al., "In vivo delivery of human acid ceramidase via cord blood transplantation and direct injection of lentivirus as novel treatment approaches for Farber disease", Molecular Genetics and Metabolism, 2008, pp. 133-141, vol. 95, No. 3.
Ran et al., "In vivo genome editing using *Staphylococcus aureus* Cas9", Nature, 2015, pp. 186-191, vol. 520, and supplemental material.
Rand et al., "Argonaute2 Cleaves the Anti-Guide Strand of siRNA during RISC Activation", Cell, 2005, pp. 621-629, vol. 123.
Rath et al., "The CRISPR-Cas immune system: Biology, mechanisms and applications", Biochimie, 2015, pp. 119-128, vol. 117.
Reyon et al., "Current Protocols in Molecular Biology Engineering Designer Transcription Activator-Like Effector Nucleases (TALENs)", Current Protocols in Molecular Biology, 2012, pp. 1-17.
Rho et al., "Diverse CRISPRs Evolving in Human Microbiomes", PLoS Genetics, 2012, e1002441, pp. 1-12, vol. 8, No. 6.
Rivenbark et al., "Epigenetic reprogramming of cancer cells via targeted DNA methylation", Epigenetics, 2012, pp. 350-360, vol. 7, No. 4.
Robertson et al., "Purification and Properties of a Specific *Escherichia coli* Ribonuclease which Cleaves a Tyrosine Transfer Ribonucleic Acid Precursor", The Journal of Biological Chemistry, 1972, pp. 5243-5251, vol. 247, No. 16.
Rodriguez et al., "High-efficiency deleter mice show that FLPe is an alternative to Cre-loxP", Nature Genetics, 2000, pp. 139-140, vol. 25.
Romby et al., "An overview of RNAs with regulatory functions in gram-positive bacteria", Cellular and Molecular Life Sciences, 2010, pp. 217-237, vol. 67.
Rouillon et al., "Structure of the CRISPR Interference Complex CSM Reveals Key Similarities with Cascade", Molecular Cell, 2013, pp. 124-134, vol. 52.
Truant et al., "The Arginine-Rich Domains Present in Human Immunodeficiency Virus Type 1 Tat and Rev Function as Direct Importin ß-Dependent Nuclear Localization Signals", Molecular and Cellular Biology, 1999, pp. 1210-1217, vol. 19, No. 2.
Truong et al., "Retrohoming of a Mobile Group II Intron in Human Cells Suggests How Eukaryotes Limit Group II Intron Proliferation", PLoS Genetics, 2015, e1005422, pp. 1-35, vol. 11, No. 8.
Tsien, "The Green Fluorescent Protein", Annu. Rev. Biochem., 1998, pp. 509-544, vol. 67.
Tzur et al., "Heritable Custom Genomic Modifications in Caenorhabditis elegans via a CRISPR-Cas9 System", Genetics, 2013, pp. 1181-1185, vol. 195, with Supporting Information.
Uhlenbeck, "Tetraloops and RNA folding", Nature, 1990, pp. 613-614, vol. 346.
Upadhyay et al., "RNA-Guided Genome Editing for Target Gene Mutations in Wheat", Genes/Genomes/Genetics, 2013, pp. 2233-2238, vol. 3.
Van den Berg et al., "Effects of macromolecular crowding on protein folding and aggregation", The EMBO Journal, 1999, pp. 6927-6933, vol. 18, No. 24.
Van der Oost, "New Tool for Genome Surgery", Science, 2013, pp. 768-770, vol. 339.
Van der Ploeg, "Analysis of CRISPR in *Streptococcus mutans* suggests frequent occurrence of acquired immunity against infection by M102-like bacteriophages", Microbiology, 2009, pp. 1966-1976, vol. 155.

Van Til et al., "Lentiviral gene therapy of murine hematopoietic stem cells ameliorates the Pompe disease phenotype", Blood, 2010, pp. 5329-5337, vol. 115, No. 26.
Varani, "Exceptionally Stable Nucleic Acid Hairpins", Annu. Rev. Biophys. Biomol. Struct., 1995, pp. 379-404, vol. 24.
Vojta et al., "Repurposing the CRISPR-Cas9 system for targeted DNA methylation", Nucleic Acids Research, 2016, pp. 5615-5628, vol. 44, No. 12.
Wadia et al., "Protein transduction technology", Current Opinion in Biotechnology, 2002, pp. 52-56, vol. 13.
Wang et al., "Genetic correction of ß-thalassemia patient-specific iPS cells and its use in improving hemoglobin production in irradiated SCID mice", Cell Research, 2012, pp. 637-648, vol. 22, No. 4.
Wang et al., "Effects of Length and Location on the Cellular Response to Double-Stranded RNA", Microbiology and Molecular Biology Reviews, 2004, pp. 432-452, vol. 68, No. 3.
Wang et al., "Spatiotemporal control of gene expression by a light-switchable transgene system", Nature Methods, 2012, pp. 266-269, vol. 9, No. 3, and supplemental material.
Wang et al., "Recombinase technology: applications and possibilities", Plant Cell Rep, 2011, pp. 267-285, vol. 30.
Wang et al., "Reprogramming erythroid cells for lysosomal enzyme production leads to visceral and CNS cross-correction in mice with Hurler syndrome", PNAS, 2009, pp. 19958-19963, vol. 106, No. 47.
Wei et al., "The Fidelity Index provides a systematic quantitation of star activity of DNA restriction endonucleases", Nucleic Acids Research, 2008, e50, pp. 1-10, vol. 36, No. 9.
Weninger et al., "A toolbox of endogenous and heterologous nuclear localization sequences for the methylotrophic yeast *Pichia pastoris*", FEMS Yeast Research, 2015, pp. 1-4, vol. 15, No. 7.
Westra et al., "Cascade-mediated binding and bending of negatively supercoiled DNA", RNA Biology, 2012, pp. 1134-1138, vol. 9, No. 9.
Wiedenheft et al., "Structures of the RNA-guided surveillance complex from a bacterial immune system", Nature, 2011, pp. 486-489, vol. 477.
Woese et al., "Architecture of ribosomal RNA: Constraints on the sequence of "tetra-loops,"" PNAS, 1990, pp. 8467-8471, vol. 87.
Wu et al., "Effect of Genome Size on AAV Vector Packaging", Molecular Therapy, 2010, pp. 80-86, vol. 18, No. 1.
Wu et al., "Genome-wide binding of the CRISPR endonuclease Cas9 in mammalian cells", Nature Biotechnology, 2014, pp. 670-676, vol. 32, No. 7.
Xu et al., "Accuracy and efficiency define Bxb1 integrase as the best of fifteen candidate serine recombinases for the integration of DNA into the human genome", BMC Biotechnology, 2013, pp. 1-17, vol. 13.
Xu et al., "Efficient genome engineering in eukaryotes using Cas9 from *Streptococcus thermophilus*", Cellular and Molecular Life Sciences, 2014, pp. 383-399, vol. 72, No. 2.
Xu et al., "Cytosine methylation targetted to pre-determined sequences", Nature Genetics, 1997, pp. 376-378, vol. 17.
Yang et al., "Efficient integration of an intron RNA into double-stranded DNA by reverse splicing", Nature, 1996, pp. 332-335, vol. 381.
Yang et al., "HATs and HDACs: from structure, function and regulation to novel strategies for therapy and prevention", Oncogene, 2007, pp. 5310-5318, vol. 26.
Yosef et al., "Proteins and DNA elements essential for the CRISPR adaptation process in *Escherichia coli*", Nucleic Acids Research, 2012, pp. 5569-5576, vol. 40, No. 12.
Yu et al., "RNA interference by expression of short-interfering RNAs and hairpin RNAs in mammalian cells", PNAS, 2002, pp. 6047-6052, vol. 99, No. 9.
Yuan et al. "Selection of Guide Sequences That Direct Efficient Cleavage of mRNA by Human Ribonuclease P", Science, 1994, pp. 1269-1273, vol. 263.
Zavitz et al., "ATPase-deficient Mutants of the *Escherichia coli* DNA Replication Protein PriA Are Capable of Catalyzing the Assembly of Active Primosomes", The Journal of Biological Chemistry, 1992, pp. 6933-6940, vol. 267, No. 10.

(56) References Cited

OTHER PUBLICATIONS

Zetsche et al., "A split-Cas9 architecture for inducible genome editing and transcription modulation", Nature Biotechnology, 2015, pp. 139-142, vol. 33, No. 2.
Zhang et al., "cSSMD: assessing collective activity for addressing off-target effects in genome-scale RNA interference screens", Bioinformatics, 2011, pp. 2775-2781, vol. 27, No. 20.
Zhang et al., "Processing-Independent CRISPR RNAs Limit Natural Transformation in Neisseria meningitidis", Molecular Cell, 2013, pp. 488-503, vol. 50.
Zhang et al., "Potency of catecholamines and other L-tyrosine derivatives at the cloned mouse adrenergic receptors", Neuropharmacology, 2004, pp. 438-449, vol. 47.
Zhou et al., "Mouse model for the lysosomal disorder galactosialidosis and correction of the phenotype with overexpressing erythroid precursor cells", Genes & Development, 1995, pp. 2623-2634, vol. 9.
Zhou et al., "In Vitro Selection of External Guide Sequences for Directing RNase P-mediated Inhibition of Viral Gene Expression", The Journal of Biological Chemistry, 2002, pp. 30112-30120, vol. 277, No. 33.
Zhou et al., "Mammalian MagT1 and TUSC3 are required for cellular magnesium uptake and vertebrate embryonic development", PNAS, 2009, pp. 15750-15755, vol. 106, No. 37, and Supporting Information.
Zimmerly et al., "Group II Intron Mobility Occurs by Target DNA-Primed Reverse Transcription", Cell, 1995, pp. 545-554, vol. 82.
Zuker, "Mfold web server for nucleic acid folding and hybridization prediction", Nucleic Acids Research, 2003, pp. 3406-3415, vol. 31, No. 13.
Zuris et al., "Efficient Delivery of Genome-Editing Proteins In Vitro and In Vivo", Nature Biotechnology, 2015, pp. 73-80, vol. 33, No. 1.
Third Party Observation in Respect of European Patent Application No. 13859964.2 (EP2,928,496) (Sigma-Aldrich Co. LLC), filed Dec. 22, 2017.
Third Party Observations in Respect of European Patent Application No. 13859964.2 (EP2,928,496) (Sigma-Aldrich Co. LLC), filed Dec. 22, 2017.
Third Party Observation filed in European Application No. EP20130859964, on Mar. 22, 2019.
Third Party Observation filed in European Application No. EP20130859964, on Apr. 2, 2019.
Third Party Observations in Respect of European Patent Application No. 16183724.0 (EP3,138,911) (Sigma-Aldrich Co. LLC), filed Dec. 11, 2017.
Third Party Observation in Respect of European Patent Application No. 16183724.0 (EP3,138,911) in the Name of Sigma-Aldrich Co. LLC, filed Dec. 22, 2017.
Third Party Observations in Respect of European Patent Application No. 16183725.7 (EP3,138,912) (Sigma-Aldrich Co. LLC), filed Dec. 22, 2017.
Third Party Observation in Respect of European Patent Application No. 16183725.7 (EP3,138,912) (Sigma-Aldrich Co. LLC), filed Dec. 22, 2017.
Third Party Observation filed in European Application No. EP20180160519, on Mar. 22, 2019.
Third Party Observation filed in European Application No. EP20180160519, on Apr. 2, 2019.
Third Party Observation filed in European Application No. EP20180156734, on Mar. 15, 2019.
Third Party Observation filed in European Application No. EP20180156734, on Mar. 18, 2019.
Notice of Opposition to European Patent No. EP3138910, filed by Vossius & Partner mbB, on Dec. 22, 2017, 6 pages.
Grounds for Opposition to European Patent No. EP3138910, filed by Vossius & Partner mbB, on Jun. 20, 2018, 67 pages.
Notice of Opposition to European Patent No. EP3138910, filed by Cohausz & Florack, on Mar. 29, 2018, 7 pages.
Grounds of Opposition to European Patent No. EP3138910, filed by Cohausz & Florack, on Jun. 20, 2018, 72 pages.
Notice of Opposition to European Patent No. EP3138910, filed by Caribou Biosciences, Inc., on Apr. 12, 2018, 7 pages.
Withdrawal of Opposition to European Patent No. EP3138910, filed by Caribou Biosciences, Inc., on Apr. 26, 2018, 3 pages.
Opposition to European Patent No. EP3138910, filed by HGF Limited, on Jun. 13, 2018, 76 pages.
Opposition to European Patent No. EP3138910, filed by BASF SE, on Jun. 19, 2018, 53 pages.
Opposition to European Patent No. EP3138910, filed by Claudia Rahmstorf, on Jun. 20, 2018, 72 pages.
Opposition to European Patent No. EP3138910, filed by Mathys & Squire LLP, on Jun. 20, 2018, 34 pages.
Opposition to European Patent No. EP3138910, filed by Colm Damien Murphy, on Jun. 20, 2018, 32 pages.
Opposition to European Patent No. EP3138910, filed by Sandra Pohlman, on Jun. 20, 2018, 65 pages.
Opposition to European Patent No. EP3138910, filed by George William Schlich, on Jun. 20, 2018, 65 pages.
Proprietor's Response to the Oppositions against European Patent No. 3138910, filed Mar. 27, 2019, 116 pages.
Auxiliary Request 1, filed with Proprietor's Response to the Oppositions against European Patent No. 3138910, on Mar. 27, 2019, 3 pages.
Auxiliary Request 1, with Annotations, filed with Proprietor's Response to the Oppositions against European Patent No. 3138910, on Mar. 27, 2019, 3 pages.
Auxiliary Request 2, filed with Proprietor's Response to the Oppositions against European Patent No. 3138910, on Mar. 27, 2019, 3 pages.
Auxiliary Request 2, with Annotations, filed with Proprietor's Response to the Oppositions against European Patent No. 3138910, on Mar. 27, 2019, 3 pages.
Auxiliary Request 3, filed with Proprietor's Response to the Oppositions against European Patent No. 3138910, on Mar. 27, 2019, 3 pages.
Auxiliary Request 3, with Annotations, filed with Proprietor's Response to the Oppositions against European Patent No. 3138910, on Mar. 27, 2019, 3 pages.
Auxiliary Request 4, filed with Proprietor's Response to the Oppositions against European Patent No. 3138910, on Mar. 27, 2019, 3 pages.
Auxiliary Request 4, with Annotations, filed with Proprietor's Response to the Oppositions against European Patent No. 3138910, on Mar. 27, 2019, 3 pages.
Auxiliary Request 5, filed with Proprietor's Response to the Oppositions against European Patent No. 3138910, on Mar. 27, 2019, 3 pages.
Auxiliary Request 5, with Annotations, filed with Proprietor's Response to the Oppositions against European Patent No. 3138910, on Mar. 27, 2019, 3 pages.
Auxiliary Request 6, filed with Proprietor's Response to the Oppositions against European Patent No. 3138910, on Mar. 27, 2019, 3 pages.
Auxiliary Request 6, with Annotations, filed with Proprietor's Response to the Oppositions against European Patent No. 3138910, on Mar. 27, 2019, 3 pages.
Auxiliary Request 7, filed with Proprietor's Response to the Oppositions against European Patent No. 3138910, on Mar. 27, 2019, 3 pages.
Auxiliary Request 7, with Annotations, filed with Proprietor's Response to the Oppositions against European Patent No. 3138910, on Mar. 27, 2019, 3 pages.
Auxiliary Request 8, filed with Proprietor's Response to the Oppositions against European Patent No. 3138910, on Mar. 27, 2019, 3 pages.
Auxiliary Request 8, with Annotations, filed with Proprietor's Response to the Oppositions against European Patent No. 3138910, on Mar. 27, 2019, 3 pages.
Auxiliary Request 9, filed with Proprietor's Response to the Oppositions against European Patent No. 3138910, on Mar. 27, 2019, 3 pages.

(56) References Cited

OTHER PUBLICATIONS

Auxiliary Request 9, with Annotations, filed with Proprietor's Response to the Oppositions against European Patent No. 3138910, on Mar. 27, 2019, 3 pages.
Auxiliary Request 10, filed with Proprietor's Response to the Oppositions against European Patent No. 3138910, on Mar. 27, 2019, 2 pages.
Auxiliary Request 10, with Annotations, filed with Proprietor's Response to the Oppositions against European Patent No. 3138910, on Mar. 27, 2019, 3 pages.
Auxiliary Request 11, filed with Proprietor's Response to the Oppositions against European Patent No. 3138910, on Mar. 27, 2019, 2 pages.
Auxiliary Request 11, with Annotations, filed with Proprietor's Response to the Oppositions against European Patent No. 3138910, on Mar. 27, 2019, 3 pages.
Auxiliary Request 12, filed with Proprietor's Response to the Oppositions against European Patent No. 3138910, on Mar. 27, 2019, 2 pages.
Auxiliary Request 12, with Annotations, filed with Proprietor's Response to the Oppositions against European Patent No. 3138910, on Mar. 27, 2019, 3 pages.
Auxiliary Request 13, filed with Proprietor's Response to the Oppositions against European Patent No. 3138910, on Mar. 27, 2019, 2 pages.
Auxiliary Request 13, with Annotations, filed with Proprietor's Response to the Oppositions against European Patent No. 3138910, on Mar. 27, 2019, 3 pages.
Auxiliary Request 14, filed with Proprietor's Response to the Oppositions against European Patent No. 3138910, on Mar. 27, 2019, 3 pages.
Auxiliary Request 14, with Annotations, filed with Proprietor's Response to the Oppositions against European Patent No. 3138910, on Mar. 27, 2019, 3 pages.
Notice of Opposition to European Patent No. EP3138911, filed by George William Schlich, on Dec. 6, 2018, 8 pages.
Notice of Opposition to European Patent No. EP3138911, filed by Dr. Martin Grund, on Jan. 30, 2019.
Notice of Opposition to European Patent No. EP3138911, filed by Vossius & Partner, on Feb. 22, 2019, 6 pages.
Notice of Opposition to European Patent No. EP3138912, filed by George William Schlich, on Dec. 6, 2018, 8 pages.
Notice of Opposition to European Patent No. EP3138912, filed by Dr. Martin Grund, on Jan. 30, 2019, 6 pages.
Notice of Opposition to European Patent No. EP3138912, filed by Vossius & Partner, on Feb. 22, 2019, 6 pages.
Ill et al., "Gene Therapy Progress and Prospects: Recent progress in transgene and RNAi expression cassettes", Gene Therapy, 2005, pp. 795-802, vol. 12.
Ishino et al., "Nucleotide Sequence of the iap Gene, Responsible for Alkaline Phosphatase Isozyme Conversion in *Escherichia coli*, and Identification of the Gene Product", Journal of Bacteriology, 1987, pp. 5429-5433, vol. 169, No. 12.
International Search Report and Written Opinion from International Application No. PCT/US2013/032589, dated Jul. 26, 2013; 17 pgs.
Jacoby et al., "Expanding LAGLIDADG endonuclease scaffold diversity by rapidly surveying evolutionary sequence space", Nucleic Acids Research, 2012, pp. 4954-4964, vol. 40, No. 11.
Jaeger et al., "TectoRNA: modular assembly units for the construction of RNA nano-objects", Nucleic Acids Research, 2001, pp. 455-463, vol. 29, No. 2.
Jakoby et al., "bZIP transcription factors in *Arabidopsis*", Trends in Plant Science, 2002, pp. 106-111, vol. 7, No. 3.
Jans et al., "Nuclear targeting signal recognition: a key control point in nuclear transport?", BioEssays, 2000, pp. 532-544, vol. 22.
Jansa et al., "The transcript release factor PTRF augments ribosomal gene transcription by facilitating reinitiation of RNA polymerase I", Nucleic Acids Research, 2001, pp. 423-429, vol. 29, No. 2.
Jansen et al., "Identification of genes that are associated with DNA repeats in prokaryotes", Molecular Microbiology, 2002, pp. 1565-1575, vol. 43, No. 6.
Janssen et al., "Mouse models of K-ras-initiated carcinogenesis", Biochimica et Biophysica Acta, 2005, pp. 145-154, vol. 1756.
Jiang et al., "Demonstration of CRISPR/Cas9/sgRNA-mediated targeted gene modification in *Arabidopsis*, tobacco, and rice", Nucleic Acids Research, 2013, e188, pp. 1-12, vol. 41, No. 20.
Jore et al., "Structural basis for CRISPR RNA-guided DNA recognition by Cascade", Nature Structural & Molecular Biology, 2011, pp. 529-536, vol. 18, No. 5.
Joung, "Building with Biological LEGO", BioTechniques, 2012, p. 351, vol. 52, No. 6.
Karow et al., "Site-Specific Recombinase Strategy to Create Induced Pluripotent Stem Cells Efficiently with Plasmid DNA", Stem Cells, 2011, pp. 1696-1704, vol. 29.
Karvelis et al., "Rapid characterization of CRISPR-Cas9 protospacer adjacent motif sequence elements", Genome Biology, 2015, pp. 1-13, vol. 16.
Karvelis et al., "crRNA and tracrRNA guide Cas9-mediated DNA interference in S *Streptococcus thermophilus*", RNA Biology, 2013, pp. 841-851, vol. 10, No. 5.
Katic et al., "Targeted Heritable Mutation and Gene Conversion by Cas9-CRISPR in Caenorhabditis elegans", Genetics, 2013, pp. 1173-1176, vol. 195.
Kaufman, "Overview of Vector Design for Mammalian Gene Expression", Molecular Biotechnology, 2000, pp. 151-160, vol. 16.
Kearns et al., "Functional annotation of native enhancers with a Cas9-histone demethylase fusion", Nature Methods, 2015, pp. 401-403, vol. 12, No. 5.
Kennedy et al., "Rapid blue light induction of protein interactions in living cells", Nature Methods, 2010, pp. 973-975, vol. 7, No. 12.
Kido et al., "*Escherichia coli* RecA Protein Modified with a Nuclear Location Signal Binds to Chromosomes in Living Mammalian Cells", Experimental Cell Research, 1992, pp. 107-114, vol. 198.
Kilani et al., "RNase P Ribozymes Selected in Vitro to Cleave a Viral mRNA Effectively Inhibit Its Expression in Cell Culture", The Journal of Biological Chemistry, 2000, pp. 10611-10622, vol. 275, No. 14.
Kim et al., "Inhibition of gene expression in human cells using RNase P-derived ribozymes and external guide sequences", Biochimica et Biophysica Acta, 2007, pp. 603-612, vol. 1769, No. 11-12.
Kim et al., "Highly efficient RNA-guided genome editing in human cells via delivery of purified Cas9 ribonucleoproteins", Genome Research, 2014, pp. 1012-1019, vol. 24, with Supplemental Information.
Kim et al., "Long-term expression of the human glucocerebrosidase gene in vivo after transplantation of bone-marrow-derived cells transformed with a lentivirus vector", The Journal of Gene Medicine, 2005, pp. 878-887, vol. 7.
Kim et al., "In vivo genome editing with a small Cas9 orthologue derived from Campylobacter jejuni", Nature Communications, 2017, pp. 1-12, vol. 10.
Kinnevey et al., "Emergence of Sequence Type 779 Methicillin-Resistant *Staphyloccus aureus* Harboring a Novel Pseudo Staphylococcal Cassette Chromosome mec (SCCmec)-SCC-SCC CRISPR Composite Element in Irish Hospitals", Antimicrobial Agents and Chemotherapy, 2013, pp. 524-531, vol. 57, No. 1.
Klosterman et al., "Three-dimensional motifs from the SCOR, structural classification of RNA database: extruded strands, base triples, tetraloops and U-turns", Nucleic Acids Research, 2004, pp. 2342-2352, vol. 32, No. 8.
Komor et al., "Programmable editing of a target base in genomic DNA without double-stranded DNA cleavage", Nature, 2016, pp. 420-424, vol. 533.
Konermann et al., "Genome-scale transcriptional activation by an engineered CRISPR-Cas9 complex", Nature, 2015, pp. 583-588, vol. 517(7536).
Koo et al., "Measuring and Reducing Off-Target Activities of Programmable Nucleases Including CRISPR-Cas9", Molecules and Cells, 2015, pp. 475-481, vol. 38, No. 6.

(56) References Cited

OTHER PUBLICATIONS

Koornneef et al., "Apolipoprotein B Knockdown by AAV-delivered shRNA Lowers Plasma Cholesterol in Mice", Molecular Therapy, 2011, pp. 731-740, vol. 19, No. 4.
Kunin et al., "Evolutionary conservation of sequence and secondary structures in CRISPR repeats", Genome Biology, 2007, 7 pgs., vol. 8, No. 4, Article R61.
LaCasse et al., "Nuclear localization signals overlap DNA- or RNA-binding domains in nucleic acid-binding proteins", Nucleic Acids Research, 1995, pp. 1647-1656, vol. 23, No. 10.
Lander, "The Heroes of CRISPR", Cell, 2016, pp. 18-28, vol. 164.
Lanza et al., "Evaluating the Influence of Selection Markers on Obtaining Selected Pools and Stable Cell Lines in Human Cells", Biotechnology Journal, 2013, pp. 1-34.
Le Rhun et al., "Small RNAs in streptococci", RNA Biology, 2012, pp. 414-426, vol. 9, No. 4.
Lee et al., "Targeted chromosomal deletions in human cells using zinc finger nucleases", Genome Research, 2010, pp. 81-89, vol. 20.
Leenay et al., "Identifying and Visualizing Functional PAM Diversity across CRISPR-Cas Systems", Molecular Cell, pp. 137-147, vol. 62, and Supplemental Information.
Leimig et al., "Functional amelioration of murine galactosialidosis by genetically modified bone marrow hematopoietic progenitor cells", Blood, 2002, pp. 3169-3178, vol. 99, No. 9.
Lesnik et al., "Relative Thermodynamic Stability of DNA, RNA, and DNA:RNA Hybrid Duplexes: Relationship with Base Composition and Structure", Biochemistry, 1995, pp. 10807-10815, vol. 34, No. 34.
Lewis et al., "The c-myc and PyMT oncogenes induce different tumor types in a somatic mouse model for pancreatic cancer", Genes & Development, 2003, pp. 3127-3138, vol. 17.
Li et al., "Multiplex and homologous recombination-mediated genome editing in *Arabidopsis* and Nicotiana benthamiana using guide RNA and Cas9", Nature Biotechnology, 2013, pp. 688-691, vol. 31, No. 8.
Li et al., "In vivo genome editing restores haemostasis in a mouse model of haemophilia", Nature, 2011, pp. 217-221, vol. 475.
Li et al., "High-efficiency TALEN-based gene editing produces disease-resistant rice", Nature Biotechnology, 2012, vol. 30, pp. 390-392, and Supplementary Information.
Li et al., "Targeted cleavage of mRNA in vitro by RNase P from *Escherichia coli*", PNAS, 1992, pp. 3185-3189, vol. 89.
Gabriel et al., "An unbiased genome-wide analysis of zinc-finger nuclease specificity", Nature Biotechnology, 2011, pp. 816-823, vol. 29, No. 9.
Gagnon et al., "Efficient Mutagenesis by Cas9 Protein-Mediated Oligonucleotide Insertion and Large-Scale Assessment of Single-Guide RNAs", PLOS ONE, 2014, e98186, pp. 1-8, vol. 9, No. 5.
Geißler et al., "Transcriptional Activators of Human Genes with Programmable DNA-Specificity", PLoS ONE, 2011, e19509, pp. 1-7, vol. 6, No. 5.
Gentner et al., "Identification of Hematopoietic Stem Cell-Specific miRNAs Enables Gene Therapy of Globoid Cell Leukodystrophy", Science Translational Medicine, 2010, pp. 1-11, vol. 2, No. 58.
Gersbach et al., "Targeted plasmid integration into the human genome by an engineered zinc-finger recombinase", Nucleic Acids Research, 2011, pp. 7868-7878, vol. 39, No. 17.
Gibson et al., "Ribozymes—Their Functions and Strategies for Their Use", Molecular Biotechnology, 1997, pp. 125-137, vol. 7.
Godwin et al., "Spontaneous and restriction enzyme-induced chromosomal recombination in mammalian cells", PNAS, 1994, pp. 12554-12558, vol. 91.
Goldfarb et al., "Synthetic peptides as nuclear localization signals", Nature, 1986, pp. 641-644, vol. 322.
Gordley et al., "Synthesis of programmable integrases", PNAS, 2009, pp. 5053-5058, vol. 106, No. 13.
Gorman et al., "High efficiency gene transfer into mammalian cells", Philosophical Transactions of The Royal Society of London B, Biological Sciences, 1984, pp. 343-346, vol. 307.
Gottesman, "Dicing defence in bacteria", Nature, 2011, pp. 588-589, vol. 471.
Grabowski, "Phenotype, diagnosis, and treatment of Gaucher's disease", The Lancet, 2008, pp. 1263-1271, vol. 372.
Graham et al., "Resources for the design of CRISPR gene editing experiments", Genome Biology, 2015, pp. 1-21, vol. 16.
Gratz et al., "Genome Engineering of *Drosophila* with the CRISPR RNA-Guided Cas9 Nuclease", Genetics, 2013, pp. 1029-1035, vol. 194, and 10 pages of Supporting Information.
Grens, "Enzyme Improves CRISPR: A smaller Cas9 protein enables in vivo genome engineering via viral vectors", The Scientist Magazine, Apr. 1, 2015; pp. 1-2.
Gritti, "Gene therapy for lysosomal storage disorders", Expert Opinion on Biological Therapy, 2011, pp. 1153-1167, vol. 11, No. 9.
Gryllos et al., "The CsrR/CsrS two-component system of group A *Streptococcus* responds to environmental $Mg2+$", PNAS, 2003, pp. 4227-4232, vol. 100, No. 7.
Guerrier-Takada et al., "The RNA Moiety of Ribonuclease P Is the Catalytic Subunit of the Enzyme", Cell, 1983, pp. 849-857, vol. 35.
Guilinger et al., "Fusion of catalytically inactive Cas9 to FokI nuclease improves the specificity of genome modification", Nature Biotechnology, 2014, pp. 577-582, vol. 32, No. 6.
Guschin et al., "A Rapid and General Assay for Monitoring Endogenous Gene Modification", Methods in Molecular Biology, 2010, pp. 247-256, vol. 649.
Hacein-Bey-Abina et al., "Sustained Correction of X-Linked Severe Combined Immunodeficiency by Ex Vivo Gene Therapy", The New England Journal of Medicine, 2002, pp. 1185-1193, vol. 346, No. 16.
Hale et al., "RNA-Guided RNA Cleavage by a CRISPR RNA-Cas Protein Complex", Cell, 2009, pp. 945-956, vol. 139.
Hale et al. "Prokaryotic silencing (psi)RNAs in Pyrococcus furiosus", RNA, 2008, pp. 2572-2579, vol. 14. No. 12.
Hall et al. "Effects of inert volume-excluding macromolecules on protein fiber formation. I. Equilibrium models", Biophysical Chemistry, 2002, pp. 93-104, vol. 98.
Hall et al., "Effects of inert volume-excluding macromolecules on protein fiber formation. II. Kinetic models for nucleated fiber growth", Biophysical Chemistry, 2004, pp. 299-316, vol. 107.
Hanna et al., "Treatment of Sickle Cell Anemia Mouse Model with iPS Cells Generated from Autologous Skin", Science, 2007, pp. 1920-1923, vol. 318.
Hara et al., "Generation of mutant mice via the CRISPR/Cas9 system using FokI-dCas9", Nature/Scientific Reports, 2015, pp. 1-9, vol. 5.
Hashimoto et al., "A novel method for transformation of intact yeast cells by electroinjection of plasmid DNA", Applied Microbiology and Biotechnology, 1985, pp. 336-339, vol. 21.
Hatoum-Aslan et al., "Mature clustered, regularly interspaced, short palindromic repeats RNA (crRNA) length is measured by a ruler mechanism anchored at the precursor processing site", PNAS, 2011, pp. 21218-21222, vol. 108, No. 52.
Haurwitz et al., "Sequence- and Structure-Specific RNA Processing by a CRISPR Endonuclease", Science, 2010, pp. 1355-1358, vol. 329, and 19 pages of Supporting Online Material.
Heidmann et al., "Reduction of Cre recombinase toxicity in proliferating *Drosophila* cells by estrogen-dependent activity regulation", Dev. Genes & Evolution, 2001, pp. 458-465, vol. 211.
Heintze et al., "A CRISPR CASe for high-throughput silencing", Frontiers in Genetics, 2013, pp. 1-6, vol. 4.
Hendrix et al., "RNA structural motifs: building blocks of a modular biomolecule", Quarterly Reviews of Biophysics, 2005, pp. 221-243, vol. 38, No. 3.
Hewitt, "The MHC class I antigen presentation pathway: strategies for viral immune evasion", Immunology, 2003, pp. 163-169, vol. 110.
Hibbitt et al., "RNAi-mediated knockdown of HMG CoA reductase enhances gene expression from physiologically regulated low-density lipoprotein receptor therapeutic vectors in vivo", Gene Therapy, 2012, pp. 463-467, vol. 19.

(56) References Cited

OTHER PUBLICATIONS

Hilton et al., "Epigenome editing by a CRISPR-Cas9-based acetyltransferase activates genes from promoters and enhancers", Nature Biotechnology, 2015, pp. 510-517, vol. 33, No. 5.
Hofling et al., "Human CD34+ Hematopoietic Progenitor Cell-Directed Lentiviral-Mediated Gene Therapy in a Xenotransplantation Model of Lysosomal Storage Disease", Molecular Therapy, 2004, pp. 856-865, vol. 9, No. 6.
Hollis et al., "Phage integrases for the construction and manipulation of transgenic mammals", Reproductive Biology and Endocrinology, 2003, pp. 1-11, vol. 1.
Hong et al., "Functional Analysis of Various Promoters in Lentiviral Vectors at Different Stages of In Vitro Differentiation of Mouse Embryonic Stem Cells", Molecular Therapy, 2007, pp. 1630-1639, vol. 15, No. 9.
Horvath et al., "RNA-guided genome editing a la carte", Cell Research, 2013, pp. 733-734, vol. 23, No. 6.
Horvath et al., "Comparative analysis of CRISPR loci in lactic acid bacteria genomes", International Journal of Food Microbiology, 2009, pp. 62-70, vol. 131.
Horvath et al., "Diversity, Activity, and Evolution of CRISPR Loci in *Streptococcus thermophilus*", Journal of Bacteriology, 2008, pp. 1401-1412, vol. 190, No. 4.
Horvath et al., "CRISPR/Cas, the Immune System of Bacteria and Archaea", Science, 2010, pp. 167-170, vol. 327.
Hou et al., "Efficient genome engineering in human pluripotent stem cells using Cas9 from Neisseria meningitidis", PNAS, 2013, pp. 15644-15649, vol. 110, No. 39.
Hsu et al., Development and Applications of CRISPR-Cas9 for Genome Engineering, Cell, 2014, pp. 1262-1278, vol. 157.
Huerfano et al., "Nucleofection of Expression Vectors Induces a Robust Interferon Response and Inhibition of Cell Proliferation", DNA and Cell Biology, 2013, pp. 467-479, vol. 32, No. 8.
First Office Action from Chinese Patent Application No. 201810540449.5, dated Apr. 30, 2019; 9 pgs.
Notice of Opposition filed by JH Corporate Services Pty Ltd in Australian Patent Application No. 2018229489, on Mar. 6, 2019; 3 pgs.
Statement of Grounds and Particulars filed by JH Corporate Services Pty Ltd in Opposition to Australian Patent Application No. 2018229489, on Jun. 6, 2019. 9 pages.
Notice of Opposition filed by Bayer AG on Jun. 18, 2019, against European Patent No. 3138911 (EP Application No. EP16183724.0); 8 pgs.
Notice of Opposition filed by Bayer AG on Jun. 18, 2019, against European Patent No. 3138912 (EP Application No. EP16183725.7); 8 pgs.
Notice of Opposition and Grounds filed by BASF SE on Sep. 4, 2019, against European Patent No. 3138911 (EP Application No. EP16183724.0), 58 pages.
Notice of Opposition and Grounds filed by BASF SE on Sep. 4, 2019, against European Patent No. 3138912 (EP Application No. EP16183725.7), 55 pages.
Notice of Opposition and Grounds filed by Sandra Pohlman on Sep. 5, 2019, against European Patent No. 3138911 (EP Application No. EP16183724.0), 73 pages.
Office Action from related U.S. Appl. No. 15/188,927, dated Jun. 12, 2019; 54 pgs.
Office Action from related U.S. Appl. No. 15/188,911, dated Jul. 18, 2019; 147 pgs.
Chugh et al., "Translocation and nuclear accumulation of monomer and dimer of HIV-1 Tat basic domain in triticale mesophyll protoplasts," Biochimica et Biophysica Acta, 2007, pp. 419-426, vol. 1768.
Chugh et al., "Cell-Penetrating Peptides: Nanocarrier for Macromolecule Delivery in Living Cells," IUBMB Life, 2010, pp. 183-193, vol. 62, No. 3.
Chugh et al., "Translocation of cell-penetrating peptides and delivery of their cargoes in triticale microspores," Plat Cell Rep, 2009, pp. 801-810, vol. 28.

Dianov et al., "Mammalian Base Excision Repair: the Forgotten Archangel," Nucleic Acids Research, 2013, pp. 3483-3490, vol. 41, No. 6.
Erard et al., "Inhibitors of Cell Division Reversibly Modify Hemoglobin Concentration in Human Erythroleukemia K562 Cells," Blood, 1981, pp. 1236-1239, vol. 58, No. 6.
GenBank Accession No. WP_14407541.1, "type II CRISPR RNA-guided endonuclease Cas9 [*Streptococcus pyogenes*]," publicly available Jun. 2019, printed as p. 1/1 on Jun. 27, 2019.
Kim et al., "Targeted genome engineering via zinc finger nucleases," Plant Biotechnol Rep, 2011, pp. 9-17, vol. 5.
Lee et al., "Prediction of Bacterial Proteins Carrying a Nuclear Localization Signal and Nuclear Targeting of HsdM from Klebsiella pneumoniae," The Journal of Microbiology, 2009, pp. 641-645, vol. 47, No. 5.
Sinkunas et al., "Cas3 Nuclease-Helicase Activity Assays," Methods in Molecular Biology, 2015, pp. 277-291, vol. 1311.
Wender et al., "The design, synthesis, and evaluation of molecules that enable or enhance cellular uptake: Peptoid molecular transporters," PNAS, 2000, pp. 13003-13008, vol. 97, No. 24.
Zhang et al., "Efficient gene deletion and replacement in Aspergillus niger by modified in vivo CRISPR/Cas9 systems," Bioresources and Bioprocessing, 2019, pp. 1-8, vol. 6, No. 4.
Preliminary Opinion issued by the EP Opposition Division in European Application No. 16183723.2, on Oct. 22, 2019; 30 pgs.
Office Action issued in Korean Patent Application No. 10-2019-7022305, dated Sep. 10, 2019; 8 pgs.
Notice of Opposition and Grounds filed by Patent Boutique LLP, in Opposition to European Patent No. 3138911 (EP Application No. 16183724.0), on Sep. 4, 2019, 78 pages.
Notice of Opposition and Grounds filed by Cooley (UK) LLP, in Opposition to European Patent No. 3138911 (EP Application No. 16183724.0), on Sep. 5, 2019, 59 pages.
Opposition and Statement of Facts and Arguments filed by Mathys & Squire LLP, in Opposition to European Patent No. 3138911 (EP Application No. 16183724.0), on Sep. 5, 2019, 29 pages.
Notice of Opposition and Grounds filed by Sandra Pohlman, in Opposition to European Patent No. 3138912 (EP Application No. 16183725.7), on Sep. 5, 2019, 73 pages.
Grounds of Opposition filed by Bayer AG et al. (Cohausz & Florack), in Opposition to European Patent No. 3138911 (EP Application No. 16183724.0), on Sep. 5, 2019, 80 pages.
Grounds of Opposition filed by Bayer AG et al. (Cohausz & Florack), in Opposition to European Patent No. 3138912 (EP Application No. 16183725.7), on Sep. 5, 2019, 85 pages.
Grounds of Opposition filed by George W. Schlich, in Opposition to European Patent No. 3138911 (EP Application No. 16183724.0), on Sep. 5, 2019, 62 pages.
Grounds of Opposition filed by George W. Schlich, in Opposition to European Patent No. 3138912 (EP Application No. 16183725.7), on Sep. 5, 2019, 59 pages.
Grounds of Opposition filed by Martin Grund, in Opposition to European Patent No. 3138911 (EP Application No. 16183724.0), on Sep. 5, 2019, 67 pages.
Grounds of Opposition filed by Martin Grund, in Opposition to European Patent No. 3138912 (EP Application No. 16183725.7), on Sep. 5, 2019, 70 pages.
Grounds of Opposition filed by Vossius & Partner, in Opposition to European Patent No. 3138911 (EP Application No. 16183724.0), on Sep. 5, 2019, 91 pages.
Grounds of Opposition filed by Vossius & Partner, in Opposition to European Patent No. 3138912 (EP Application No. 16183725.7), on Sep. 5, 2019, 39 pages.
Revised Statement of Grounds and Particulars filed by JH Corporate Services Ltd, in Opposition to Australian Patent Application No. 2018229489, on Sep. 16, 2019, 21 pages.
Boch et al., "Breaking the Code of DNA Binding Specificity of TAL-Type III Effectors," Science, 2009, pp. 1509-1512, vol. 326.
Brummelkamp et al., "A System for Stable Expression of Short Interfering RNAs in Mammalian Cells," Science, 2002, pp. 550-553, vol. 296.

(56) References Cited

OTHER PUBLICATIONS

Brunet et al., "Chromosomal translocations induced at specified loci in human stem cells," PNAS, 2009, pp. 10620-10625, vol. 106, No. 26.

Chen et al., "Targeted activation of diverse CRISPR-Cas systems for mammalian genome editing via proximal CRISPR targeting," Nature Communications, 2017, pp. 1-12, vol. 8.

Close et al., "The Evolution of the Bacterial Luciferase Gene Cassette (lux) as a Real-Time Bioreporter," Sensors, 2012, pp. 732-752, vol. 12.

Deuschle et al., "Regulated expression of foreign genes in mammalian cells under the control of coliphage T3 RNA polymerase and lac repressor," PNAS, 1989, pp. 5400-5404, vol. 86.

Efthymiadis et al., "The HIV-1 Tat Nuclear Localization Sequence Confers Novel Nuclear Import Properties," The Journal of Biological Chemistry, 1998, pp. 1623-1628, vol. 273, No. 3.

Epinat et al., "A novel engineered meganuclease induces homologous recombination in yeast and mammalian cells," Nucleic Acids Research, 2003, pp. 2952-2962, vol. 31, No. 11.

Gopalan et al., "Minireview: RNase P: Variations and Uses," The Journal of Biological Chemistry, 2002, pp. 6759-6762, vol. 277, No. 9.

Groth et al., "A phage integrase directs efficient site-specific integration in human cells," PNAS, 2000, pp. 5995-6000, vol. 97, No. 11.

Gunawardane et al., "A Slicer-Mediated Mechanism for Repeat-Associated siRNA 5' End Formation in *Drosophila*," Science, 2007, pp. 1587-1590, vol. 315.

Kim et al., "Mini-Review: RNAi mechanisms and applications," Biotechniques, 2008, pp. 613-616, vol. 44, No. 5.

Kosugi et al., "Systematic identification of cell cycle-dependent yeast nucleocytoplasmic shuttling proteins by prediction of composite motifs," PNAS, 2009, pp. 10171-10176, vol. 106, No. 25, and Supporting Information.

Kuspa et al., "Tagging developmental genes in Dictyostelium by restriction enzyme-mediated integration of plasmid DNA," PNAS, 1992, pp. 8803-8807, vol. 89.

Lei et al., "Gene Editing of Human Embryonic Stem Cells via an Engineered Baculoviral Vector Carrying Zinc-finger Nucleases," Molecular Therapy, 2011, pp. 942-950, vol. 19, No. 5.

Li et al., "TAL nucleases (TALNs): hybrid proteins composed of TAL effectors and FokI DNA-cleavage domain," Nucleic Acids Research, 2011, pp. 359-372, vol. 39, No. 1.

Liu et al., "Generation of a Triple-Gene Knockout Mammalian Cell Line Using Engineered Zinc-Finger Nucleases," Biotechnology and Bioengineering, 2010, pp. 97-105, vol. 106, No. 1.

Ma et al., "Highly Efficient and Specific Genome Editing in Silkworm Using Custom TALENs," PLOS ONE, 2012, e45035, pp. 1-7, vol. 7, No. 9.

Madrigal et al., "Current bioinformatic approaches to identify DNase I hypersensitive sites and genomic footprints from DNase-seq data," Frontiers in Genetics, 2012, pp. 1-3, vol. 3, No. 230.

Mineta et al., "Multiple-turnover cleavage of double-stranded DNA by sandwiched zinc-finger nuclease," Nucleic Acids Symposium Series No. 53, 2009, pp. 279-280.

Pingoud et al., "Recognition and cleavage of DNA by type-II restriction endonucleases," Eur. J. Biochem., 1997, pp. 1-22, vol. 246.

Ratel et al., "N6-methyladenine: the other methylated base of DNA," Bioessays, 2006, pp. 309-315, vol. 28, No. 3.

Ruben et al., "Structural and Functional Characterization of Human Immunodeficiency Virus tat Protein," Journal of Virology, 1989, pp. 1-8, vol. 63, No. 1.

Schiestl et al., "Integration of DNA fragments by illegitimate recombination in *Saccharomyces cerevisiae*," PNAS, 1991, pp. 7585-7589, vol. 88.

Schultz et al. "Development of a CRISPR/Cas9 system for high efficiency multiplexed gene deletion in Rhodosporidium toruloides," Biotechnology and Bioengineering, 2019, pp. 1-7.

Smith et al., "Structural Basis for Importin—a Binding of the Human Immunodeficiency Virus Tat," Scientific Reports, 2017, pp. 1-11, vol. 7.

Thurman et al., "The accessible chromatin landscape of the human genome," Nature, 2012, pp. 75-82, vol. 489.

Waterhouse et al., "Exploring Plant Genomes by RNA-Induced Gene Silencing," Nature Reviews/Genetics, 2003, pp. 29-38, vol. 4.

Extended European Search Report from European Application No. 19201769.7, dated Nov. 19, 2019; 14 pgs.

\* cited by examiner

CRISPR-BASED GENOME MODIFICATION AND REGULATION

CROSS-REFERENCE TO RELATED APPLICATIONS

This application is a continuation application of U.S. patent application Ser. No. 14/649,777, filed Jun. 4, 2015, which is a U.S. National Stage Application of PCT International Application No. PCT/US2013/073307, filed Dec. 5, 2013, which claims priority to U.S. Provisional Application Ser. No. 61/734,256, filed Dec. 6, 2012; U.S. Provisional Application Ser. No. 61/758,624, filed Jan. 30, 2013; U.S. Provisional Application Ser. No. 61/761,046, filed Feb. 5, 2013; and U.S. Provisional Application Ser. No. 61/794,422, filed Mar. 15, 2013, the disclosure of each is hereby incorporated by reference in its entirety.

SEQUENCE LISTING

This application contains a Sequence Listing that has been submitted in ASCII format via EFS-Web and is hereby incorporated by reference in its entirety. The ASCII copy, created on Dec. 3, 2013, is named 547697_SequenceListing_ ST25.txt, and is 35 kilobytes in size.

FIELD OF THE INVENTION

The present disclosure relates targeted genome modification. In particular, the disclosure relates to RNA-guided endonucleases or fusion proteins comprising CRISPR/Cas-like protein and methods of using said proteins to modify or regulate targeted chromosomal sequences.

BACKGROUND OF THE INVENTION

Targeted genome modification is a powerful tool for genetic manipulation of eukaryotic cells, embryos, and animals. For example, exogenous sequences can be integrated at targeted genomic locations and/or specific endogenous chromosomal sequences can be deleted, inactivated, or modified. Current methods rely on the use of engineered nuclease enzymes, such as, for example, zinc finger nucleases (ZFNs) or transcription activator-like effector nucleases (TALENs). These chimeric nucleases contain programmable, sequence-specific DNA-binding modules linked to a nonspecific DNA cleavage domain. Each new genomic target, however, requires the design of a new ZFN or TALEN comprising a novel sequence-specific DNA-binding module. Thus, these custom designed nucleases tend to be costly and time-consuming to prepare. Moreover, the specificities of ZFNs and TALENS are such that they can mediate off-target cleavages.

Thus, there is a need for a targeted genome modification technology that does not require the design of a new nuclease for each new targeted genomic location. Additionally, there is a need for a technology with increased specificity with few or no off-target effects.

SUMMARY OF THE INVENTION

Among the various aspects of the present disclosure is the provision of an isolated RNA-guided endonuclease, wherein the endonuclease comprises at least one nuclear localization signal, at least one nuclease domain, and at least one domain that interacts with a guide RNA to target the endonuclease to a specific nucleotide sequence for cleavage. In one embodiment, the endonuclease can be derived from a Cas9 protein. In another embodiment, the endonuclease can be modified to lack at least one functional nuclease domain. In other embodiments, the endonuclease can further comprise a cell-penetrating domain, a marker domain, or both. In a further embodiment, the endonuclease can be part of a protein-RNA complex comprising the guide RNA. In some instances, the guide RNA can be a single molecule comprising a 5' region that is complementary to a target site. Also provided is an isolated nucleic acid encoding any of the RNA-guided endonucleases disclosed herein. In some embodiments, the nucleic acid can be codon optimized for translation in mammalian cells, such as, for example, human cells. In other embodiments, the nucleic acid sequence encoding the RNA-guided endonuclease can be operably linked to a promoter control sequence, and optionally, can be part of a vector. In other embodiments, a vector comprising sequence encoding the RNA-guided endonuclease, which can be operably linked to a promoter control sequence, can also comprise sequence encoding a guide RNA, which can be operably linked to a promoter control sequence.

Another aspect of the present invention encompasses a method for modifying a chromosomal sequence in a eukaryotic cell or embryo. The method comprises introducing into a eukaryotic cell or embryo (i) at least one RNA-guided endonuclease comprising at least one nuclear localization signal or nucleic acid encoding at least one RNA-guided endonuclease as defined herein, (ii) at least one guide RNA or DNA encoding at least one guide RNA, and, optionally, (iii) at least one donor polynucleotide comprising a donor sequence. The method further comprises culturing the cell or embryo such that each guide RNA directs a RNA-guided endonuclease to a targeted site in the chromosomal sequence where the RNA-guided endonuclease introduces a double-stranded break in the targeted site, and the double-stranded break is repaired by a DNA repair process such that the chromosomal sequence is modified. In one embodiment, the RNA-guided endonuclease can be derived from a Cas9 protein. In another embodiment, the nucleic acid encoding the RNA-guided endonuclease introduced into the cell or embryo can be mRNA. In a further embodiment, wherein the nucleic acid encoding the RNA-guided endonuclease introduced into the cell or embryo can be DNA. In a further embodiment, the DNA encoding the RNA-guided endonuclease can be part of a vector that further comprises a sequence encoding the guide RNA. In certain embodiments, the eukaryotic cell can be a human cell, a non-human mammalian cell, a stem cell, a non-mammalian vertebrate cell, an invertebrate cell, a plant cell, or a single cell eukaryotic organism. In certain other embodiments, the embryo is a non-human one cell animal embryo.

A further aspect of the disclosure provides a fusion protein comprising a CRISPR/Cas-like protein or fragment thereof and an effector domain. In general, the fusion protein comprises at least one nuclear localization signal. The effector domain of the fusion protein can be a cleavage domain, an epigenetic modification domain, a transcriptional activation domain, or a transcriptional repressor domain. In one embodiment, the CRISPR/Cas-like protein of the fusion protein can be derived from a Cas9 protein. In one iteration, the Cas9 protein can be modified to lack at least one functional nuclease domain. In an alternate iteration, the Cas9 protein can be modified to lack all nuclease activity. In one embodiment, the effector domain can be a cleavage domain, such as, for example, a FokI endonuclease domain or a modified FokI endonuclease domain. In another embodiment, one fusion protein can form a dimer with another fusion protein. The dimer can be a homodimer or a heterodimer. In another embodiment, the fusion protein can form a heterodimer with a zinc finger nuclease, wherein the cleavage domain of both the fusion protein and the zinc finger nucleases is a FokI endonuclease domain or a modified FokI endonuclease domain. In still another embodiment, the fusion protein comprises a CRISPR/Cas-like protein derived from a Cas9 protein modified to lack all nuclease activity, and the effector domain is a FokI endonuclease domain or a modified FokI endonuclease domain. In still another embodiment, the fusion protein comprises a CRISPR/Cas-like protein derived from a Cas9 protein modified to lack all nuclease activity, and the effector domain can be an epigenetic modification domain, a transcriptional activation domain, or a transcriptional repressor domain. In additional embodiments, any of the fusion proteins disclosed herein can comprise at least one additional domain chosen from a nuclear localization signal, a cell-penetrating domain, and a marker domain. Also provided are isolated nucleic acids encoding any of the fusion proteins provided herein.

Still another aspect of the disclosure encompasses a method for modifying a chromosomal sequence or regulating expression of a chromosomal sequence in a cell or embryo. The method comprises introducing into the cell or embryo (a) at least one fusion protein or nucleic acid encoding at least one fusion protein, wherein the fusion protein comprises a CRISPR/Cas-like protein or a fragment thereof and an effector domain, and (b) at least one guide RNA or DNA encoding at least one guide RNA, wherein the guide RNA guides the CRISPR/Cas-like protein of the fusion protein to a targeted site in the chromosomal sequence and the effector domain of the fusion protein modifies the chromosomal sequence or regulates expression of the chromosomal sequence. In one embodiment, the CRISPR/Cas-like protein of the fusion protein can be derived from a Cas9 protein. In another embodiment, the CRISPR/Cas-like protein of the fusion protein can be modified to lack at least one functional nuclease domain. In still another embodiment, the CRISPR/Cas-like protein of the fusion protein can be modified to lack all nuclease activity. In one embodiment in which the fusion protein comprises a Cas9 protein modified to lack all nuclease activity and a FokI cleavage domain or a modified FokI cleavage domain, the method can comprise introducing into the cell or embryo one fusion protein or nucleic acid encoding one fusion protein and two guide RNAs or DNA encoding two guide RNAs, and wherein one double-stranded break is introduced in the chromosomal sequence. In another embodiment in which the fusion protein comprises a Cas9 protein modified to lack all nuclease activity and a FokI cleavage domain or a modified FokI cleavage domain, the method can comprise introducing into the cell or embryo two fusion proteins or nucleic acid encoding two fusion proteins and two guide RNAs or DNA encoding two guide RNAs, and wherein two double-stranded breaks are introduced in the chromosomal sequence. In still another one embodiment in which the fusion protein comprises a Cas9 protein modified to lack all nuclease activity and a FokI cleavage domain or a modified FokI cleavage domain, the method can comprise introducing into the cell or embryo one fusion protein or nucleic acid encoding one fusion protein, one guide RNA or nucleic acid encoding one guide RNA, and one zinc finger nuclease or nucleic acid encoding one zinc finger nuclease, wherein the zinc finger nuclease comprises a FokI cleavage domain or a modified a FokI cleavage domain, and wherein one double-stranded break is introduced into the chromosomal sequence. In certain embodiments in which the fusion protein comprises a cleavage domain, the method can further comprise introducing into the cell or embryo at least one donor polynucleotide. In embodiments in which the fusion protein comprises an effector domain chosen from an epigenetic modification domain, a transcriptional activation domain, or a transcriptional repressor domain, the fusion protein can comprise a Cas9 protein modified to lack all nuclease activity, and the method can comprise introducing into the cell or embryo one fusion protein or nucleic acid encoding one fusion protein, and one guide RNA or nucleic acid encoding one guide RNA, and wherein the structure or expression of the targeted chromosomal sequence is modified. In certain embodiments, the eukaryotic cell can be a human cell, a non-human mammalian cell, a stem cell, a non-mammalian vertebrate cell, an invertebrate cell, a plant cell, or a single cell eukaryotic organism. In certain other embodiments, the embryo is a non-human one cell animal embryo.

Other aspects and iterations of the disclosure are detailed below.

BRIEF DESCRIPTION OF THE DRAWINGS

FIG. 4A presents K562 cells transfected with 10 µg of Cas9 mRNA transcribed with an Anti-Reverse Cap Analog, 0.3 nmol of pre-annealed crRNA-tracrRNA duplex, and 10 µg of AAVS1-GFP plasmid DNA; FIG. 4B depicts K562 cells transfected 10 µg of Cas9 mRNA transcribed with an Anti-Reverse Cap Analog, 0.3 nmol of chimeric RNA, and 10 µg of AAVS1-GFP plasmid DNA; FIG. 4C shows K562 cells transfected 10 µg of Cas9 mRNA that was capped by post-transcription capping reaction, 0.3 nmol of chimeric RNA, and 10 µg of AAVS1-GFP plasmid DNA; FIG. 4D presents K562 cells transfected with 10 µg of Cas9 plasmid DNA, 5 µg of U6-chimeric RNA plasmid DNA, and 10 µg of AAVS1-GFP plasmid DNA; FIG. 4E shows K562 cells transfected with 10 µg of AAVS1-GFP plasmid DNA; and FIG. 4F presents K562 cells transfected with transfection reagents only.

DETAILED DESCRIPTION OF THE INVENTION

Figure 1A:
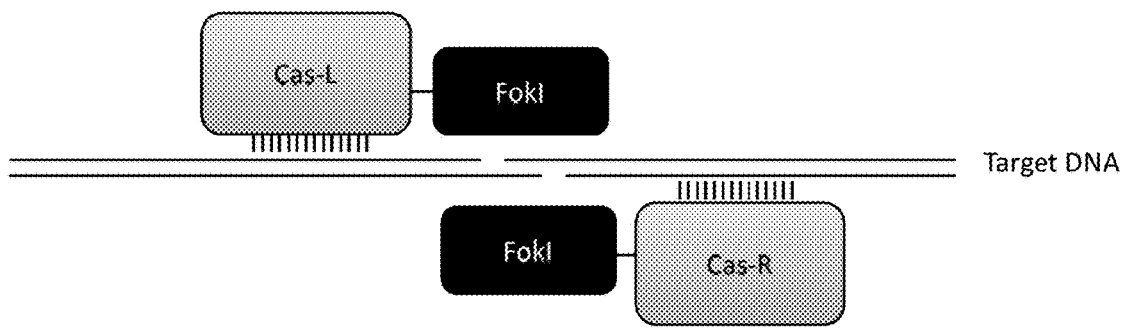
FIG. 1A diagrams genome modification using protein dimers in which a double stranded break created by a dimer composed of two fusion proteins, each of which comprises a Cas-like protein for DNA binding and a FokI cleavage domain.

Provided herein are RNA-guided endonucleases, which comprise at least one nuclear localization signal, at least one nuclease domain, and at least one domain that interacts with a guide RNA to target the endonuclease to a specific nucleotide sequence for cleavage. Also provided are nucleic acids encoding the RNA-guided endonucleases, as well as methods of using the RNA-guided endonucleases to modify chromosomal sequences of eukaryotic cells or embryos. The RNA-guided endonuclease interacts with specific guide RNAs, each of which directs the endonuclease to a specific targeted site, at which site the RNA-guided endonuclease introduces a double-stranded break that can be repaired by a DNA repair process such that the chromosomal sequence is modified. Since the specificity is provided by the guide RNA, the RNA-based endonuclease is universal and can be used with different guide RNAs to target different genomic sequences. The methods disclosed herein can be used to target and modify specific chromosomal sequences and/or introduce exogenous sequences at targeted locations in the genome of cells or embryos. Furthermore, the targeting is specific with limited off target effects.

The present disclosure provides fusion proteins, wherein a fusion protein comprises a CRISPR/Cas-like protein or fragment thereof and an effector domain. Suitable effector domains include, without limit, cleavage domains, epigenetic modification domains, transcriptional activation domains, and transcriptional repressor domains. Each fusion protein is guided to a specific chromosomal sequence by a specific guide RNA, wherein the effector domain mediates targeted genome modification or gene regulation. In one aspect, the fusion proteins can function as dimers thereby increasing the length of the target site and increasing the likelihood of its uniqueness in the genome (thus, reducing off target effects). For example, endogenous CRISPR systems modify genomic locations based on DNA binding word lengths of approximately 13-20 bp (Cong et al., Science, 339:819-823). At this word size, only 5-7% of the target sites are unique within the genome (Iseli et al, PLos One 2(6): e579). In contrast, DNA binding word sizes for zinc finger nucleases typically range from 30-36 bp, resulting in target sites that are approximately 85-87% unique within the human genome. The smaller sized DNA binding sites utilized by CRISPR-based systems limits and complicates design of targeted CRISP-based nucleases near desired locations, such as disease SNPs, small exons, start codons, and stop codons, as well as other locations within complex genomes. The present disclosure not only provides means for expanding the CRISPR DNA binding word length (i.e., so as to limit off-target activity), but further provides CRISPR fusion proteins having modified functionality. According, the disclosed CRISPR fusion proteins have increased target specificity and unique functionality(ies). Also provided herein are methods of using the fusion proteins to modify or regulate expression of targeted chromosomal sequences.

(I) RNA-Guided Endonucleases

One aspect of the present disclosure provides RNA-guided endonucleases comprising at least one nuclear localization signal, which permits entry of the endonuclease into the nuclei of eukaryotic cells and embryos such as, for example, non-human one cell embryos. RNA-guided endonucleases also comprise at least one nuclease domain and at least one domain that interacts with a guide RNA. An RNA-guided endonuclease is directed to a specific nucleic acid sequence (or target site) by a guide RNA. The guide RNA interacts with the RNA-guided endonuclease as well as the target site such that, once directed to the target site, the RNA-guided endonuclease is able to introduce a double-stranded break into the target site nucleic acid sequence. Since the guide RNA provides the specificity for the targeted cleavage, the endonuclease of the RNA-guided endonuclease is universal and can be used with different guide RNAs to cleave different target nucleic acid sequences. Provided herein are isolated RNA-guided endonucleases, isolated nucleic acids (i.e., RNA or DNA) encoding the RNA-guided endonucleases, vectors comprising nucleic acids encoding the RNA-guided endonucleases, and protein-RNA complexes comprising the RNA-guided endonuclease plus a guide RNA.

The RNA-guided endonuclease can be derived from a clustered regularly interspersed short palindromic repeats (CRISPR)/CRISPR-associated (Cas) system. The CRISPR/Cas system can be a type I, a type II, or a type III system. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx15, Csf1, Csf2, Csf3, Csf4, and Cu1966.

In one embodiment, the RNA-guided endonuclease is derived from a type II CRISPR/Cas system. In specific embodiments, the RNA-guided endonuclease is derived from a Cas9 protein. The Cas9 protein can be from *Streptococcus pyogenes*, *Streptococcus thermophilus*, *Streptococcus* sp., *Nocardiopsis dassonvillei*, *Streptomyces pristinaespiralis*, *Streptomyces viridochromogenes*, *Streptomyces viridochromogenes*, *Streptosporangium roseum*, *Streptosporangium roseum*, *Alicyclobacillus acidocaldarius*, *Bacillus pseudomycoides*, *Bacillus selenitireducens*, *Exiguobacterium sibiricum*, *Lactobacillus delbrueckii*, *Lactobacillus salivarius*, *Microscilla marina*, *Burkholderiales bacterium*, *Polaromonas naphthalenivorans*, *Polaromonas* sp., *Crocosphaera watsonii*, *Cyanothece* sp., *Microcystis aeruginosa*, *Synechococcus* sp., *Acetohalobium arabaticum*, *Ammonifex degensii*, *Caldicelulosiruptor becscii*, *Candidatus Desulforudis*, *Clostridium botulinum*, *Clostridium difficile*, *Finegoldia magna*, *Natranaerobius thermophilus*, *Pelotomaculum the rmopropionicum*, *Acidithiobacillus caldus*, *Acidithiobacillus ferrooxidans*, *Allochromatium vinosum*, *Marinobacter* sp., *Nitrosococcus halophilus*, *Nitroso-* coccus watsoni, Pseudoalteromonas haloplanktis, Ktedonobacter racemifer, Methanohalobium evestigatum, Anabaena variabilis, Nodularia spumigena, Nostoc sp., Arthrospira maxima, Arthrospira platensis, Arthrospira sp., Lyngbya sp., Microcoleus chthonoplastes, Oscillatoria sp., Petrotoga mobilis, Thermosipho africanus, or Acaryochloris marina.

In general, CRISPR/Cas proteins comprise at least one RNA recognition and/or RNA binding domain. RNA recognition and/or RNA binding domains interact with guide RNAs. CRISPR/Cas proteins can also comprise nuclease domains (i.e., DNase or RNase domains), DNA binding domains, helicase domains, RNAse domains, protein-protein interaction domains, dimerization domains, as well as other domains.

The CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzymatic activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the function of the fusion protein. The CRISPR/Cas-like protein can also be truncated or modified to optimize the activity of the effector domain of the fusion protein.

In some embodiments, the CRISPR/Cas-like protein can be derived from a wild type Cas9 protein or fragment thereof. In other embodiments, the CRISPR/Cas-like protein can be derived from modified Cas9 protein. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-stranded break in DNA. (Jinek et al., Science, 337: 816-821). In some embodiments, the Cas9-derived protein can be modified to contain only one functional nuclease domain (either a RuvC-like or a HNH-like nuclease domain). For example, the Cas9-derived protein can be modified such that one of the nuclease domains is deleted or mutated such that it is no longer functional (i.e., the nuclease activity is absent). In some embodiments in which one of the nuclease domains is inactive, the Cas9-derived protein is able to introduce a nick into a double-stranded nucleic acid (such protein is termed a "nickase"), but not cleave the double-stranded DNA. For example, an aspartate to alanine (D10A) conversion in a RuvC-like domain converts the Cas9-derived protein into a nickase. Likewise, a histidine to alanine (H840A or H839A) conversion in a HNH domain converts the Cas9-derived protein into a nickase. Each nuclease domain can be modified using well-known methods, such as site-directed mutagenesis, PCR-mediated mutagenesis, and total gene synthesis, as well as other methods known in the art.

The RNA-guided endonuclease disclosed herein comprises at least one nuclear localization signal. In general, an NLS comprises a stretch of basic amino acids. Nuclear localization signals are known in the art (see, e.g., Lange et al., J. Biol. Chem., 2007, 282:5101-5105). For example, in one embodiment, the NLS can be a monopartite sequence, such as PKKKRKV (SEQ ID NO:1) or PKKKRRV (SEQ ID NO:2). In another embodiment, the NLS can be a bipartite sequence. In still another embodiment, the NLS can be KRPAATKKAGQAKKKK (SEQ ID NO:3). The NLS can be located at the N-terminus, the C-terminal, or in an internal location of the RNA-guided endonuclease.

In some embodiments, the RNA-guided endonuclease can further comprise at least one cell-penetrating domain. In one embodiment, the cell-penetrating domain can be a cell-penetrating peptide sequence derived from the HIV-1 TAT protein. As an example, the TAT cell-penetrating sequence can be GRKKRRQRRRPPQPKKKRKV (SEQ ID NO:4). In another embodiment, the cell-penetrating domain can be TLM (PLSSIFSRIGDPPKKKRKV; SEQ ID NO:5), a cell-penetrating peptide sequence derived from the human hepatitis B virus. In still another embodiment, the cell-penetrating domain can be MPG (GALFLGWLGAAGSTMGAPKKKRKV; SEQ ID NO:6 or GALFLGFLGAAGSTMGAWSQPKKKRKV; SEQ ID NO:7). In an additional embodiment, the cell-penetrating domain can be Pep-1 (KETWWETWWTEWSQPKKKRKV; SEQ ID NO:8), VP22, a cell penetrating peptide from Herpes simplex virus, or a polyarginine peptide sequence. The cell-penetrating domain can be located at the N-terminus, the C-terminus, or in an internal location of the protein.

In still other embodiments, the RNA-guided endonuclease can also comprise at least one marker domain. Non-limiting examples of marker domains include fluorescent proteins, purification tags, and epitope tags. In some embodiments, the marker domain can be a fluorescent protein. Non limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g. YFP, EYFP, Citrine, Venus, YPet, PhiYFP, ZsYellow1,), blue fluorescent proteins (e.g. EBFP, EBFP2, Azurite, mKalama1, GFPuv, Sapphire, T-sapphire,), cyan fluorescent proteins (e.g. ECFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. In other embodiments, the marker domain can be a purification tag and/or an epitope tag. Exemplary tags include, but are not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, 51, T7, V5, VSV-G, 6×His, biotin carboxyl carrier protein (BCCP), and calmodulin.

In certain embodiments, the RNA-guided endonuclease may be part of a protein-RNA complex comprising a guide RNA. The guide RNA interacts with the RNA-guided endonuclease to direct the endonuclease to a specific target site, wherein the 5' end of the guide RNA base pairs with a specific protospacer sequence.

(II) Fusion Proteins

Another aspect of the present disclosure provides a fusion protein comprising a CRISPR/Cas-like protein or fragment thereof and an effector domain. The CRISPR/Cas-like protein is directed to a target site by a guide RNA, at which site the effector domain can modify or effect the targeted nucleic acid sequence. The effector domain can be a cleavage domain, an epigenetic modification domain, a transcriptional activation domain, or a transcriptional repressor domain. The fusion protein can further comprise at least one additional domain chosen from a nuclear localization signal, a cell-penetrating domain, or a marker domain.

(a) CRISPR/Cas-Like Protein

The fusion protein comprises a CRISPR/Cas-like protein or a fragment thereof. CRISPR/Cas-like proteins are detailed above in section (I). The CRISPR/Cas-like protein can be located at the N-terminus, the C-terminus, or in an internal location of the fusion protein In some embodiments, the CRISPR/Cas-like protein of the fusion protein can be derived from a Cas9 protein. The Cas9-derived protein can be wild type, modified, or a fragment thereof. In some embodiments, the Cas9-derived protein can be modified to contain only one functional nuclease domain (either a RuvC-like or a HNH-like nuclease domain). For example, the Cas9-derived protein can be modified such that one of the nuclease domains is deleted or mutated such that it is no longer functional (i.e., the nuclease activity is absent). In some embodiments in which one of the nuclease domains is inactive, the Cas9-derived protein is able to introduce a nick into a double-stranded nucleic acid (such protein is termed a "nickase"), but not cleave the double-stranded DNA. For example, an aspartate to alanine (D10A) conversion in a RuvC-like domain converts the Cas9-derived protein into a nickase. Likewise, a histidine to alanine (H840A or H839A) conversion in a HNH domain converts the Cas9-derived protein into a nickase. In other embodiments, both of the RuvC-like nuclease domain and the HNH-like nuclease domain can be modified or eliminated such that the Cas9-derived protein is unable to nick or cleave double stranded nucleic acid. In still other embodiments, all nuclease domains of the Cas9-derived protein can be modified or eliminated such that the Cas9-derived protein lacks all nuclease activity.

In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art. In an exemplary embodiment, the CRISPR/Cas-like protein of the fusion protein is derived from a Cas9 protein in which all the nuclease domains have been inactivated or deleted.

(b) Effector Domain

The fusion protein also comprises an effector domain. The effector domain can be a cleavage domain, an epigenetic modification domain, a transcriptional activation domain, or a transcriptional repressor domain. The effector domain can be located at the N-terminus, the C-terminus, or in an internal location of the fusion protein.

(i) Cleavage Domain

In some embodiments, the effector domain is a cleavage domain. As used herein, a "cleavage domain" refers to a domain that cleaves DNA. The cleavage domain can be obtained from any endonuclease or exonuclease. Non-limiting examples of endonucleases from which a cleavage domain can be derived include, but are not limited to, restriction endonucleases and homing endonucleases. See, for example, New England Biolabs Catalog or Belfort et al. (1997) Nucleic Acids Res. 25:3379-3388. Additional enzymes that cleave DNA are known (e.g., S1 Nuclease; mung bean nuclease; pancreatic DNase I; micrococcal nuclease; yeast HO endonuclease). See also Linn et al. (eds.) Nucleases, Cold Spring Harbor Laboratory Press, 1993. One or more of these enzymes (or functional fragments thereof) can be used as a source of cleavage domains.

In some embodiments, the cleavage domain can be derived from a type II-S endonuclease. Type II-S endonucleases cleave DNA at sites that are typically several base pairs away the recognition site and, as such, have separable recognition and cleavage domains. These enzymes generally are monomers that transiently associate to form dimers to cleave each strand of DNA at staggered locations. Non-limiting examples of suitable type II-S endonucleases include BfiI, BpmI, BsaI, BsgI, BsmBI, BsmI, BspMI, FokI, MboII, and SapI. In exemplary embodiments, the cleavage domain of the fusion protein is a FokI cleavage domain or a derivative thereof.

In certain embodiments, the type II-S cleavage can be modified to facilitate dimerization of two different cleavage domains (each of which is attached to a CRISPR/Cas-like protein or fragment thereof). For example, the cleavage domain of FokI can be modified by mutating certain amino acid residues. By way of non-limiting example, amino acid residues at positions 446, 447, 479, 483, 484, 486, 487, 490, 491, 496, 498, 499, 500, 531, 534, 537, and 538 of FokI cleavage domains are targets for modification. For example, modified cleavage domains of FokI that form obligate heterodimers include a pair in which a first modified cleavage domain includes mutations at amino acid positions 490 and 538 and a second modified cleavage domain that includes mutations at amino acid positions 486 and 499 (Miller et al., 2007, Nat. Biotechnol, 25:778-785; Szczpek et al., 2007, Nat. Biotechnol, 25:786-793). For example, the Glu (E) at position 490 can be changed to Lys (K) and the Ile (I) at position 538 can be changed to K in one domain (E490K, I538K), and the Gln (Q) at position 486 can be changed to E and the I at position 499 can be changed to Leu (L) in another cleavage domain (Q486E, I499L). In other embodiments, modified FokI cleavage domains can include three amino acid changes (Doyon et al. 2011, Nat. Methods, 8:74-81). For example, one modified FokI domain (which is termed ELD) can comprise Q486E, I499L, N496D mutations and the other modified FokI domain (which is termed KKR) can comprise E490K, I538K, H537R mutations.

In exemplary embodiments, the effector domain of the fusion protein is a FokI cleavage domain or a modified FokI cleavage domain.

In embodiments wherein the effector domain is a cleavage domain and the CRISPR/Cas-like protein is derived from a Cas9 protein, the Cas9-derived can be modified as discussed herein such that its endonuclease activity is eliminated. For example, the Cas9-derived can be modified by mutating the RuvC and HNH domains such that they no longer possess nuclease activity.

(ii) Epigenetic Modification Domain

In other embodiments, the effector domain of the fusion protein can be an epigenetic modification domain. In general, epigenetic modification domains alter histone structure and/or chromosomal structure without altering the DNA sequence. Changes histone and/or chromatin structure can lead to changes in gene expression. Examples of epigenetic modification include, without limit, acetylation or methylation of lysine residues in histone proteins, and methylation of cytosine residues in DNA. Non-limiting examples of suitable epigenetic modification domains include histone acetyltansferase domains, histone deacetylase domains, histone methyltransferase domains, histone demethylase domains, DNA methyltransferase domains, and DNA demethylase domains.

In embodiments in which the effector domain is a histone acetyltansferase (HAT) domain, the HAT domain can be derived from EP300 (i.e., E1A binding protein p300), CREBBP (i.e., CREB-binding protein), CDY1, CDY2, CDYL1, CLOCK, ELP3, ESA1, GCN5 (KAT2A), HAT1, KAT2B, KAT5, MYST1, MYST2, MYST3, MYST4, NCOA1, NCOA2, NCOA3, NCOAT, P/CAF, Tip60, TAFII250, or TF3C4. In one such embodiment, the HAT domain is p300

In embodiments wherein the effector domain is an epigenetic modification domain and the CRISPR/Cas-like protein is derived from a Cas9 protein, the Cas9-derived can be modified as discussed herein such that its endonuclease activity is eliminated. For example, the Cas9-derived can be modified by mutating the RuvC and HNH domains such that they no longer possess nuclease activity.

(iii) Transcriptional Activation Domain

In other embodiments, the effector domain of the fusion protein can be a transcriptional activation domain. In general, a transcriptional activation domain interacts with transcriptional control elements and/or transcriptional regulatory proteins (i.e., transcription factors, RNA polymerases, etc.) to increase and/or activate transcription of a gene. In some embodiments, the transcriptional activation domain can be, without limit, a herpes simplex virus VP16 activation domain, VP64 (which is a tetrameric derivative of VP16), a NFκB p65 activation domain, p53 activation domains 1 and 2, a CREB (cAMP response element binding protein) activation domain, an E2A activation domain, and an NFAT (nuclear factor of activated T-cells) activation domain. In other embodiments, the transcriptional activation domain can be Gal4, Gcn4, MLL, Rtg3, Gln3, Oaf1, Pip2, Pdr1, Pdr3, Pho4, and Leu3. The transcriptional activation domain may be wild type, or it may be a modified version of the original transcriptional activation domain. In some embodiments, the effector domain of the fusion protein is a VP16 or VP64 transcriptional activation domain.

In embodiments wherein the effector domain is a transcriptional activation domain and the CRISPR/Cas-like protein is derived from a Cas9 protein, the Cas9-derived protein can be modified as discussed herein such that its endonuclease activity is eliminated. For example, the Cas9-derived can be modified by mutating the RuvC and HNH domains such that they no longer possess nuclease activity.

(iv) Transcriptional Repressor Domain

In still other embodiments, the effector domain of the fusion protein can be a transcriptional repressor domain. In general, a transcriptional repressor domain interacts with transcriptional control elements and/or transcriptional regulatory proteins (i.e., transcription factors, RNA polymerases, etc.) to decrease and/or terminate transcription of a gene. Non-limiting examples of suitable transcriptional repressor domains include inducible cAMP early repressor (ICER) domains, Kruppel-associated box A (KRAB-A) repressor domains, YY1 glycine rich repressor domains, Sp1-like repressors, E(spl) repressors, IκB repressor, and MeCP2.

In embodiments wherein the effector domain is a transcriptional repressor domain and the CRISPR/Cas-like protein is derived from a Cas9 protein, the Cas9-derived protein can be modified as discussed herein such that its endonuclease activity is eliminated. For example, the cas9 can be modified by mutating the RuvC and HNH domains such that they no longer possess nuclease activity.

(c) Additional Domains

In some embodiments, the fusion protein further comprises at least one additional domain. Non-limiting examples of suitable additional domains include nuclear localization signals, cell-penetrating or translocation domains, and marker domains. Non-limiting examples of suitable nuclear localization signals, cell-penetrating domains, and marker domains are presented above in section (I).

(d) Fusion Protein Dimers

In embodiments in which the effector domain of the fusion protein is a cleavage domain, a dimer comprising at least one fusion protein can form. The dimer can be a homodimer or a heterodimer. In some embodiments, the heterodimer comprises two different fusion proteins. In other embodiments, the heterodimer comprises one fusion protein and an additional protein.

In some embodiments, the dimer is a homodimer in which the two fusion protein monomers are identical with respect to the primary amino acid sequence. In one embodiment where the dimer is a homodimer, the Cas9-derived proteins are modified such that their endonuclease activity is eliminated, i.e., such that they have no functional nuclease domains. In certain embodiments wherein the Cas9-derived proteins are modified such that their endonuclease activity is eliminated, each fusion protein monomer comprises an identical Cas9 like protein and an identical cleavage domain. The cleavage domain can be any cleavage domain, such as any of the exemplary cleavage domains provided herein. In one specific embodiment, the cleavage domain is a FokI cleavage domain or a modified FokI cleavage domain. In such embodiments, specific guide RNAs would direct the fusion protein monomers to different but closely adjacent sites such that, upon dimer formation, the nuclease domains of the two monomers would create a double stranded break in the target DNA.

In other embodiments, the dimer is a heterodimer of two different fusion proteins. For example, the CRISPR/Cas-like protein of each fusion protein can be derived from a different CRISPR/Cas protein or from an orthologous CRISPR/Cas protein from a different bacterial species. For example, each fusion protein can comprise a Cas9-like protein, which Cas9-like protein is derived from a different bacterial species. In these embodiments, each fusion protein would recognize a different target site (i.e., specified by the protospacer and/or PAM sequence). For example, the guide RNAs could position the heterodimer to different but closely adjacent sites such that their nuclease domains results in an effective double stranded break in the target DNA. The heterodimer can also have modified Cas9 proteins with nicking activity such that the nicking locations are different.

Alternatively, two fusion proteins of a heterodimer can have different effector domains. In embodiments in which the effector domain is a cleavage domain, each fusion protein can contain a different modified cleavage domain. For example, each fusion protein can contain a different modified FokI cleavage domain, as detailed above in section (II)(b)(i). In these embodiments, the Cas-9 proteins can be modified such that their endonuclease activities are eliminated.

As will be appreciated by those skilled in the art, the two fusion proteins forming a heterodimer can differ in both the CRISPR/Cas-like protein domain and the effector domain.

In any of the above-described embodiments, the homodimer or heterodimer can comprise at least one additional domain chosen from nuclear localization signals (NLSs), cell-penetrating, translocation domains and marker domains, as detailed above.

In any of the above-described embodiments, one or both of the Cas9-derived proteins can be modified such that its endonuclease activity is eliminated or modified.

In still alternate embodiments, the heterodimer comprises one fusion protein and an additional protein. For example, the additional protein can be a nuclease. In one embodiment, the nuclease is a zinc finger nuclease. A zinc finger nuclease comprises a zinc finger DNA binding domain and a cleavage domain. A zinc finger recognizes and binds three (3) nucleotides. A zinc finger DNA binding domain can comprise from about three zinc fingers to about seven zinc fingers. The zinc finger DNA binding domain can be derived from a naturally occurring protein or it can be engineered. See, for example, Beerli et al. (2002) Nat. Biotechnol. 20:135-141; Pabo et al. (2001) Ann. Rev. Biochem. 70:313-340; Isalan et al. (2001) Nat. Biotechnol. 19:656-660; Segal et al. (2001) Curr. Opin. Biotechnol. 12:632-637; Choo et al. (2000) Curr. Opin. Struct. Biol. 10:411-416; Zhang et al. (2000) J. Biol. Chem. 275(43):33850-33860; Doyon et al. (2008) Nat. Biotechnol. 26:702-708; and Santiago et al. (2008) Proc. Natl. Acad. Sci. USA 105:5809-5814. The cleavage domain of the zinc finger nuclease can be any cleavage domain detailed above in section (II)(b)(i). In exemplary embodiments, the cleavage domain of the zinc finger nuclease is a FokI cleavage domain or a modified FokI cleavage domain. Such a zinc finger nuclease will dimerize with a fusion protein comprising a FokI cleavage domain or a modified FokI cleavage domain.

In some embodiments, the zinc finger nuclease can comprise at least one additional domain chosen from nuclear localization signals, cell-penetrating or translocation domains, which are detailed above.

In certain embodiments, any of the fusion protein detailed above or a dimer comprising at least one fusion protein may be part of a protein-RNA complex comprising at least one guide RNA. A guide RNA interacts with the CRISPR-Cas0 like protein of the fusion protein to direct the fusion protein to a specific target site, wherein the 5' end of the guide RNA base pairs with a specific protospacer sequence.

(III) Nucleic Acids Encoding RNA-Guided Endonucleases or Fusion Proteins

Another aspect of the present disclosure provides nucleic acids encoding any of the RNA-guided endonucleases or fusion proteins described above in sections (I) and (II), respectively. The nucleic acid can be RNA or DNA. In one embodiment, the nucleic acid encoding the RNA-guided endonuclease or fusion protein is mRNA. The mRNA can be 5' capped and/or 3' polyadenylated. In another embodiment, the nucleic acid encoding the RNA-guided endonuclease or fusion protein is DNA. The DNA can be present in a vector (see below).

The nucleic acid encoding the RNA-guided endonuclease or fusion protein can be codon optimized for efficient translation into protein in the eukaryotic cell or animal of interest. For example, codons can be optimized for expression in humans, mice, rats, hamsters, cows, pigs, cats, dogs, fish, amphibians, plants, yeast, insects, and so forth. Programs for codon optimization are available as freeware. Commercial codon optimization programs are also available.

In some embodiments, DNA encoding the RNA-guided endonuclease or fusion protein can be operably linked to at least one promoter control sequence. In some iterations, the DNA coding sequence can be operably linked to a promoter control sequence for expression in the eukaryotic cell or animal of interest. The promoter control sequence can be constitutive, regulated, or tissue-specific. Suitable constitutive promoter control sequences include, but are not limited to, cytomegalovirus immediate early promoter (CMV), simian virus (SV40) promoter, adenovirus major late promoter, Rous sarcoma virus (RSV) promoter, mouse mammary tumor virus (MMTV) promoter, phosphoglycerate kinase (PGK) promoter, elongation factor (ED1)-alpha promoter, ubiquitin promoters, actin promoters, tubulin promoters, immunoglobulin promoters, fragments thereof, or combinations of any of the foregoing. Examples of suitable regulated promoter control sequences include without limit those regulated by heat shock, metals, steroids, antibiotics, or alcohol. Non-limiting examples of tissue-specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, NphsI promoter, OG-2 promoter, SP-B promoter, SYN1 promoter, and WASP promoter. The promoter sequence can be wild type or it can be modified for more efficient or efficacious expression. In one exemplary embodiment, the encoding DNA can be operably linked to a CMV promoter for constitutive expression in mammalian cells.

In certain embodiments, the sequence encoding the RNA-guided endonuclease or fusion protein can be operably linked to a promoter sequence that is recognized by a phage RNA polymerase for in vitro mRNA synthesis. In such embodiments, the in vitro-transcribed RNA can be purified for use in the methods detailed below in sections (IV) and (V). For example, the promoter sequence can be a T7, T3, or SP6 promoter sequence or a variation of a T7, T3, or SP6 promoter sequence. In an exemplary embodiment, the DNA encoding the fusion protein is operably linked to a T7 promoter for in vitro mRNA synthesis using T7 RNA polymerase.

In alternate embodiments, the sequence encoding the RNA-guided endonuclease or fusion protein can be operably linked to a promoter sequence for in vitro expression of the RNA-guided endonuclease or fusion protein in bacterial or eukaryotic cells. In such embodiments, the expressed protein can be purified for use in the methods detailed below in sections (IV) and (V). Suitable bacterial promoters include, without limit, T7 promoters, lac operon promoters, trp promoters, variations thereof, and combinations thereof. An exemplary bacterial promoter is tac which is a hybrid of trp and lac promoters. Non-limiting examples of suitable eukaryotic promoters are listed above.

In additional aspects, the DNA encoding the RNA-guided endonuclease or fusion protein also can be linked to a polyadenylation signal (e.g., SV40 polyA signal, bovine growth hormone (BGH) polyA signal, etc.) and/or at least one transcriptional termination sequence. Additionally, the sequence encoding the RNA-guided endonuclease or fusion protein also can be linked to sequence encoding at least one nuclear localization signal, at least one cell-penetrating domain, and/or at least one marker domain, which are detailed above in section (I).

In various embodiments, the DNA encoding the RNA-guided endonuclease or fusion protein can be present in a vector. Suitable vectors include plasmid vectors, phagemids, cosmids, artificial/mini-chromosomes, transposons, and viral vectors (e.g., lentiviral vectors, adeno-associated viral vectors, etc.). In one embodiment, the DNA encoding the RNA-guided endonuclease or fusion protein is present in a plasmid vector. Non-limiting examples of suitable plasmid vectors include pUC, pBR322, pET, pBluescript, and variants thereof. The vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. Additional information can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3$^{rd}$ edition, 2001.

In some embodiments, the expression vector comprising the sequence encoding the RNA-guided endonuclease or fusion protein can further comprise sequence encoding a guide RNA. The sequence encoding the guide RNA generally is operably linked to at least one transcriptional control sequence for expression of the guide RNA in the cell or embryo of interest. For example, DNA encoding the guide RNA can be operably linked to a promoter sequence that is recognized by RNA polymerase III (Pol III). Examples of suitable Pol III promoters include, but are not limited to, mammalian U6, U3, H1, and 7SL RNA promoters.

(IV) Method for Modifying a Chromosomal Sequence Using an RNA-Guided Endonuclease Another aspect of the present disclosure encompasses a method for modifying a chromosomal sequence in a eukaryotic cell or embryo. The method comprises introducing into a eukaryotic cell or embryo (i) at least one RNA-guided endonuclease comprising at least one nuclear localization signal or nucleic acid encoding at least one RNA-guided endonuclease comprising at least one nuclear localization signal, (ii) at least one guide RNA or DNA encoding at least one guide RNA, and, optionally, (iii) at least one donor polynucleotide comprising a donor sequence. The method further comprises culturing the cell or embryo such that each guide RNA directs an RNA-guided endonuclease to a targeted site in the chromosomal sequence where the RNA-guided endonuclease introduces a double-stranded break in the targeted site, and the double-stranded break is repaired by a DNA repair process such that the chromosomal sequence is modified.

In some embodiments, the method can comprise introducing one RNA-guided endonuclease (or encoding nucleic acid) and one guide RNA (or encoding DNA) into a cell or embryo, wherein the RNA-guided endonuclease introduces one double-stranded break in the targeted chromosomal sequence. In embodiments in which the optional donor polynucleotide is not present, the double-stranded break in the chromosomal sequence can be repaired by a non-homologous end-joining (NHEJ) repair process. Because NHEJ is error-prone, deletions of at least one nucleotide, insertions of at least one nucleotide, substitutions of at least one nucleotide, or combinations thereof can occur during the repair of the break. Accordingly, the targeted chromosomal sequence can be modified or inactivated. For example, a single nucleotide change (SNP) can give rise to an altered protein product, or a shift in the reading frame of a coding sequence can inactivate or "knock out" the sequence such that no protein product is made. In embodiments in which the optional donor polynucleotide is present, the donor sequence in the donor polynucleotide can be exchanged with or integrated into the chromosomal sequence at the targeted site during repair of the double-stranded break. For example, in embodiments in which the donor sequence is flanked by upstream and downstream sequences having substantial sequence identity with upstream and downstream sequences, respectively, of the targeted site in the chromosomal sequence, the donor sequence can be exchanged with or integrated into the chromosomal sequence at the targeted site during repair mediated by homology-directed repair process. Alternatively, in embodiments in which the donor sequence is flanked by compatible overhangs (or the compatible overhangs are generated in situ by the RNA-guided endonuclease) the donor sequence can be ligated directly with the cleaved chromosomal sequence by a non-homologous repair process during repair of the double-stranded break. Exchange or integration of the donor sequence into the chromosomal sequence modifies the targeted chromosomal sequence or introduces an exogenous sequence into the chromosomal sequence of the cell or embryo.

Figure 3A:
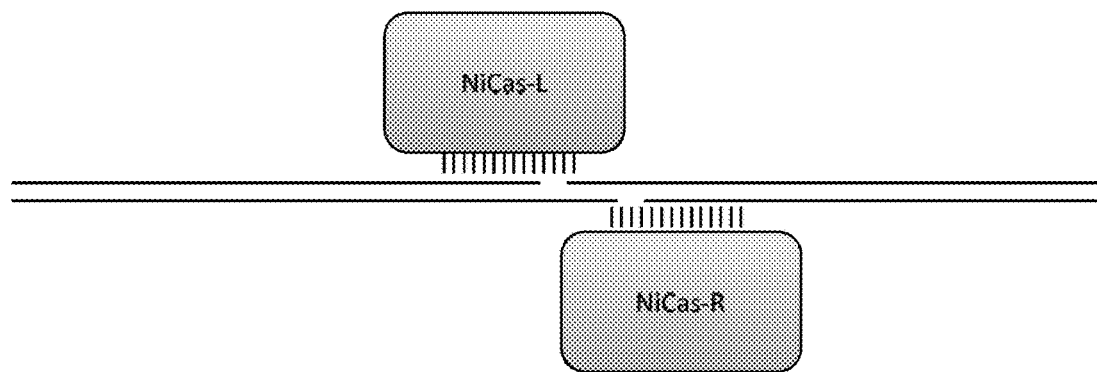
FIG. 3A diagrams a double stranded break created by two RNA-guided endonuclease that have been converted into nickases.
Figure 3B:
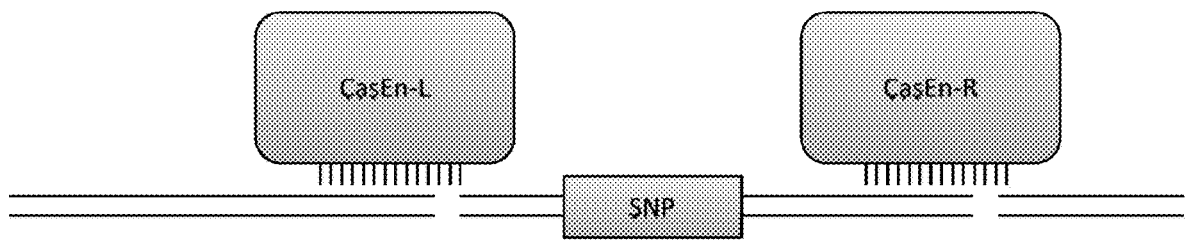
FIG. 3B depicts two double stranded breaks created by two RNA-guided endonuclease having endonuclease activity.

In other embodiments, the method can comprise introducing two RNA-guided endonucleases (or encoding nucleic acid) and two guide RNAs (or encoding DNA) into a cell or embryo, wherein the RNA-guided endonucleases introduce two double-stranded breaks in the chromosomal sequence. See FIG. 3B. The two breaks can be within several base pairs, within tens of base pairs, or can be separated by many thousands of base pairs. In embodiments in which the optional donor polynucleotide is not present, the resultant double-stranded breaks can be repaired by a non-homologous repair process such that the sequence between the two cleavage sites is lost and/or deletions of at least one nucleotide, insertions of at least one nucleotide, substitutions of at least one nucleotide, or combinations thereof can occur during the repair of the break(s). In embodiments in which the optional donor polynucleotide is present, the donor sequence in the donor polynucleotide can be exchanged with or integrated into the chromosomal sequence during repair of the double-stranded breaks by either a homology-based repair process (e.g., in embodiments in which the donor sequence is flanked by upstream and downstream sequences having substantial sequence identity with upstream and downstream sequences, respectively, of the targeted sites in the chromosomal sequence) or a non-homologous repair process (e.g., in embodiments in which the donor sequence is flanked by compatible overhangs).

In still other embodiments, the method can comprise introducing one RNA-guided endonuclease modified to cleave one strand of a double-stranded sequence (or encoding nucleic acid) and two guide RNAs (or encoding DNA) into a cell or embryo, wherein each guide RNA directs the RNA-guided endonuclease to a specific target site, at which site the modified endonuclease cleaves one strand (i.e., nicks) of the double-stranded chromosomal sequence, and wherein the two nicks are in opposite stands and in close enough proximity to constitute a double-stranded break. See FIG. 3A. In embodiments in which the optional donor polynucleotide is not present, the resultant double-stranded break can be repaired by a non-homologous repair process such that deletions of at least one nucleotide, insertions of at least one nucleotide, substitutions of at least one nucleotide, or combinations thereof can occur during the repair of the break. In embodiments in which the optional donor polynucleotide is present, the donor sequence in the donor polynucleotide can be exchanged with or integrated into the chromosomal sequence during repair of the double-stranded break by either a homology-based repair process (e.g., in embodiments in which the donor sequence is flanked by upstream and downstream sequences having substantial sequence identity with upstream and downstream sequences, respectively, of the targeted sites in the chromosomal sequence) or a non-homologous repair process (e.g., in embodiments in which the donor sequence is flanked by compatible overhangs).

(a) RNA-Guided Endonuclease

The method comprises introducing into a cell or embryo at least one RNA-guided endonuclease comprising at least one nuclear localization signal or nucleic acid encoding at least one RNA-guided endonuclease comprising at least one nuclear localization signal. Such RNA-guided endonucleases and nucleic acids encoding RNA-guided endonucleases are described above in sections (I) and (III), respectively.

In some embodiments, the RNA-guided endonuclease can be introduced into the cell or embryo as an isolated protein. In such embodiments, the RNA-guided endonuclease can further comprise at least one cell-penetrating domain, which facilitates cellular uptake of the protein. In other embodiments, the RNA-guided endonuclease can be introduced into the cell or embryo as an mRNA molecule. In still other embodiments, the RNA-guided endonuclease can be introduced into the cell or embryo as a DNA molecule. In general, DNA sequence encoding the fusion protein is operably linked to a promoter sequence that will function in the cell or embryo of interest. The DNA sequence can be linear, or the DNA sequence can be part of a vector. In still other embodiments, the fusion protein can be introduced into the cell or embryo as an RNA-protein complex comprising the fusion protein and the guide RNA.

In alternate embodiments, DNA encoding the RNA-guided endonuclease can further comprise sequence encoding a guide RNA. In general, each of the sequences encoding the RNA-guided endonuclease and the guide RNA is operably linked to appropriate promoter control sequence that allows expression of the RNA-guided endonuclease and the guide RNA, respectively, in the cell or embryo. The DNA sequence encoding the RNA-guided endonuclease and the guide RNA can further comprise additional expression control, regulatory, and/or processing sequence(s). The DNA sequence encoding the RNA-guided endonuclease and the guide RNA can be linear or can be part of a vector (b) Guide RNA The method also comprises introducing into a cell or embryo at least one guide RNA or DNA encoding at least one guide RNA. A guide RNA interacts with the RNA-guided endonuclease to direct the endonuclease to a specific target site, at which site the 5' end of the guide RNA base pairs with a specific protospacer sequence in the chromosomal sequence.

Each guide RNA comprises three regions: a first region at the 5' end that is complementary to the target site in the chromosomal sequence, a second internal region that forms a stem loop structure, and a third 3' region that remains essentially single-stranded. The first region of each guide RNA is different such that each guide RNA guides a fusion protein to a specific target site. The second and third regions of each guide RNA can be the same in all guide RNAs.

The first region of the guide RNA is complementary to sequence (i.e., protospacer sequence) at the target site in the chromosomal sequence such that the first region of the guide RNA can base pair with the target site. In various embodiments, the first region of the guide RNA can comprise from about 10 nucleotides to more than about 25 nucleotides. For example, the region of base pairing between the first region of the guide RNA and the target site in the chromosomal sequence can be about 10, 11, 12, 13, 14, 15, 16, 17, 18, 19, 20, 22, 23, 24, 25, or more than 25 nucleotides in length. In an exemplary embodiment, the first region of the guide RNA is about 19, 20, or 21 nucleotides in length.

The guide RNA also comprises a second region that forms a secondary structure. In some embodiments, the secondary structure comprises a stem (or hairpin) and a loop. The length of the loop and the stem can vary. For example, the loop can range from about 3 to about 10 nucleotides in length, and the stem can range from about 6 to about 20 base pairs in length. The stem can comprise one or more bulges of 1 to about 10 nucleotides. Thus, the overall length of the second region can range from about 16 to about 60 nucleotides in length. In an exemplary embodiment, the loop is about 4 nucleotides in length and the stem comprises about 12 base pairs.

The guide RNA also comprises a third region at the 3' end that remains essentially single-stranded. Thus, the third region has no complementarity to any chromosomal sequence in the cell of interest and has no complementarity to the rest of the guide RNA. The length of the third region can vary. In general, the third region is more than about 4 nucleotides in length. For example, the length of the third region can range from about 5 to about 60 nucleotides in length.

The combined length of the second and third regions (also called the universal or scaffold region) of the guide RNA can range from about 30 to about 120 nucleotides in length. In one aspect, the combined length of the second and third regions of the guide RNA range from about 70 to about 100 nucleotides in length.

In some embodiments, the guide RNA comprises a single molecule comprising all three regions. In other embodiments, the guide RNA can comprise two separate molecules. The first RNA molecule can comprise the first region of the guide RNA and one half of the "stem" of the second region of the guide RNA. The second RNA molecule can comprise the other half of the "stem" of the second region of the guide RNA and the third region of the guide RNA. Thus, in this embodiment, the first and second RNA molecules each contain a sequence of nucleotides that are complementary to one another. For example, in one embodiment, the first and second RNA molecules each comprise a sequence (of about 6 to about 20 nucleotides) that base pairs to the other sequence to form a functional guide RNA.

In some embodiments, the guide RNA can be introduced into the cell or embryo as a RNA molecule. The RNA molecule can be transcribed in vitro. Alternatively, the RNA molecule can be chemically synthesized.

In other embodiments, the guide RNA can be introduced into the cell or embryo as a DNA molecule. In such cases, the DNA encoding the guide RNA can be operably linked to promoter control sequence for expression of the guide RNA in the cell or embryo of interest. For example, the RNA coding sequence can be operably linked to a promoter sequence that is recognized by RNA polymerase III (Pol III). Examples of suitable Pol III promoters include, but are not limited to, mammalian U6 or H1 promoters. In exemplary embodiments, the RNA coding sequence is linked to a mouse or human U6 promoter. In other exemplary embodiments, the RNA coding sequence is linked to a mouse or human H1 promoter.

The DNA molecule encoding the guide RNA can be linear or circular. In some embodiments, the DNA sequence encoding the guide RNA can be part of a vector. Suitable vectors include plasmid vectors, phagemids, cosmids, artificial/mini-chromosomes, transposons, and viral vectors. In an exemplary embodiment, the DNA encoding the RNA-guided endonuclease is present in a plasmid vector. Non-limiting examples of suitable plasmid vectors include pUC, pBR322, pET, pBluescript, and variants thereof. The vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like.

In embodiments in which both the RNA-guided endonuclease and the guide RNA are introduced into the cell as DNA molecules, each can be part of a separate molecule (e.g., one vector containing fusion protein coding sequence and a second vector containing guide RNA coding sequence) or both can be part of the same molecule (e.g., one vector containing coding (and regulatory) sequence for both the fusion protein and the guide RNA).

(c) Target Site

An RNA-guided endonuclease in conjunction with a guide RNA is directed to a target site in the chromosomal sequence, wherein the RNA-guided endonuclease introduces a double-stranded break in the chromosomal sequence. The target site has no sequence limitation except that the sequence is immediately followed (downstream) by a consensus sequence. This consensus sequence is also known as a protospacer adjacent motif (PAM). Examples of PAM include, but are not limited to, NGG, NGGNG, and NNAGAAW (wherein N is defined as any nucleotide and W is defined as either A or T). As detailed above in section (IV)(b), the first region (at the 5' end) of the guide RNA is complementary to the protospacer of the target sequence. Typically, the first region of the guide RNA is about 19 to 21 nucleotides in length. Thus, in certain aspects, the sequence of the target site in the chromosomal sequence is 5'-$N_{19-21}$-NGG-3'. The PAM is in italics.

The target site can be in the coding region of a gene, in an intron of a gene, in a control region of a gene, in a non-coding region between genes, etc. The gene can be a protein coding gene or an RNA coding gene. The gene can be any gene of interest.

(d) Optional Donor Polynucleotide

In some embodiments, the method further comprises introducing at least one donor polynucleotide into the embryo. A donor polynucleotide comprises at least one donor sequence. In some aspects, a donor sequence of the donor polynucleotide corresponds to an endogenous or native chromosomal sequence. For example, the donor sequence can be essentially identical to a portion of the chromosomal sequence at or near the targeted site, but which comprises at least one nucleotide change. Thus, the donor sequence can comprise a modified version of the wild type sequence at the targeted site such that, upon integration or exchange with the native sequence, the sequence at the targeted chromosomal location comprises at least one nucleotide change. For example, the change can be an insertion of one or more nucleotides, a deletion of one or more nucleotides, a substitution of one or more nucleotides, or combinations thereof. As a consequence of the integration of the modified sequence, the cell or embryo/animal can produce a modified gene product from the targeted chromosomal sequence.

In other aspects, the donor sequence of the donor polynucleotide corresponds to an exogenous sequence. As used herein, an "exogenous" sequence refers to a sequence that is not native to the cell or embryo, or a sequence whose native location in the genome of the cell or embryo is in a different location. For example, the exogenous sequence can comprise protein coding sequence, which can be operably linked to an exogenous promoter control sequence such that, upon integration into the genome, the cell or embryo/animal is able to express the protein coded by the integrated sequence. Alternatively, the exogenous sequence can be integrated into the chromosomal sequence such that its expression is regulated by an endogenous promoter control sequence. In other iterations, the exogenous sequence can be a transcriptional control sequence, another expression control sequence, an RNA coding sequence, and so forth. Integration of an exogenous sequence into a chromosomal sequence is termed a "knock in."

As can be appreciated by those skilled in the art, the length of the donor sequence can and will vary. For example, the donor sequence can vary in length from several nucleotides to hundreds of nucleotides to hundreds of thousands of nucleotides.

Donor Polynucleotide Comprising Upstream and Downstream Sequences.

In some embodiments, the donor sequence in the donor polynucleotide is flanked by an upstream sequence and a downstream sequence, which have substantial sequence identity to sequences located upstream and downstream, respectively, of the targeted site in the chromosomal sequence. Because of these sequence similarities, the upstream and downstream sequences of the donor polynucleotide permit homologous recombination between the donor polynucleotide and the targeted chromosomal sequence such that the donor sequence can be integrated into (or exchanged with) the chromosomal sequence.

The upstream sequence, as used herein, refers to a nucleic acid sequence that shares substantial sequence identity with a chromosomal sequence upstream of the targeted site. Similarly, the downstream sequence refers to a nucleic acid sequence that shares substantial sequence identity with a chromosomal sequence downstream of the targeted site. As used herein, the phrase "substantial sequence identity" refers to sequences having at least about 75% sequence identity. Thus, the upstream and downstream sequences in the donor polynucleotide can have about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% A sequence identity with sequence upstream or downstream to the targeted site. In an exemplary embodiment, the upstream and downstream sequences in the donor polynucleotide can have about 95% or 100% sequence identity with chromosomal sequences upstream or downstream to the targeted site. In one embodiment, the upstream sequence shares substantial sequence identity with a chromosomal sequence located immediately upstream of the targeted site (i.e., adjacent to the targeted site). In other embodiments, the upstream sequence shares substantial sequence identity with a chromosomal sequence that is located within about one hundred (100) nucleotides upstream from the targeted site. Thus, for example, the upstream sequence can share substantial sequence identity with a chromosomal sequence that is located about 1 to about 20, about 21 to about 40, about 41 to about 60, about 61 to about 80, or about 81 to about 100 nucleotides upstream from the targeted site. In one embodiment, the downstream sequence shares substantial sequence identity with a chromosomal sequence located immediately downstream of the targeted site (i.e., adjacent to the targeted site). In other embodiments, the downstream sequence shares substantial sequence identity with a chromosomal sequence that is located within about one hundred (100) nucleotides downstream from the targeted site. Thus, for example, the downstream sequence can share substantial sequence identity with a chromosomal sequence that is located about 1 to about 20, about 21 to about 40, about 41 to about 60, about 61 to about 80, or about 81 to about 100 nucleotides downstream from the targeted site.

Each upstream or downstream sequence can range in length from about 20 nucleotides to about 5000 nucleotides. In some embodiments, upstream and downstream sequences can comprise about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2800, 3000, 3200, 3400, 3600, 3800, 4000, 4200, 4400, 4600, 4800, or 5000 nucleotides. In exemplary embodiments, upstream and downstream sequences can range in length from about 50 to about 1500 nucleotides.

Donor polynucleotides comprising the upstream and downstream sequences with sequence similarity to the targeted chromosomal sequence can be linear or circular. In embodiments in which the donor polynucleotide is circular, it can be part of a vector. For example, the vector can be a plasmid vector.

Donor Polynucleotide Comprising Targeted Cleavage Site(s).

In other embodiments, the donor polynucleotide can additionally comprise at least one targeted cleavage site that is recognized by the RNA-guided endonuclease. The targeted cleavage site added to the donor polynucleotide can be placed upstream or downstream or both upstream and downstream of the donor sequence. For example, the donor sequence can be flanked by targeted cleavage sites such that, upon cleavage by the RNA-guided endonuclease, the donor sequence is flanked by overhangs that are compatible with those in the chromosomal sequence generated upon cleavage by the RNA-guided endonuclease. Accordingly, the donor sequence can be ligated with the cleaved chromosomal sequence during repair of the double stranded break by a non-homologous repair process. Generally, donor polynucleotides comprising the targeted cleavage site(s) will be circular (e.g., can be part of a plasmid vector).

Donor Polynucleotide Comprising a Short Donor Sequence with Optional Overhangs.

In still alternate embodiments, the donor polynucleotide can be a linear molecule comprising a short donor sequence with optional short overhangs that are compatible with the overhangs generated by the RNA-guided endonuclease. In such embodiments, the donor sequence can be ligated directly with the cleaved chromosomal sequence during repair of the double-stranded break. In some instances, the donor sequence can be less than about 1,000, less than about 500, less than about 250, or less than about 100 nucleotides. In certain cases, the donor polynucleotide can be a linear molecule comprising a short donor sequence with blunt ends. In other iterations, the donor polynucleotide can be a linear molecule comprising a short donor sequence with 5' and/or 3' overhangs. The overhangs can comprise 1, 2, 3, 4, or 5 nucleotides.

Typically, the donor polynucleotide will be DNA. The DNA may be single-stranded or double-stranded and/or linear or circular. The donor polynucleotide may be a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. In certain embodiments, the donor polynucleotide comprising the donor sequence can be part of a plasmid vector. In any of these situations, the donor polynucleotide comprising the donor sequence can further comprise at least one additional sequence.

(e) Introducing into the Cell or Embryo

The RNA-targeted endonuclease(s) (or encoding nucleic acid), the guide RNA(s) (or encoding DNA), and the optional donor polynucleotide(s) can be introduced into a cell or embryo by a variety of means. In some embodiments, the cell or embryo is transfected. Suitable transfection methods include calcium phosphate-mediated transfection, nucleofection (or electroporation), cationic polymer transfection (e.g., DEAE-dextran or polyethylenimine), viral transduction, virosome transfection, virion transfection, liposome transfection, cationic liposome transfection, immunoliposome transfection, nonliposomal lipid transfection, dendrimer transfection, heat shock transfection, magnetofection, lipofection, gene gun delivery, impalefection, sonoporation, optical transfection, and proprietary agent-enhanced uptake of nucleic acids. Transfection methods are well known in the art (see, e.g., "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., $3^{rd}$ edition, 2001). In other embodiments, the molecules are introduced into the cell or embryo by microinjection. Typically, the embryo is a fertilized one-cell stage embryo of the species of interest. For example, the molecules can be injected into the pronuclei of one cell embryos.

The RNA-targeted endonuclease(s) (or encoding nucleic acid), the guide RNA(s) (or DNAs encoding the guide RNA), and the optional donor polynucleotide(s) can be introduced into the cell or embryo simultaneously or sequentially. The ratio of the RNA-targeted endonuclease(s) (or encoding nucleic acid) to the guide RNA(s) (or encoding DNA) generally will be about stoichiometric such that they can form an RNA-protein complex. In one embodiment, DNA encoding an RNA-targeted endonuclease and DNA encoding a guide RNA are delivered together within the plasmid vector.

(f) Culturing the Cell or Embryo

The method further comprises maintaining the cell or embryo under appropriate conditions such that the guide RNA(s) directs the RNA-guided endonuclease(s) to the targeted site(s) in the chromosomal sequence, and the RNA-guided endonuclease(s) introduce at least one double-stranded break in the chromosomal sequence. A double-stranded break can be repaired by a DNA repair process such that the chromosomal sequence is modified by a deletion of at least one nucleotide, an insertion of at least one nucleotide, a substitution of at least one nucleotide, or a combination thereof.

In embodiments in which no donor polynucleotide is introduced into the cell or embryo, the double-stranded break can be repaired via a non-homologous end-joining (NHEJ) repair process. Because NHEJ is error-prone, deletions of at least one nucleotide, insertions of at least one nucleotide, substitutions of at least one nucleotide, or combinations thereof can occur during the repair of the break. Accordingly, the sequence at the chromosomal sequence can be modified such that the reading frame of a coding region can be shifted and that the chromosomal sequence is inactivated or "knocked out." An inactivated protein-coding chromosomal sequence does not give rise to the protein coded by the wild type chromosomal sequence.

In embodiments in which a donor polynucleotide comprising upstream and downstream sequences is introduced into the cell or embryo, the double-stranded break can be repaired by a homology-directed repair (HDR) process such that the donor sequence is integrated into the chromosomal sequence. Accordingly, an exogenous sequence can be integrated into the genome of the cell or embryo, or the targeted chromosomal sequence can be modified by exchange of a modified sequence for the wild type chromosomal sequence.

In embodiments in which a donor polynucleotide comprising the targeted cleave site is introduced into the cell or embryo, the RNA-guided endonuclease can cleave both the targeted chromosomal sequence and the donor polynucleotide. The linearized donor polynucleotide can be integrated into the chromosomal sequence at the site of the double-stranded break by ligation between the donor polynucleotide and the cleaved chromosomal sequence via a NHEJ process.

In embodiments in which a linear donor polynucleotide comprising a short donor sequence is introduced into the cell or embryo, the short donor sequence can be integrated into the chromosomal sequence at the site of the double-stranded break via a NHEJ process. The integration can proceed via the ligation of blunt ends between the short donor sequence and the chromosomal sequence at the site of the double stranded break. Alternatively, the integration can proceed via the ligation of sticky ends (i.e., having 5' or 3' overhangs) between a short donor sequence that is flanked by overhangs that are compatible with those generated by the RNA-targeting endonuclease in the cleaved chromosomal sequence.

In general, the cell is maintained under conditions appropriate for cell growth and/or maintenance. Suitable cell culture conditions are well known in the art and are described, for example, in Santiago et al. (2008) PNAS 105:5809-5814; Moehle et al. (2007) PNAS 104:3055-3060; Urnov et al. (2005) Nature 435:646-651; and Lombardo et al (2007) Nat. Biotechnology 25:1298-1306. Those of skill in the art appreciate that methods for culturing cells are known in the art and can and will vary depending on the cell type. Routine optimization may be used, in all cases, to determine the best techniques for a particular cell type.

An embryo can be cultured in vitro (e.g., in cell culture). Typically, the embryo is cultured at an appropriate temperature and in appropriate media with the necessary $O_2/CO_2$ ratio to allow the expression of the RNA endonuclease and guide RNA, if necessary. Suitable non-limiting examples of media include M2, M16, KSOM, BMOC, and HTF media. A skilled artisan will appreciate that culture conditions can and will vary depending on the species of embryo. Routine optimization may be used, in all cases, to determine the best culture conditions for a particular species of embryo. In some cases, a cell line may be derived from an in vitro-cultured embryo (e.g., an embryonic stem cell line).

Alternatively, an embryo may be cultured in vivo by transferring the embryo into the uterus of a female host. Generally speaking the female host is from the same or similar species as the embryo. Preferably, the female host is pseudo-pregnant. Methods of preparing pseudo-pregnant female hosts are known in the art. Additionally, methods of transferring an embryo into a female host are known. Culturing an embryo in vivo permits the embryo to develop and can result in a live birth of an animal derived from the embryo. Such an animal would comprise the modified chromosomal sequence in every cell of the body.

(g) Cell and Embryo Types

A variety of eukaryotic cells and embryos are suitable for use in the method. For example, the cell can be a human cell, a non-human mammalian cell, a non-mammalian vertebrate cell, an invertebrate cell, an insect cell, a plant cell, a yeast cell, or a single cell eukaryotic organism. In general, the embryo is non-human mammalian embryo. In specific embodiments, the embryos can be a one cell non-human mammalian embryo. Exemplary mammalian embryos, including one cell embryos, include without limit mouse, rat, hamster, rodent, rabbit, feline, canine, ovine, porcine, bovine, equine, and primate embryos. In still other embodiments, the cell can be a stem cell. Suitable stem cells include without limit embryonic stem cells, ES-like stem cells, fetal stem cells, adult stem cells, pluripotent stem cells, induced pluripotent stem cells, multipotent stem cells, oligopotent stem cells, unipotent stem cells and others. In exemplary embodiments, the cell is a mammalian cell.

Non-limiting examples of suitable mammalian cells include Chinese hamster ovary (CHO) cells, baby hamster kidney (BHK) cells; mouse myeloma NS0 cells, mouse embryonic fibroblast 3T3 cells (NIH3T3), mouse B lymphoma A20 cells; mouse melanoma B16 cells; mouse myoblast C2C12 cells; mouse myeloma SP2/0 cells; mouse embryonic mesenchymal C3H-10T1/2 cells; mouse carcinoma CT26 cells, mouse prostate DuCuP cells; mouse breast EMT6 cells; mouse hepatoma Hepa1c1c7 cells; mouse myeloma J5582 cells; mouse epithelial MTD-1A cells; mouse myocardial MyEnd cells; mouse renal RenCa cells; mouse pancreatic RIN-5F cells; mouse melanoma X64 cells; mouse lymphoma YAC-1 cells; rat glioblastoma 9L cells; rat B lymphoma RBL cells; rat neuroblastoma B35 cells; rat hepatoma cells (HTC); buffalo rat liver BRL 3A cells; canine kidney cells (MDCK); canine mammary (CMT) cells; rat osteosarcoma D17 cells; rat monocyte/macrophage DH82 cells; monkey kidney SV-40 transformed fibroblast (COS7) cells; monkey kidney CVI-76 cells; African green monkey kidney (VERO-76) cells; human embryonic kidney cells (HEK293, HEK293T); human cervical carcinoma cells (HELA); human lung cells (W138); human liver cells (Hep G2); human U2-OS osteosarcoma cells, human A549 cells, human A-431 cells, and human K562 cells. An extensive list of mammalian cell lines may be found in the American Type Culture Collection catalog (ATCC, Mamassas, Va.).

(V) Method for Using a Fusion Protein to Modify a Chromosomal Sequence or Regulate Expression of a Chromosomal Sequence Another aspect of the present disclosure encompasses a method for modifying a chromosomal sequence or regulating expression of a chromosomal sequence in a cell or embryo. The method comprises introducing into the cell or embryo (a) at least one fusion protein or nucleic acid encoding at least one fusion protein, wherein the fusion protein comprises a CRISPR/Cas-like protein or a fragment thereof and an effector domain, and (b) at least one guide RNA or DNA encoding the guide RNA, wherein the guide RNA guides the CRISPR/Cas-like protein of the fusion protein to a targeted site in the chromosomal sequence and the effector domain of the fusion protein modifies the chromosomal sequence or regulates expression of the chromosomal sequence.

Fusion proteins comprising a CRISPR/Cas-like protein or a fragment thereof and an effector domain are detailed above in section (II). In general, the fusion proteins disclosed herein further comprise at least one nuclear localization signal. Nucleic acids encoding fusion proteins are described above in section (III). In some embodiments, the fusion protein can be introduced into the cell or embryo as an isolated protein (which can further comprise a cell-penetrating domain). Furthermore, the isolated fusion protein can be part of a protein-RNA complex comprising the guide RNA. In other embodiments, the fusion protein can be introduced into the cell or embryo as a RNA molecule (which can be capped and/or polyadenylated). In still other embodiments, the fusion protein can be introduced into the cell or embryo as a DNA molecule. For example, the fusion protein and the guide RNA can be introduced into the cell or embryo as discrete DNA molecules or as part of the same DNA molecule. Such DNA molecules can be plasmid vectors.

In some embodiments, the method further comprises introducing into the cell or embryo at least one zinc finger nuclease. Zinc finger nucleases are described above in section (II)(d). In still other embodiments, the method further comprises introducing into the cell or embryo at least one donor polynucleotide. Donor polynucleotides are detailed above in section (IV)(d). Means for introducing molecules into cells or embryos, as well as means for culturing cell or embryos are described above in sections (IV)(e) and (IV)(f), respectively. Suitable cells and embryos are described above in section (IV)(g).

In certain embodiments in which the effector domain of the fusion protein is a cleavage domain (e.g., a FokI cleavage domain or a modified FokI cleavage domain), the method can comprise introducing into the cell or embryo one fusion protein (or nucleic acid encoding one fusion protein) and two guide RNAs (or DNA encoding two guide RNAs). The two guide RNAs direct the fusion protein to two different target sites in the chromosomal sequence, wherein the fusion protein dimerizes (e.g., form a homodimer) such that the two cleavage domains can introduce a double stranded break into the chromosomal sequence. See FIG. 1A. In embodiments in which the optional donor polynucleotide is not present, the double-stranded break in the chromosomal sequence can be repaired by a non-homologous end-joining (NHEJ) repair process. Because NHEJ is error-prone, deletions of at least one nucleotide, insertions of at least one nucleotide, substitutions of at least one nucleotide, or combinations thereof can occur during the repair of the break. Accordingly, the targeted chromosomal sequence can be modified or inactivated. For example, a single nucleotide change (SNP) can give rise to an altered protein product, or a shift in the reading frame of a coding sequence can inactivate or "knock out" the sequence such that no protein product is made. In embodiments in which the optional donor polynucleotide is present, the donor sequence in the donor polynucleotide can be exchanged with or integrated into the chromosomal sequence at the targeted site during repair of the double-stranded break. For example, in embodiments in which the donor sequence is flanked by upstream and downstream sequences having substantial sequence identity with upstream and downstream sequences, respectively, of the targeted site in the chromosomal sequence, the donor sequence can be exchanged with or integrated into the chromosomal sequence at the targeted site during repair mediated by homology-directed repair process. Alternatively, in embodiments in which the donor sequence is flanked by compatible overhangs (or the compatible overhangs are generated in situ by the RNA-guided endonuclease) the donor sequence can be ligated directly with the cleaved chromosomal sequence by a non-homologous repair process during repair of the double-stranded break. Exchange or integration of the donor sequence into the chromosomal sequence modifies the targeted chromosomal sequence or introduces an exogenous sequence into the chromosomal sequence of the cell or embryo.

In other embodiments in which the effector domain of the fusion protein is a cleavage domain (e.g., a FokI cleavage domain or a modified FokI cleavage domain), the method can comprise introducing into the cell or embryo two different fusion proteins (or nucleic acid encoding two different fusion proteins) and two guide RNAs (or DNA encoding two guide RNAs). The fusion proteins can differ as detailed above in section (II). Each guide RNA directs a fusion protein to a specific target site in the chromosomal sequence, wherein the fusion proteins dimerize (e.g., form a heterodimer) such that the two cleavage domains can introduce a double stranded break into the chromosomal sequence. In embodiments in which the optional donor polynucleotide is not present, the resultant double-stranded breaks can be repaired by a non-homologous repair process such that deletions of at least one nucleotide, insertions of at least one nucleotide, substitutions of at least one nucleotide, or combinations thereof can occur during the repair of the break. In embodiments in which the optional donor polynucleotide is present, the donor sequence in the donor polynucleotide can be exchanged with or integrated into the chromosomal sequence during repair of the double-stranded break by either a homology-based repair process (e.g., in embodiments in which the donor sequence is flanked by upstream and downstream sequences having substantial sequence identity with upstream and downstream sequences, respectively, of the targeted sites in the chromosomal sequence) or a non-homologous repair process (e.g., in embodiments in which the donor sequence is flanked by compatible overhangs).

Figure 1B:
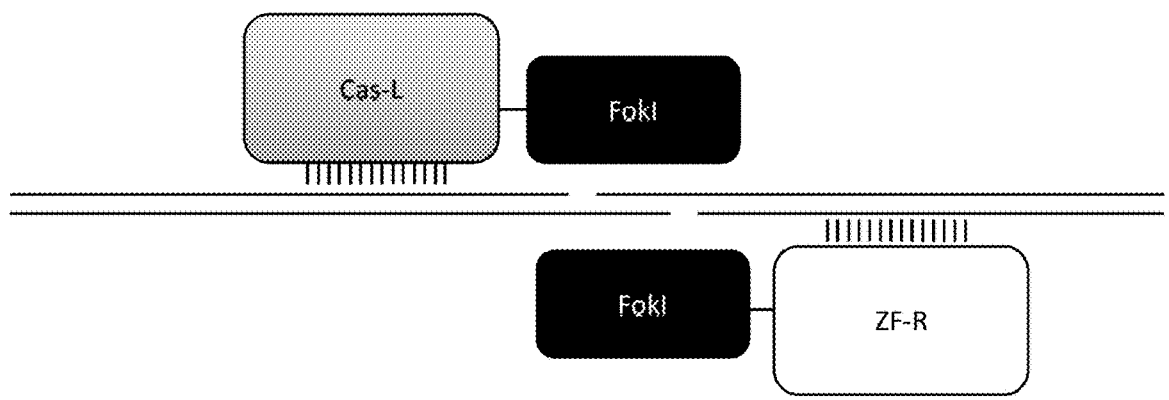
FIG. 1B depicts a double stranded break created by a dimer composed of a fusion protein comprising a Cas-like protein and a FokI cleavage domain and a zinc finger nuclease comprising a zinc finger (ZF) DNA-binding domain and a FokI cleavage domain.

In still other embodiments in which the effector domain of the fusion protein is a cleavage domain (e.g., a FokI cleavage domain or a modified FokI cleavage domain), the method can comprise introducing into the cell or embryo one fusion protein (or nucleic acid encoding one fusion protein), one guide RNA (or DNA encoding one guide RNA), and one zinc finger nuclease (or nucleic acid encoding the zinc finger nuclease), wherein the zinc finger nuclease comprises a FokI cleavage domain or a modified FokI cleavage domain. The guide RNA directs the fusion protein to a specific chromosomal sequence, and the zinc finger nuclease is directed to another chromosomal sequence, wherein the fusion protein and the zinc finger nuclease dimerize such that the cleavage domain of the fusion protein and the cleavage domain of the zinc finger nuclease can introduce a double stranded break into the chromosomal sequence. See FIG. 1B. In embodiments in which the optional donor polynucleotide is not present, the resultant double-stranded breaks can be repaired by a non-homologous repair process such that deletions of at least one nucleotide, insertions of at least one nucleotide, substitutions of at least one nucleotide, or combinations thereof can occur during the repair of the break. In embodiments in which the optional donor polynucleotide is present, the donor sequence in the donor polynucleotide can be exchanged with or integrated into the chromosomal sequence during repair of the double-stranded break by either a homology-based repair process (e.g., in embodiments in which the donor sequence is flanked by upstream and downstream sequences having substantial sequence identity with upstream and downstream sequences, respectively, of the targeted sites in the chromosomal sequence) or a non-homologous repair process (e.g., in embodiments in which the donor sequence is flanked by compatible overhangs).

Figure 2A:
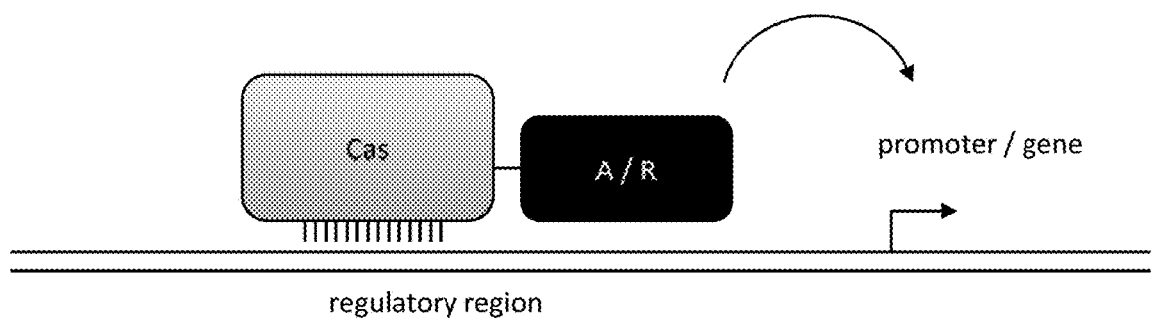
FIG. 2A illustrates regulation of gene expression using RNA-guided fusion proteins comprising a Cas-like protein used for DNA binding and an "A/R" domain that activates or represses gene expression.

In still other embodiments in which the effector domain of the fusion protein is a transcriptional activation domain or a transcriptional repressor domain, the method can comprise introducing into the cell or embryo one fusion protein (or nucleic acid encoding one fusion protein) and one guide RNA (or DNA encoding one guide RNA). The guide RNA directs the fusion protein to a specific chromosomal sequence, wherein the transcriptional activation domain or a transcriptional repressor domain activates or represses expression, respectively, of the targeted chromosomal sequence. See FIG. 2A.

Figure 2B:
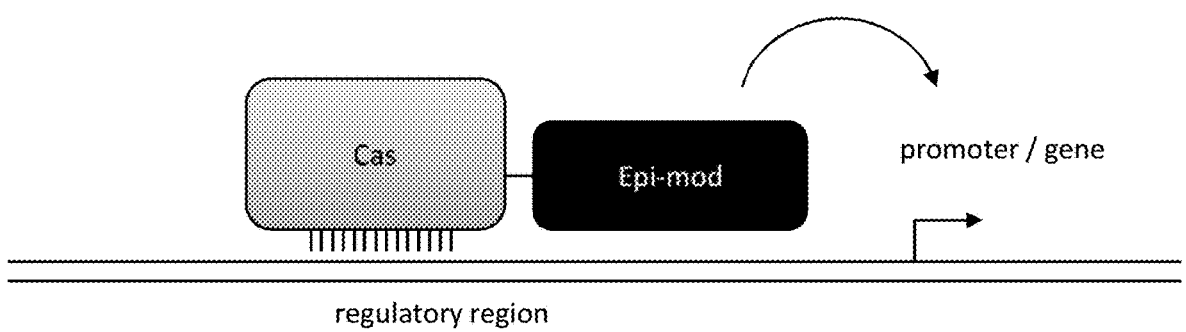
FIG. 2B diagrams a fusion protein comprising a Cas-like protein for DNA binding and a epigenetic modification domain ("Epi-mod") that affects epigenetic states by covalent modification of proximal DNA or proteins.

In alternate embodiments in which the effector domain of the fusion protein is an epigenetic modification domain, the method can comprise introducing into the cell or embryo one fusion protein (or nucleic acid encoding one fusion protein) and one guide RNA (or DNA encoding one guide RNA). The guide RNA directs the fusion protein to a specific chromosomal sequence, wherein the epigenetic modification domain modifies the structure of the targeted the chromosomal sequence. See FIG. 2B. Epigenetic modifications include acetylation, methylation of histone proteins and/or nucleotide methylation. In some instances, structural modification of the chromosomal sequence leads to changes in expression of the chromosomal sequence.

(VI) Genetically Modified Cells and Animals

The present disclosure encompasses genetically modified cells, non-human embryos, and non-human animals comprising at least one chromosomal sequence that has been modified using an RNA-guided endonuclease-mediated or fusion protein-mediated process, for example, using the methods described herein. The disclosure provides cells comprising at least one DNA or RNA molecule encoding an RNA-guided endonuclease or fusion protein targeted to a chromosomal sequence of interest or a fusion protein, at least one guide RNA, and optionally one or more donor polynucleotide(s). The disclosure also provides non-human embryos comprising at least one DNA or RNA molecule encoding an RNA-guided endonuclease or fusion protein targeted to a chromosomal sequence of interest, at least one guide RNA, and optionally one or more donor polynucleotide(s).

The present disclosure provides genetically modified non-human animals, non-human embryos, or animal cells comprising at least one modified chromosomal sequence. The modified chromosomal sequence may be modified such that it is (1) inactivated, (2) has an altered expression or produces an altered protein product, or (3) comprises an integrated sequence. The chromosomal sequence is modified with an RNA guided endonuclease-mediated or fusion protein-mediated process, using the methods described herein.

As discussed, one aspect of the present disclosure provides a genetically modified animal in which at least one chromosomal sequence has been modified. In one embodiment, the genetically modified animal comprises at least one inactivated chromosomal sequence. The modified chromosomal sequence may be inactivated such that the sequence is not transcribed and/or a functional protein product is not produced. Thus, a genetically modified animal comprising an inactivated chromosomal sequence may be termed a "knock out" or a "conditional knock out." The inactivated chromosomal sequence can include a deletion mutation (i.e., deletion of one or more nucleotides), an insertion mutation (i.e., insertion of one or more nucleotides), or a nonsense mutation (i.e., substitution of a single nucleotide for another nucleotide such that a stop codon is introduced). As a consequence of the mutation, the targeted chromosomal sequence is inactivated and a functional protein is not produced. The inactivated chromosomal sequence comprises no exogenously introduced sequence. Also included herein are genetically modified animals in which two, three, four, five, six, seven, eight, nine, or ten or more chromosomal sequences are inactivated.

In another embodiment, the modified chromosomal sequence can be altered such that it codes for a variant protein product. For example, a genetically modified animal comprising a modified chromosomal sequence can comprise a targeted point mutation(s) or other modification such that an altered protein product is produced. In one embodiment, the chromosomal sequence can be modified such that at least one nucleotide is changed and the expressed protein comprises one changed amino acid residue (missense mutation). In another embodiment, the chromosomal sequence can be modified to comprise more than one missense mutation such that more than one amino acid is changed. Additionally, the chromosomal sequence can be modified to have a three nucleotide deletion or insertion such that the expressed protein comprises a single amino acid deletion or insertion. The altered or variant protein can have altered properties or activities compared to the wild type protein, such as altered substrate specificity, altered enzyme activity, altered kinetic rates, etc.

In another embodiment, the genetically modified animal can comprise at least one chromosomally integrated sequence. A genetically modified animal comprising an integrated sequence may be termed a "knock in" or a "conditional knock in." The chromosomally integrated sequence can, for example, encode an orthologous protein, an endogenous protein, or combinations of both. In one embodiment, a sequence encoding an orthologous protein or an endogenous protein can be integrated into a chromosomal sequence encoding a protein such that the chromosomal sequence is inactivated, but the exogenous sequence is expressed. In such a case, the sequence encoding the orthologous protein or endogenous protein may be operably linked to a promoter control sequence. Alternatively, a sequence encoding an orthologous protein or an endogenous protein may be integrated into a chromosomal sequence without affecting expression of a chromosomal sequence. For example, a sequence encoding a protein can be integrated into a "safe harbor" locus, such as the Rosa26 locus, HPRT locus, or AAV locus. The present disclosure also encompasses genetically modified animals in which two, three, four, five, six, seven, eight, nine, or ten or more sequences, including sequences encoding protein(s), are integrated into the genome.

The chromosomally integrated sequence encoding a protein can encode the wild type form of a protein of interest or can encode a protein comprising at least one modification such that an altered version of the protein is produced. For example, a chromosomally integrated sequence encoding a protein related to a disease or disorder can comprise at least one modification such that the altered version of the protein produced causes or potentiates the associated disorder. Alternatively, the chromosomally integrated sequence encoding a protein related to a disease or disorder can comprise at least one modification such that the altered version of the protein protects against the development of the associated disorder.

In an additional embodiment, the genetically modified animal can be a "humanized" animal comprising at least one chromosomally integrated sequence encoding a functional human protein. The functional human protein can have no corresponding ortholog in the genetically modified animal. Alternatively, the wild type animal from which the genetically modified animal is derived may comprise an ortholog corresponding to the functional human protein. In this case, the orthologous sequence in the "humanized" animal is inactivated such that no functional protein is made and the "humanized" animal comprises at least one chromosomally integrated sequence encoding the human protein.

In yet another embodiment, the genetically modified animal can comprise at least one modified chromosomal sequence encoding a protein such that the expression pattern of the protein is altered. For example, regulatory regions controlling the expression of the protein, such as a promoter or a transcription factor binding site, can be altered such that the protein is over-produced, or the tissue-specific or temporal expression of the protein is altered, or a combination thereof. Alternatively, the expression pattern of the protein can be altered using a conditional knockout system. A non-limiting example of a conditional knockout system includes a Cre-lox recombination system. A Cre-lox recombination system comprises a Cre recombinase enzyme, a site-specific DNA recombinase that can catalyze the recombination of a nucleic acid sequence between specific sites (lox sites) in a nucleic acid molecule. Methods of using this system to produce temporal and tissue specific expression are known in the art. In general, a genetically modified animal is generated with lox sites flanking a chromosomal sequence. The genetically modified animal comprising the lox-flanked chromosomal sequence can then be crossed with another genetically modified animal expressing Cre recombinase. Progeny animals comprising the lox-flanked chromosomal sequence and the Cre recombinase are then produced, and the lox-flanked chromosomal sequence is recombined, leading to deletion or inversion of the chromosomal sequence encoding the protein. Expression of Cre recombinase can be temporally and conditionally regulated to effect temporally and conditionally regulated recombination of the chromosomal sequence.

In any of these embodiments, the genetically modified animal disclosed herein can be heterozygous for the modified chromosomal sequence. Alternatively, the genetically modified animal can be homozygous for the modified chromosomal sequence.

The genetically modified animals disclosed herein can be crossbred to create animals comprising more than one modified chromosomal sequence or to create animals that are homozygous for one or more modified chromosomal sequences. For example, two animals comprising the same modified chromosomal sequence can be crossbred to create an animal homozygous for the modified chromosomal sequence. Alternatively, animals with different modified chromosomal sequences can be crossbred to create an animal comprising both modified chromosomal sequences.

For example, a first animal comprising an inactivated chromosomal sequence gene "x" can be crossed with a second animal comprising a chromosomally integrated sequence encoding a human gene "X" protein to give rise to "humanized" gene "X" offspring comprising both the inactivated gene "x" chromosomal sequence and the chromosomally integrated human gene "X" sequence. Also, a humanized gene "X" animal can be crossed with a humanized gene "Y" animal to create humanized gene X/gene Y offspring. Those of skill in the art will appreciate that many combinations are possible.

In other embodiments, an animal comprising a modified chromosomal sequence can be crossbred to combine the modified chromosomal sequence with other genetic backgrounds. By way of non-limiting example, other genetic backgrounds may include wild-type genetic backgrounds, genetic backgrounds with deletion mutations, genetic backgrounds with another targeted integration, and genetic backgrounds with non-targeted integrations.

The term "animal," as used herein, refers to a non-human animal. The animal may be an embryo, a juvenile, or an adult. Suitable animals include vertebrates such as mammals, birds, reptiles, amphibians, shellfish, and fish. Examples of suitable mammals include without limit rodents, companion animals, livestock, and primates. Non-limiting examples of rodents include mice, rats, hamsters, gerbils, and guinea pigs. Suitable companion animals include but are not limited to cats, dogs, rabbits, hedgehogs, and ferrets. Non-limiting examples of livestock include horses, goats, sheep, swine, cattle, llamas, and alpacas. Suitable primates include but are not limited to capuchin monkeys, chimpanzees, lemurs, macaques, marmosets, tamarins, spider monkeys, squirrel monkeys, and vervet monkeys. Non-limiting examples of birds include chickens, turkeys, ducks, and geese. Alternatively, the animal may be an invertebrate such as an insect, a nematode, and the like. Non-limiting examples of insects include *Drosophila* and mosquitoes. An exemplary animal is a rat. Non-limiting examples of suitable rat strains include Dahl Salt-Sensitive, Fischer 344, Lewis, Long Evans Hooded, Sprague-Dawley, and Wistar. In one embodiment, the animal is not a genetically modified mouse. In each of the foregoing iterations of suitable animals for the invention, the animal does not include exogenously introduced, randomly integrated transposon sequences.

A further aspect of the present disclosure provides genetically modified cells or cell lines comprising at least one modified chromosomal sequence. The genetically modified cell or cell line can be derived from any of the genetically modified animals disclosed herein. Alternatively, the chromosomal sequence can be modified in a cell as described herein above (in the paragraphs describing chromosomal sequence modifications in animals) using the methods descried herein. The disclosure also encompasses a lysate of said cells or cell lines.

In general, the cells are eukaryotic cells. Suitable host cells include fungi or yeast, such as *Pichia, Saccharomyces*, or *Schizosaccharomyces*; insect cells, such as SF9 cells from *Spodoptera frugiperda* or S2 cells from *Drosophila melanogaster*; and animal cells, such as mouse, rat, hamster, non-human primate, or human cells. Exemplary cells are mammalian. The mammalian cells can be primary cells. In general, any primary cell that is sensitive to double strand breaks may be used. The cells may be of a variety of cell types, e.g., fibroblast, myoblast, T or B cell, macrophage, epithelial cell, and so forth.

When mammalian cell lines are used, the cell line can be any established cell line or a primary cell line that is not yet described. The cell line can be adherent or non-adherent, or the cell line can be grown under conditions that encourage adherent, non-adherent or organotypic growth using standard techniques known to individuals skilled in the art. Non-limiting examples of suitable mammalian cells and cell lines are provided herein in section (IV)(g). In still other embodiments, the cell can be a stem cell. Non-limiting examples of suitable stem cells are provided in section (IV)(g).

The present disclosure also provides a genetically modified non-human embryo comprising at least one modified chromosomal sequence. The chromosomal sequence can be modified in an embryo as described herein above (in the paragraphs describing chromosomal sequence modifications in animals) using the methods descried herein. In one embodiment, the embryo is a non-human fertilized one-cell stage embryo of the animal species of interest. Exemplary mammalian embryos, including one cell embryos, include without limit, mouse, rat, hamster, rodent, rabbit, feline, canine, ovine, porcine, bovine, equine, and primate embryos.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As used herein, the term "endogenous sequence" refers to a chromosomal sequence that is native to the cell.

The term "exogenous," as used herein, refers to a sequence that is not native to the cell, or a chromosomal sequence whose native location in the genome of the cell is in a different chromosomal location.

A "gene," as used herein, refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The term "heterologous" refers to an entity that is not endogenous or native to the cell of interest. For example, a heterologous protein refers to a protein that is derived from or was originally derived from an exogenous source, such as an exogenously introduced nucleic acid sequence. In some instances, the heterologous protein is not normally produced by the cell of interest.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The terms "polypeptide" and "protein" are used interchangeably to refer to a polymer of amino acid residues.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the GenBank website.

As various changes could be made in the above-described cells and methods without departing from the scope of the invention, it is intended that all matter contained in the above description and in the examples given below, shall be interpreted as illustrative and not in a limiting sense.

EXAMPLES

The following examples illustrate certain aspects of the invention.

Example 1: Modification of Cas9 Gene for Mammalian Expression

A Cas9 gene from *Streptococcus pyogenes* strain MGAS 15252 (Accession number YP_005388840.1) was optimized with *Homo sapiens* codon preference to enhance its translation in mammalian cells. The Cas9 gene also was modified by adding a nuclear localization signal PKKKRKV (SEQ ID NO: 1) at the C terminus for targeting the protein into the nuclei of mammalian cells. Table 1 presents the modified Cas9 amino acid sequence, with the nuclear localization sequence underlined. Table 2 presents the codon optimized, modified Cas9 DNA sequence.

TABLE 1

Modified Cas9 Amino Acid Sequence (SEQ ID NO: 9)
MDKKYSIGLDIGTNSVGWAVITDDYKVPSKKFKVLGNTDRHSIKK

NLIGALLFGSGETAEATRLKRTARRRYTRRKNRICYLQEIFSNEM

AKVDDSFFHRLEESFLVEEDKKHERHPIFGNIVDEVAYHEKYPTI

TABLE 1-continued

Modified Cas9 Amino Acid Sequence

YHLRKKLADSTDKADLRLIYLALAHMIKFRGHFLIEGDLNPDNSD
VDKLFIQLVQIYNQLFEENPINASRVDAKAILSARLSKSRRLENL
IAQLPGEKRNGLFGNLIALSLGLTPNFKSNFDLAEDAKLQLSKDT
YDDDLDNLLAQIGDQYADLFLAAKNLSDAILLSDILRVNSEITKA
PLSASMIKRYDEHHQDLTLLKALVRQQLPEKYKEIFFDQSKNGYA
GYIDGGASQEEFYKFIKPILEKMDGTEELLVKLNREDLLRKQRTF
DNGSIPHQIHLGELHAILRRQEDFYPFLKDNREKIEKILTFRIPY
YVGPLARGNSRFAWMTRKSEETITPWNFEEWDKGASAQSFIERMT
NFDKNLPNEKVLPKHSLLYEYFTVYNELTKVKYVTEGMRKPAFLS
GEQKKAIVDLLFKTNRKVTVKQLKEDYFKKIECFDSVEISGVEDR
FNASLGAYHDLLKIIKDKDFLDNEENEDILEDIVLTLTLFEDRGM
IEERLKTYAHLFDDKVMKQLKRRRYTGWGRLSRKLINGIRDKQSG
KTILDFLKSDGFANRNFMQLIHDDSLTFKEDIQKAQVSGQGHSLH
EQIANLAGSPAIKKGILQTVKIVDELVKVMGHKPENIVIEMAREN
QTTQKGQKNSRERMKRIEEGIKELGSQILKEHPVENTQLQNEKLY
LYYLQNGRDMYVDQELDINRLSDYDVDHIVPQSFIKDDSIDNKVL
TRSDKNRGKSDNVPSEEVVKKMKNYWRQLLNAKLITQRKFDNLTK
AERGGLSELDKAGFIKRQLVETRQITKHVAQILDSRMNTKYDEND
KLIREVKVITLKSKLVSDFRKDFQFYKVREINNYHHAHDAYLNAV
VGTALIKKYPKLESEFVYGDYKVYDVRKMIAKSEQEIGKATAKYF
FYSNIMNFFKTEITLANGEIRKRPLIETNGETGEIVWDKGRDFAT
VRKVLSMPQVNIVKKTEVQTGGFSKESILPKRNSDKLIARKKDWD
PKKYGGFDSPTVAYSVLVVAKVEKGKSKKLKSVKELLGITIMERS
SFEKNPIDFLEAKGYKEVKKDLIIKLPKYSLFELENGRKRMLASA
GELQKGNELALPSKYVNFLYLASHYEKLKGSPEDNEQKQLFVEQH
KHYLDEIIEQISEFSKRVILADANLDKVLSAYNKHRDKPIREQAE
NIIHLFTLTNLGAPAAFKYFDTTIDRKRYTSTKEVLDATLIHQSI
TGLYETRIDLSQLGGDPKKKRKV

TABLE 2

Optimized Cas9 DNA Sequence (5'-3')

(SEQ ID NO: 10)
ATGGACAAGAAGTACAGCATCGGCCTGGACATCGGCACCAACTCTGTGG
GCTGGGCCGTGATCACCGACGACTACAAGGTGCCCAGCAAGAAATTCAA
GGTGCTGGGCAACACCGACCGGCACAGCATCAAGAAGAACCTGATCGGC
GCCCTGCTGTTCGGCTCTGGCGAAACAGCCGAGGCCACCCGGCTGAAGA
GAACCGCCAGAAGAAGATACACCAGACGGAAGAACCGGATCTGCTATCT
GCAAGAGATCTTCAGCAACGAGATGGCCAAGGTGGACGACAGCTTCTTC
CACAGACTGGAAGAGTCCTTCCTGGTGGAAGAGGATAAGAAGCACGAGC

TABLE 2-continued

Optimized Cas9 DNA Sequence (5'-3')

GGCACCCCATCTTCGGCAACATCGTGGACGAGGTGGCCTACCACGAGAA
GTACCCCACCATCTACCACCTGAGAAAGAAGCTGGCCGACAGCACCGAC
AAGGCCGACCTGAGACTGATCTACCTGGCCCTGGCCCACATGATCAAGT
TCCGGGGCCACTTCCTGATCGAGGGCGACCTGAACCCCGACAACAGCGA
CGTGGACAAGCTGTTCATCCAGCTGGTGCAGATCTACAATCAGCTGTTC
GAGGAAAACCCCATCAACGCCAGCAGAGTGGACGCCAAGGCCATCCTGA
GCGCCAGACTGAGCAAGAGCAGACGGCTGGAAAATCTGATCGCCCAGCT
GCCCGGCGAGAAGCGGAATGGCCTGTTCGGCAACCTGATTGCCCTGAGC
CTGGGCCTGACCCCCAACTTCAAGAGCAACTTCGACCTGGCCGAGGATG
CCAAACTGCAGCTGAGCAAGGACACCTACGACGACGACCTGGACAACCT
GCTGGCCCAGATCGGCGACCAGTACGCCGACCTGTTTCTGGCCGCCAAG
AACCTGTCCGACGCCATCCTGCTGAGCGACATCCTGAGAGTGAACAGCG
AGATCACCAAGGCCCCCCTGTCCGCCTCTATGATCAAGAGATACGACGA
GCACCACCAGGACCTGACCCTGCTGAAAGCTCTCGTGCGGCAGCAGCTG
CCTGAGAAGTACAAAGAGATTTTCTTCGACCAGAGCAAGAACGGCTACG
CCGGCTACATCGATGGCGGAGCCAGCCAGGAAGAGTTCTACAAGTTCAT
CAAGCCCATCCTGGAAAAGATGGACGGCACCGAGGAACTGCTCGTGAAG
CTGAACAGAGAGGACCTGCTGCGGAAGCAGCGGACCTTCGACAACGGCA
GCATCCCCCACCAGATCCACCTGGGAGAGCTGCACGCCATTCTGCGGCG
GCAGGAAGATTTTTACCCATTCCTGAAGGACAACCGGGAAAAGATCGAG
AAGATCCTGACCTTCAGAATCCCCTACTACGTGGGCCCTCTGGCCAGGG
GAAACAGCAGATTCGCCTGGATGACCAGAAAGAGCGAGGAAACCATCAC
CCCCTGGAACTTCGAGGAAGTGGTGGACAAGGGCGCCAGCGCCCAGAGC
TTCATCGAGCGGATGACCAACTTCGATAAGAACCTGCCCAACGAGAAGG
TGCTGCCCAAGCACAGCCTGCTGTACGAGTACTTCACCGTGTACAACGA
GCTGACCAAAGTGAAATACGTGACCGAGGGAATGCGGAAGCCCGCCTTT
CTGAGCGGCGAGCAGAAAAAGGCCATCGTGGACCTGCTGTTCAAGACCA
ACCGGAAAGTGACCGTGAAGCAGCTGAAAGAGGACTACTTCAAGAAAAT
CGAGTGCTTCGACAGCGTGGAAATCAGCGGCGTGGAAGATCGGTTCAAC
GCCTCCCTGGGCGCCTATCACGATCTGCTGAAAATTATCAAGGACAAGG
ACTTCCTGGACAATGAGGAAAACGAGGACATTCTGGAAGATATCGTGCT
GACCCTGACACTGTTTGAGGACCGGGGCATGATCGAGGAACGGCTGAAA
ACCTATGCCCACCTGTTCGACGACAAAGTGATGAAGCAGCTGAAGCGGC
GGAGATACACCGGCTGGGGCAGGCTGAGCCGGAAGCTGATCAACGGCAT
CCGGGACAAGCAGTCCGGCAAGACAATCCTGGATTTCCTGAAGTCCGAC
GGCTTCGCCAACAGAAACTTCATGCAGCTGATCCACGACGACAGCCTGA
CCTTTAAAGAGGACATCCAGAAAGCCCAGGTGTCCGGCCAGGGACACTC
TCTGCACGAGCAGATCGCCAATCTGGCCGGATCCCCCGCCATTAAGAAG
GGCATCCTGCAGACAGTGAAGATTGTGGACGAGCTCGTGAAAGTGATGG

TABLE 2-continued

Optimized Cas9 DNA Sequence (5'-3')

GCCACAAGCCCGAGAACATCGTGATCGAAATGGCCAGAGAGAACCAGAC

CACCCAGAAGGGACAGAAGAACAGCCGCGAGAGAATGAAGCGGATCGAA

GAGGGCATCAAAGAGCTGGGCAGCCAGATCCTGAAAGAACACCCCGTGG

AAAACACCCAGCTGCAGAACGAGAAGCTGTACCTGTACTACCTGCAGAA

TGGGCGGGATATGTACGTGGACCAGGAACTGGACATCAACCGGCTGTCC

GACTACGATGTGGACCACATTGTGCCCCAGTCCTTCATCAAGGACGACT

CCATCGATAACAAAGTGCTGACTCGGAGCGACAAGAACCGGGGCAAGAG

CGACAACGTGCCCTCCGAAGAGGTCGTGAAGAAGATGAAGAACTACTGG

CGCCAGCTGCTGAATGCCAAGCTGATTACCCAGAGGAAGTTCGACAATC

TGACCAAGGCCGAGAGAGGCGGCCTGAGCGAACTGGATAAGGCCGGCTT

CATTAAGCGGCAGCTGGTGGAAACCCGGCAGATCACAAAGCACGTGGCA

CAGATCCTGGACTCCCGGATGAACACTAAGTACGACGAGAACGACAAAC

TGATCCGGGAAGTGAAAGTGATCACCCTGAAGTCCAAGCTGGTGTCCGA

CTTCAGAAAGGATTTCCAGTTTTACAAAGTGCGCGAGATCAACAACTAC

CACCACGCCCACGACGCCTACCTGAACGCCGTCGTGGGAACCGCCCTGA

TCAAAAAGTACCCTAAGCTGGAAAGCGAGTTCGTGTACGGCGATTACAA

GGTGTACGACGTGCGGAAGATGATCGCCAAGAGCGAGCAGGAAATCGGC

AAGGCTACCGCCAAGTACTTCTTCTACAGCAACATCATGAACTTTTTCA

AGACCGAGATCACACTGGCCAACGGCGAGATCAGAAAGCGGCCTCTGAT

CGAGACAAACGGCGAAACCGGGGAGATCGTGTGGGATAAGGGCCGGGAT

TTTGCCACAGTGCGGAAAGTGCTGTCCATGCCCCAAGTGAATATCGTGA

AAAAGACCGAGGTGCAGACCGGCGGCTTCAGCAAAGAGTCTATCCTGCC

CAAGAGGAACTCCGACAAGCTGATCGCCAGAAAGAAGGATTGGGACCCT

AAGAAGTACGGCGGCTTTGACAGCCCCACCGTGGCCTACTCTGTGCTGG

TGGTGGCCAAAGTGGAAAAGGGCAAGTCCAAGAAACTGAAGAGTGTGAA

AGAGCTGCTGGGGATCACCATCATGGAAAGAAGCAGCTTCGAGAAGAAT

CCCATCGACTTTCTGGAAGCCAAGGGCTACAAAGAAGTGAAAAAGGACC

TGATCATCAAGCTGCCTAAGTACTCCCTGTTCGAGCTGGAAAACGGCCG

GAAGCGGATGCTGGCTTCTGCCGGCGAACTGCAGAAGGGAAACGAGCTG

GCCCTGCCCTCCAAATATGTGAACTTCCTGTACCTGGCCAGCCACTATG

AGAAGCTGAAGGGCTCCCCCGAGGATAATGAGCAGAAACAGCTGTTTGT

GGAACAGCACAAGCACTACCTGGACGAGATCATCGAGCAGATTAGCGAG

TTCTCCAAGCGCGTGATCCTGGCCGATGCCAACCTGGACAAGGTGCTGA

GCGCCTACAACAAGCACCGGGATAAGCCCATCAGAGAGCAGGCCGAGAA

TATCATCCACCTGTTTACCCTGACCAACCTGGGAGCCCCTGCCGCCTTC

AAGTACTTTGACACCACCATCGACCGGAAGAGGTACACCAGCACCAAAG

AGGTGCTGGACGCCACCCTGATCCACCAGAGCATCACCGGCCTGTACGA

GACACGGATCGACCTGTCTCAGCTGGGAGGCGACCCCAAGAAAAAGCGC

AAAGTG

The modified Cas9 DNA sequence was placed under the control of cytomegalovirus (CMV) promoter for constituent expression in mammalian cells. The modified Cas9 DNA sequence was also placed under the control T7 promoter for in vitro mRNA synthesis with T7 RNA polymerase. In vitro RNA transcription was performed by using MessageMAX T7 ARCA-Capped Message Transcription Kit and T7 mScript Standard mRNA Production System (Cellscript).

Example 2: Targeting Cas9

The adeno-associated virus integration site 1 (AAVS1) locus was used as a target for Cas9-mediated human genome modification. The human AAVS1 locus is located in intron 1 (4427 bp) of protein phosphatase 1, regulatory subunit 12C (PPP1R12C). Table 3 presents the first exon (shaded gray) and the first intron of PPP1R12C. The underlined sequence within the intron is the targeted modification site (i.e., AAVS1 locus).

TABLE 3

First Exon and Intron of PPP1R12C (5'-3')

(SEQ ID NO: 11)
GCGGGCGGGCGGTGCGATGTCCGGAGAGGCTGGCCCGGCGGCTGGCCCGG

GGGCGGCGGCGGCGGCTGCCCGGGAGCGGCGACGGGAGCAGCTGCGGCAG

TGGGGGCGCGGGCGGGCGCCGAGCCTGGCCCCGGAGAGCGCCGCGCCCG

CACCGTCCGCTTCGAGCGCGCCGCCGAGTTCCTGGCGCCTGTGCGGGCGG

CGAACCTGGACGAGGCGCGTCTGATGCTGCGCGCCGCCGACCCTGGCCCCG

GCGCCGAGCTCGACCCCGCCGCGCCGCCGCCCGCCGCGCCGTGCTGGAC

TCCACCAACGCCGACGGTATCAGCGCCCTGCACCAGGTCAGCGCCCCCCG

CCCGGCGTCTCCCGGGGCCAGGTCCACCCTCTGCTGCGCCACCTGGGGCA

TCCTCCTTCCCCGTTGCCAGTCTCGATCCGCCCCGTCGTTCCTGGCCCTG

GGCTTTGCCACCCTATGCTGACACCCCGTCCCAGTCCCCCTTACCATTCC

CCTTCGACCACCCCACTTCCGAATTGGAGCCGCTTCAACTGGCCCTGGGC

TTAGCCACTCTGTGCTGACCACTCTGCCCCAGGCCTCCTTACCATTCCCC

TTCGACCTACTCTCTTCCGCATTGGAGTCGCTTTAACTGGCCCTGGCTTT

GGCAGCCTGTGCTGACCCATGCAGTCCTCCTTACCATCCCTCCCTCGACT

TCCCCTCTTCCGATGTTGAGCCCCTCCAGCCGGTCCTGGACTTTGTCTCC

TTCCCTGCCCTGCCCTCTCCTGAACCTGAGCCAGCTCCCATAGCTCAGTC

TGGTCTATCTGCCTGGCCCTGGCCATTGTCACTTTGCGCTGCCCTCCTCT

CGCCCCGAGTGCCCTTGCTGTGCCGCCGGAACTCTGCCCTCTAACGCTG

CCGTCTCTCTCCTGAGTCCGGACCACTTTGAGCTCTACTGGCTTCTGCGC

TABLE 3-continued

First Exon and Intron of PPP1R12C (5'-3')

CGCCTCTGGCCCACTGTTTCCCCTTCCCAGGCAGGTCCTGCTTTCTCTGA
CCTGCATTCTCTCCCCTGGGCCTGTGCCGCTTTCTGTCTGCAGCTTGTGG
CCTGGGTCACCTCTACGGCTGGCCCAGATCCTTCCCTGCCGCCTCCTTCA
GGTTCCGTCTTCCTCCACTCCCTCTTCCCCTTGCTCTCTGCTGTGTTGCT
GCCCAAGGATGCTCTTTCCGGAGCACTTCCTTCTCGGCGCTGCACCACGT
GATGTCCTCTGAGCGGATCCTCCCCGTGTCTGGGTCCTCTCCGGGCATCT
CTCCTCCCTCACCCAACCCCATGCCGTCTTCACTCGCTGGGTTCCCTTTT
CCTTCTCCTTCTGGGGCCTGTGCCATCTCTCGTTTCTTAGGATGGCCTTC
TCCGACGGATGTCTCCCTTGCGTCCCGCCTCCCCTTCTTGTAGGCCTGCA
TCATCACCGTTTTTCTGGACAACCCCAAAGTACCCCGTCTCCCTGGCTTT
AGCCACCTCTCCATCCTCTTGCTTTCTTTGCCTGGACACCCCGTTCTCCT
GTGGATTCGGGTCACCTCTCACTCCTTTCATTTGGGCAGCTCCCCTACCC
CCCTTACCTCTCTAGTCTGTGCTAGCTCTTCCAGCCCCCTGTCATGGCAT
CTTCCAGGGGTCCGAGAGCTCAGCTAGTCTTCTTCCTCCAACCCGGGCCC
CTATGTCCACTTCAGGACAGCATGTTTGCTGCCTCCAGGGATCCTGTGTC
CCCGAGCTGGGACCACCTTATATTCCCAGGGCCGGTTAATGTGGCTCTGG
TTCTGGGTACTTTTATCTGTCCCCTCC<u>ACCCCACAGTGGGGCCACTAGG</u>G
ACAGGATTGGTGACAGAAAAGCCCCATCCTTAGGCCTCCTCCTTCCTAGT
CTCCTGATATTGGGTCTAACCCCCACCTCCTGTTAGGCAGATTCCTTATC
TGGTGACACACCCCCATTTCCTGGAGCCATCTCTCTCCTTGCCAGAACCT
CTAAGGTTTGCTTACGATGGAGCCAGAGAGGATCCTGGGAGGGAGAGCTT
GGCAGGGGTGGGAGGGAAGGGGGGGATGCGTGACCTGCCCGGTTCTCAG
TGGCCACCCTGCGCTACCCTCTCCCAGAACCTGAGCTGCTCTGACGCGGC
CGTCTGGTGCGTTTCACTGATCCTGGTGCTGCAGCTTCCTTACACTTCCC
AAGAGGAGAAGCAGTTTGGAAAAACAAAATCAGAATAAGTTGGTCCTGAG
TTCTAACTTTGGCTCTTCACCTTTCTAGTCCCAATTTATATTGTTCCTC
CGTGCGTCAGTTTTACCTGTGAGATAAGGCCAGTAGCCAGCCCCGTCCTG
GCAGGGCTGTGGTGAGGAGGGGGTGTCCGTGTGGAAAACTCCCTTGTG
AGAATGGTGCGTCCTAGGTGTTCACCAGGTCGTGGCCGCCTCTACTCCCT
TTCTCTTTCTCCATCCTTCTTTCCTTAAAGAGTCCCCAGTGCTATCTGGG
ACATATTCCTCCGCCCAGAGCAGGGTCCCGCTTCCCTAAGGCCCTGCTCT
GGGCTTCTGGGTTTGAGTCCTTGGCAAGCCCAGGAGAGGCGCTCAGGCTT
CCCTGTCCCCCTTCCTCGTCCACCATCTCATGCCCCTGGCTCTCCTGCCC
CTTCCCTACAGGGGTTCCTGGCTCTGCTCTTCAGACTGAGCCCCGTTCCC
CTGCATCCCCGTTCCCCTGCATCCCCCTTCCCCTGCATCCCCAGAGGCC
CCAGGCCACCTACTTGGCCTGGACCCCACGAGAGGCCACCCCAGCCCGT
CTACCAGGCTGCCTTTTGGGTGGATTCTCCTCCAACTGTGGGGTGACTGC
TTGGCAAACTCACTCTTCGGGGTATCCCAGGAGGCCTGGAGCATTGGGGT
GGGCTGGGGTTCAGAGAGGAGGGATTCCCTTCTCAGGTTACGTGGCCAAG

AAGCAGGGGAGCTGGGTTTGGGTCAGGTCTGGGTGTGGGGTGACCAGCTT
ATGCTGTTTGCCCAGGACAGCCTAGTTTTAGCACTGAAACCCTCAGTCCT
AGGAAAACAGGGATGGTTGGTCACTGTCTCTGGGTGACTCTTGATTCCCG
GCCAGTTTCTCCACCTGGGGCTGTGTTTCTCGTCCTGCATCCTTCTCCAG
GCAGGTCCCCAAGCATCGCCCCCCTGCTGTGGCTGTTCCCAAGTTCTTAG
GGTACCCCACGTGGGTTTATCAACCACTTGGTGAGGCTGGTACCCTGCCC
CCATTCCTGCACCCCAATTGCCTTAGTGGCTAGGGGGTTGGGGGCTAGAG
TAGGAGGGGCTGGAGCCAGGATTCTTAGGGCTGAACAGAGAAGAGCTGGG
GGCCTGGGCTCCTGGGTTTGAGAGAGGAGGGGCTGGGGCCTGGACTCCTG
GGTCCGAGGGAGGAGGGGCTGGGGCCTGGACTCCTGGGTCTGAGGGTGGA
GGGACTGGGGCCTGGACTCCTGGGTCCGAGGGAGGAGGGGCTGGGGCCT
GGACTCGTGGGTCTGAGGGAGGAGGGGCTGGGGCCTGGACTTCTGGGTC
TTAGGGAGGCGGGGCTGGGCCTGGACCCCTGGGTCTGAATGGGGAGAGGC
TGGGGGCCTGGACTCCTTCATCTGAGGGCGGAAGGGCTGGGGCCTGGCCT
CCTGGGTTGAATGGGGAGGGGTTGGGCCTGGACTCTGGAGTCCCTGGTGC
CCAGGCCTCAGGCATCTTTCACAGGGATGCCTGTACTGGGCAGGTCCTTG
AAAGGGAAAGGCCCATTGCTCTCCTTGCCCCCCTCCCCTATCGCCATGAC
AACTGGGTGGAAATAAACGAGCCGAGTTCATCCCGTTCCCAGGGCACGTG
CGGCCCCTTCACAGCCCGAGTTTCCATGACCTCATGCTCTTGGCCCTCGT
AGCTCCCTCCCGCCTCCTCCAGATGGGCAGCTTTGGAGAGGTGAGGGACT
TGGGGGGTAATTTATCCCGTGGATCTAGGAGTTTAGCTTCACTCCTTCCT
CAGCTCCAGTTCAGGTCCCGGAGCCCACCCAGTGTCCACAAGGCCTGGGG
CAAGTCCTCCTCCGACCCCCTGGACTTCGGCTTTTGTCCCCCCAAGTTT
TGGACCCCTAAGGGAAGAATGAGAAACGGTGGCCCGTGTCAGCCCCTGGC
TGCAGGGCCCCGTGCAGAGGGGGCCTCAGTGAACTGGAGTGTGACAGCCT
GGGGCCCAGGCACACAGGTGTGCAGCTGTCTCACCCCTCTGGGAGTCCCG
CCCAGGCCCCTGAGTCTGTCCCAGCACAGGGTGGCCTTCCTCCACCCTGC
ATAGCCCTGGGCCCACGGCTTCGTTCCTGCAGAGTATCTGCTGGGGTGGT
TTCCGAGCTTGACCCTTGGAAGGACCTGGCTGGGTTTAAGGCAGGAGGGG
CTGGGGCCAGGACTCCTGGCTCTGAAGGAGGAGGGGCTGGAACCTCTTC
CCTAGTCTGAGCACTGGAAGCGCCACCTGTGGGTGGTGACGGGGGTTTTG
CCGTGTCTAACAGGTACCATGTGGGGTTCCCGCACCCAGATGAGAAGCCC
CCTCCCTTCCCCGTTCACTTCCTGTTTGCAGATAGCCAGGAGTCCTTTCG
TGGTTTCCACTGAGCACTGAAGGCCTGGCCGGCCTGACCACTGGGCAACC
AGGCGTATCTTAAACAGCCAGTGGCCAGAGGCTGTTGGGTCATTTTCCCC
ACTGTCCTAGCACCGTGTCCCTGGATCTGTTTTCGTGGCTCCCTCTGGAG
TCCCGACTTGCTGGGACACCGTGGCTGGGGTAGGTGCGGCTGACGGCTGT
TTCCCACCCCCAG

Cas9 guide RNAs were designed for targeting the human AAVS1 locus. A 42 nucleotide RNA (referred to herein as a "crRNA" sequence) comprising (5' to 3') a target recognition sequence (i.e., sequence complementary to the non-coding strand of the target sequence) and protospacer sequence; a 85 nucleotide RNA (referred to herein as a "tracrRNA" sequence) comprising 5' sequence with complementarity to the 3' sequence of the crRNA and additional hairpin sequence; and a chimeric RNA comprising nucleotides 1-32 of the crRNA, a GAAA loop, and nucleotides 19-45 of the tracrRNA were prepared. The crRNA was chemically synthesized by Sigma-Aldrich. The tracrRNA and chimeric RNA were synthesized by in vitro transcription with T7 RNA polymerase using T7-Scribe Standard RNA IVT Kit (Cellscript). The chimeric RNA coding sequence was also placed under the control of human U6 promoter for in vivo transcription in human cells. Table 4 presents the sequences of the guide RNAs.

TABLE 4

Guide RNAs

| RNA | 5'-3' Sequence | SEQ ID NO: |
|---|---|---|
| AAVS1-crRNA | ACCCCACAGUGGGGCCACUAG UUUUAGAGCUAUGCUGUUUUG | 12 |
| tracrRNA | GGAACCAUUCAAAACAGCAUA GCAAGUUAAAAUAAGGCUAGU CCGUUAUCAACUUGAAAAAGU GGCACCGAGUCGGUGCUUUUU UU | 13 |
| chimeric RNA | ACCCCACAGUGGGGCCACUAG UUUUAGAGCUAGAAAUAGCAA GUUAAAAUAAGGCUAGUCCG | 14 |

Example 3: Preparation of Donor Polynucleotide to Monitor Genome Modification

Targeted integration of a GFP protein into the N terminus of PPP1R12C was used to monitor Cas9-mediated genome modification. To mediate integration by homologous recombination a donor polynucleotide was prepared. The AAVS1-GFP DNA donor contained a 5' (1185 bp) AAVS1 locus homologous arm, an RNA splicing receptor, a turbo GFP coding sequence, a 3' transcription terminator, and a 3' (1217 bp) AAVS1 locus homologous arm. Table 5 presents the sequences of the RNA splicing receptor and the GFP coding sequence followed by the 3' transcription terminator. Plasmid DNA was prepared by using GenElute Endotoxin-Free Plasmid Maxiprep Kit (Sigma).

TABLE 5

Sequences in the AAVS1-GFP DNA donor sequence

| | 5'-3' Sequence | SEQ ID NO: |
|---|---|---|
| RNA splicing receptor | CTGACCTCTTCTCTTCCTCCCACAG | 15 |
| GFP coding sequence and transcription terminator | GCCACCATGGACTACAAAGACGATG ACGACAAGGTCGACTCTAGAGCTGC AGAGAGCGACGAGAGCGGCCTGCCC GCCATGGAGATCGAGTGCCGCATCA CCGGCACCCTGAACGGCGTGGAGTT CGAGCTGGTGGGCGGCGGAGAGGGC | 16 |

TABLE 5-continued

Sequences in the AAVS1-GFP DNA donor sequence

| 5'-3' Sequence | SEQ ID NO: |
|---|---|
| ACCCCCGAGCAGGGCCGCATGACCA ACAAGATGAAGAGCACCAAAGGCGC CCTGACCTTCAGCCCCTACCTGCTG AGCCACGTGATGGGCTACGGCTTCT ACCACTTCGGCACCTACCCCAGCGG CTACGAGAACCCCTTCCTGCACGCC ATCAACAACGGCGGCTACACCAACA CCCGCATCGAGAAGTACGAGGACGG CGGCGTGCTGCACGTGAGCTTCAGC TACCGCTACGAGGCCGGCCGCGTGA TCGGCGACTTCAAGGTGATGGGCAC CGGCTTCCCCGAGGACAGCGTGATC TTCACCGACAAGATCGTCCGCAGCA ACGCCACCGTGGAGCACCTGCACCC CATGGGCGATAACGATCTGGATGGC AGCTTCACCCGCACCTTCAGCCTGC GCGACGGCGGCTACTACAGCTCCGT GGTGGACAGCCACATGCACTTCAAG AGCGCCATCCACCCCAGCATCCTGC AGAACGGGGGCCCCATGTTCGCCTT CCGCCGCGTGGAGGAGGATCACAGC AACACCGAGCTGGGCATCGTGGAGT ACCAGCACGCCTTCAAGACCCCGGA TGCAGATGCCGGTGAAGAATGAAGA TCTCTGTGCCTTCTAGTTGCCAGCC ATCTGTTGTTTGCCCCTCCCCCGTG CCTTCCTTGACCCTGGAAGGTGCCA CTCCCACTGTCCTTTCCTAATAAAA TGAGGAAATTGCATCGCATTGTCTG AGTAGGTGTCATTCTATTCTGGGGG GTGGGGTGGGGCAGGACAGCAAGGG GGAGGATTGGGAAGACAATAGCAGG CATGCTGGGGATGCGGTGGGCTCTA TGGACTCGAGGTTTAAACGTCGACG CGGCCGCGT | |

Targeted gene integration will result in a fusion protein between the first 107 amino acids of the PPP1R12C and the turbo GFP. The expected fusion protein contains the first 107 amino acid residues of PPP1R12C (highlighted in grey) from RNA splicing between the first exon of PPP1R12C and the engineered splice receptor (see Table 6).

TABLE 6

Predicted amino acid sequence of the PPP1R12C-GFP fusion protein.

(SEQ ID NO: 17)
MSGEDGPAAGPGAAAAAARERRREQLRQWGARAGAEPGPGERRARTVRFE

RAAEPLAACAGGDLDEARLMLRAADPGPGAELDPAAPPPARAVLDSTNAD

GISALHQATMDYKDDDDKVDSRAAESDESGLPAMEIECRITGTLNGVEFE

LVGGGEGTPEQGRMTNKMKSTKGALTFSPYLLSHVMGYGFYHFGTYPSGY

ENPFLHAINNGGYTNTRIEKYEDGGVLHVSFSYRYEAGRVIGDFKVMGTG

FPEDSVIFTDKIVRSNATVEHLHPMGDNDLDGSFTRTFSLRDGGYYSSWD

SHMHFKSAIHPSILQNGGPMFAFRRVEEDHSNTELGIVEYQHAFKTPDAD

AGEE

Example 4: Cas9-Mediated Targeted Integration

Transfection was performed on human K562 cells. The K562 cell line was obtained from American Type Culture Collection (ATCC) and grown in Iscove's Modified Dulbecco's Medium, supplemented with 10% FBS and 2 mM L-glutamine. All media and supplements were obtained from Sigma-Aldrich. Cultures were split one day before transfection (at approximately 0.5 million cells per mL before transfection). Cells were transfected with Nucleofector Solution V (Lonza) on a Nucleofector (Lonza) with the T-016 program. Each nucleofection contained approximately 0.6 million cells. Transfection treatments are detailed in Table 7. Cells were grown at 37° C. and 5% $CO_2$ immediately after nucleofection.

TABLE 7

Transfection Treatments.

| Treatment | Modified Cas9 | Guide RNA | Donor sequence |
|---|---|---|---|
| A | Cas9 mRNA transcribed with an Anti-Reverse Cap Analog (10 µg) | pre-annealed crRNA-tracrRNA duplex (0.3 nmol) | AAVS1-GFP plasmid DNA (10 µg) |
| B | Cas9 mRNA transcribed with an Anti-Reverse Cap Analog (10 µg) | chimeric RNA (0.3 nmol) | AAVS1-GFP plasmid DNA (10 µg) |
| C | Cas9 mRNA capped via post-transcription capping reaction (10 µg) | chimeric RNA (0.3 nmol) | AAVS1-GFP plasmid DNA (10 µg) |
| D | Cas9 plasmid DNA (10 µg) | U6-chimeric RNA plasmid DNA (5 µg) | AAVS1-GFP plasmid DNA (10 µg) |
| E | None | None | AAVS1-GFP plasmid DNA (10 µg) |
| F | None | None | None |

Figure 4A:
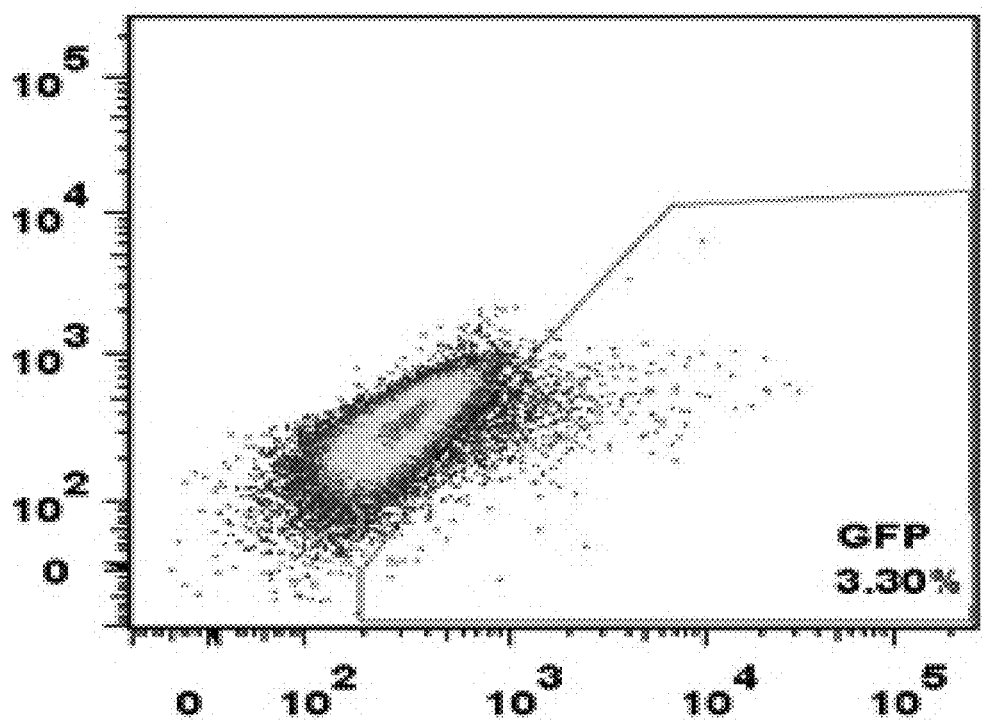
FIG. 4A-F present fluorescence-activated cell sorting (FACS) of human K562 cells transfected with Cas9 nucleic acid, Cas9 guiding RNA, and AAVS1-GFP DNA donor. The Y axis represents the auto fluorescence intensity at a red channel, and the X axis represents the green fluorescence intensity.
Figure 4B:
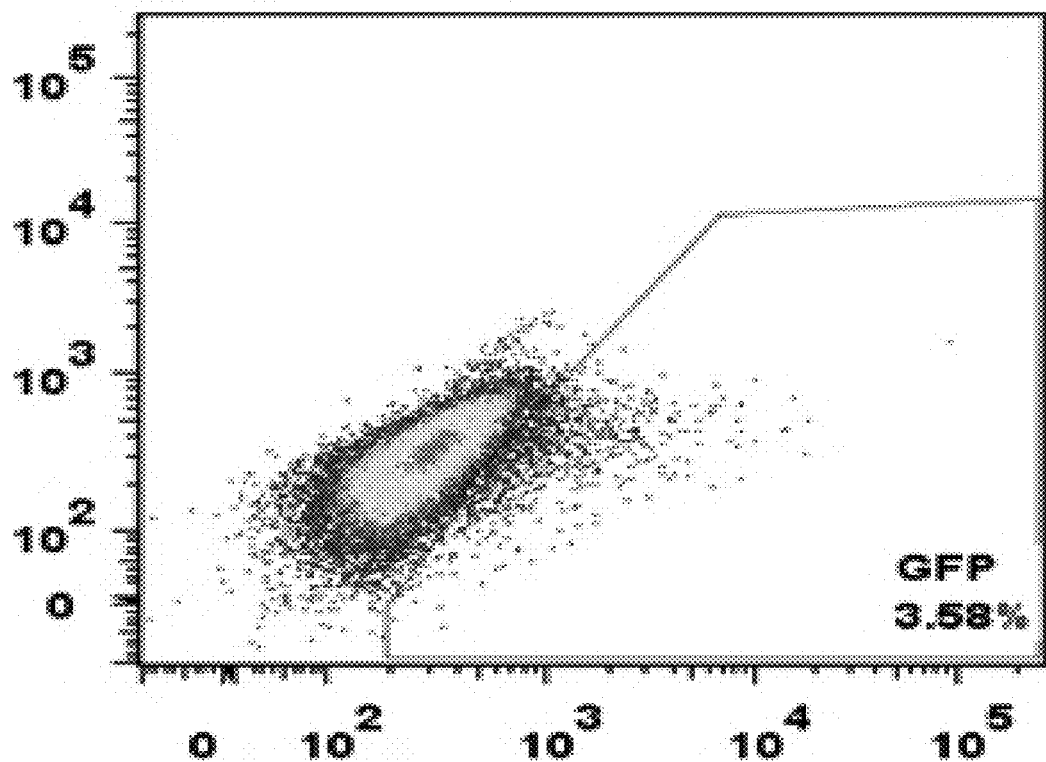
Figure 4C:
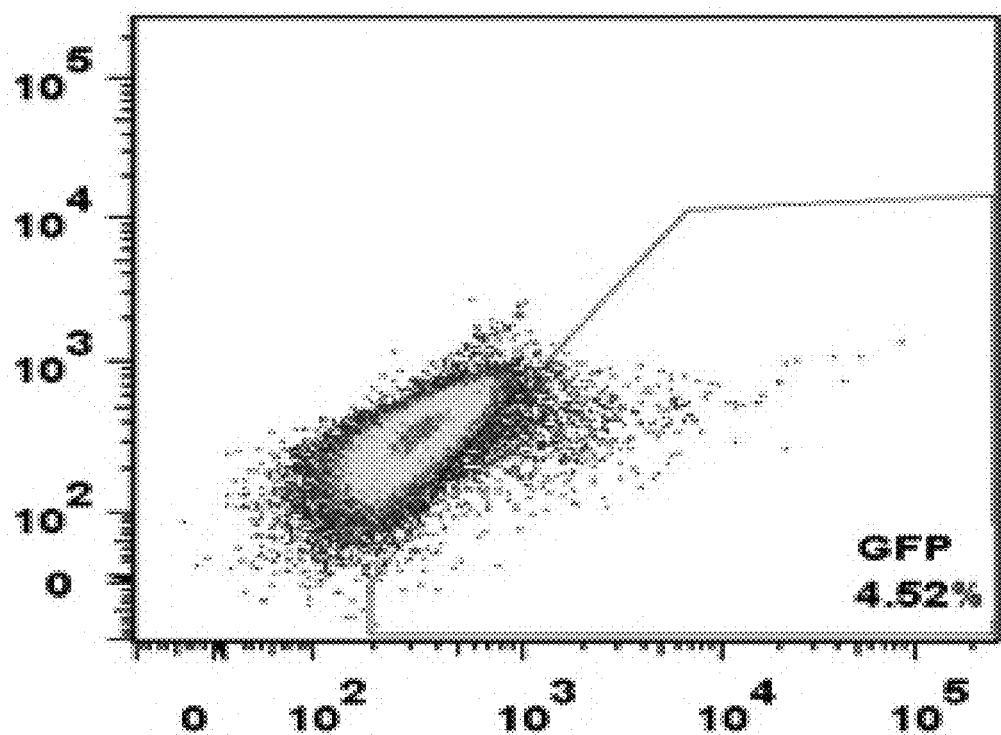
Figure 4D:
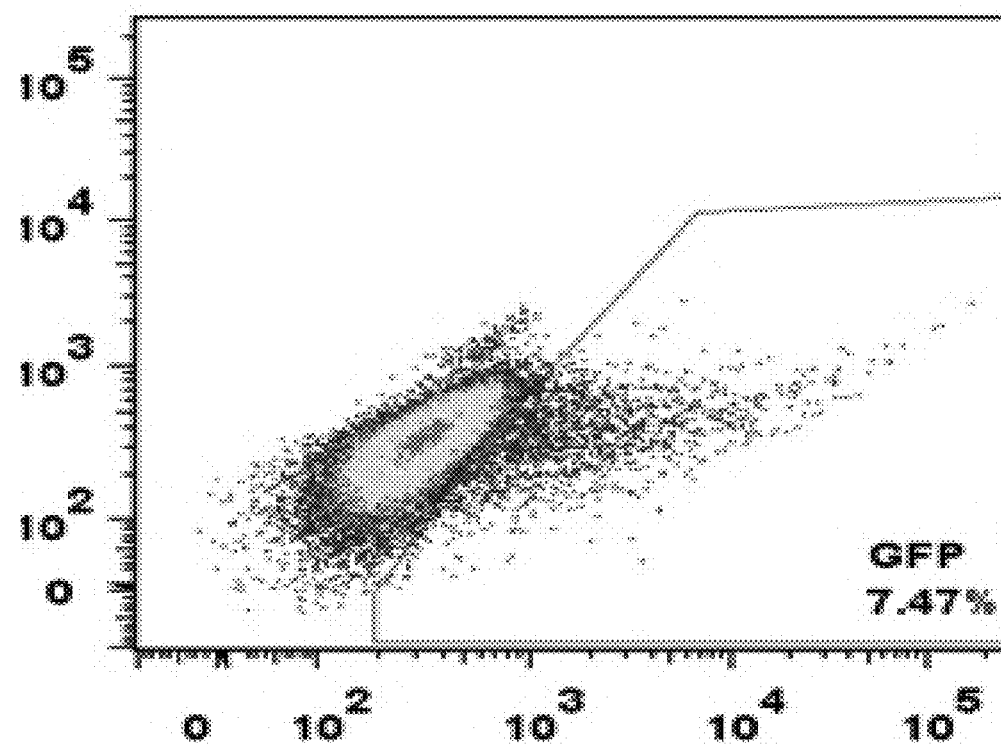
Figure 4E:
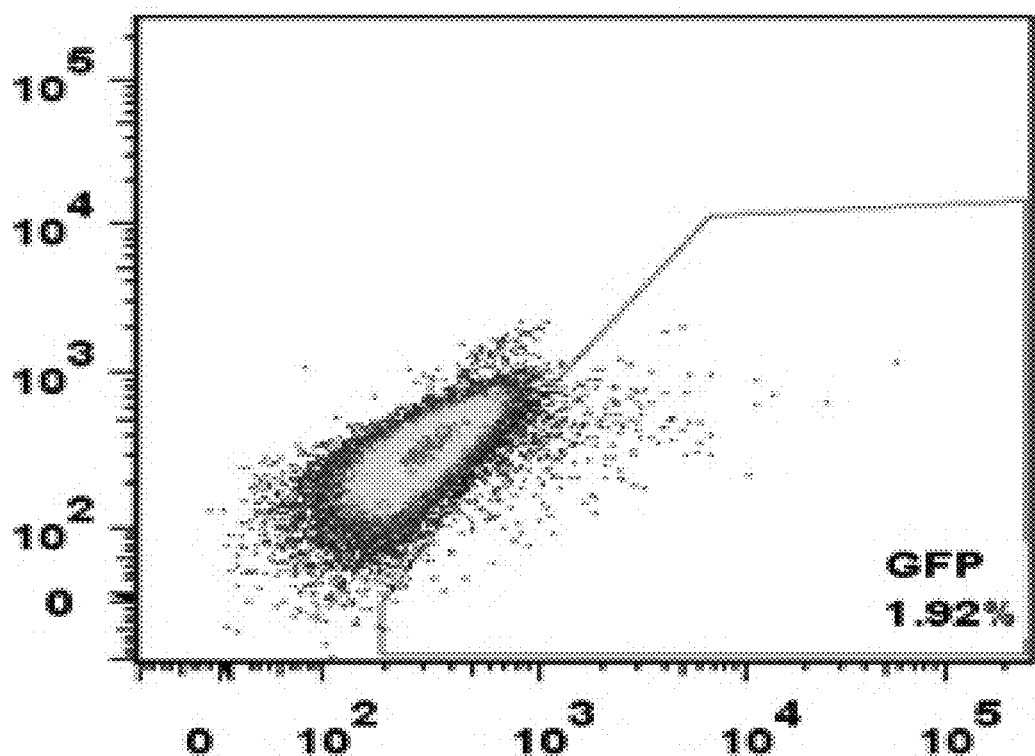
Figure 4F:
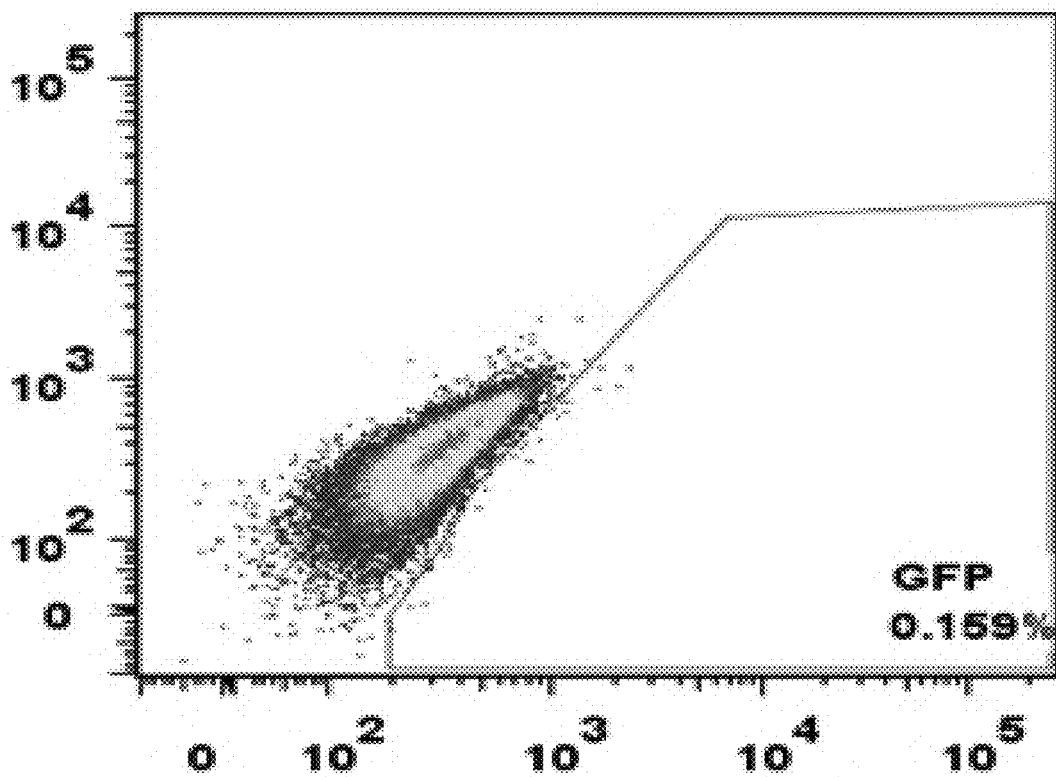

Fluorescence-activated cell sorting (FACS) was performed 4 days after transfection. FACS data are presented in FIGS. 4A-F. The percent GFP detected in each of the four experimental treatments (FIGS. 4A-D) was greater than in the control treatments (FIGS. 4E and 4F), confirming integration of the donor sequence and expression of the fusion protein.

Example 5: PCR Confirmation of Targeted Integration

Genomic DNA was extracted from transfected cells with GenElute Mammalian Genomic DNA Miniprep Kit (Sigma) 12 days after transfection. Genomic DNA was then PCR amplified with a forward primer located outside the 5' homologous arm of the AAVS1-GFP plasmid donor and a reverse primer located at the 5' region of the GFP. The forward primer was 5'-CCACTCTGTGCTGACCACTCT-3' (SEQ ID NO:18) and reverse primer was 5'-GCGGCACTC-GATCTCCA-3' (SEQ ID NO:19). The expected fragment size from the junction PCR was 1388 bp. The amplification was carried out with JumpStart Taq ReadyMix (Sigma), using the following cycling conditions: 98° C. for 2 minutes for initial denaturation; 35 cycles of 98° C. for 15 seconds, 62° C. for 30 seconds, and 72° C. for 1 minutes and 30 seconds; and a final extension at 72° C. for 5 minutes. PCR products were resolved on 1% agarose gel.

Figure 5:
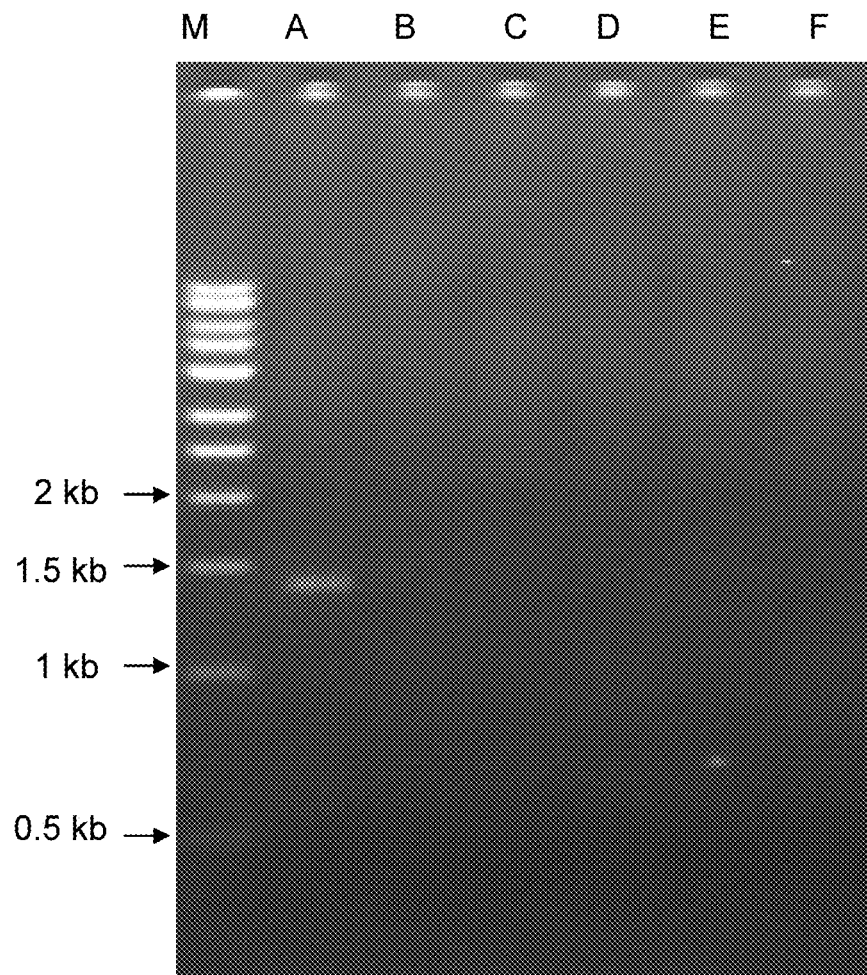
FIG. 5 presents a junction PCR analysis documenting the targeted integration of GFP into the AAVS1 locus in human cells. Lane M: 1 kb DNA molecular markers; Lane A: K562 cells transfected with 10 μg of Cas9 mRNA transcribed with an Anti-Reverse Cap Analog, 0.3 nmol of pre-annealed crRNA-tracrRNA duplex, and 10 μg of AAVS1-GFP plasmid DNA; Lane B: K562 cells transfected 10 μg of Cas9 mRNA transcribed with an Anti-Reverse Cap Analog, 0.3 nmol of chimeric RNA, and 10 μg of AAVS1-GFP plasmid DNA; Lane C: K562 cells transfected 10 μg of Cas9 mRNA that was capped by post-transcription capping reaction, 0.3 nmol of chimeric RNA, and 10 μg of AAVS1-GFP plasmid DNA; Lane D: K562 cells transfected with 10 μg of Cas9 plasmid DNA, 5 μg of U6-chimeric RNA plasmid DNA, and 10 μg of AAVS1-GFP plasmid DNA; Lane E: K562 cells transfected with 10 μg of AAVS1-GFP plasmid DNA; Lane F: K562 cells transfected with transfection reagents only.

Cells transfected with 10 µg of Cas9 mRNA transcribed with an Anti-Reverse Cap Analog, 0.3 nmol of pre-annealed crRNA-tracrRNA duplex, and 10 µg of AAVS1-GFP plasmid DNA displayed a PCR product of the expected size (see lane A in FIG. 5).

Example 6: Cas9-Based Genome Editing in Mouse Embryos

The mouse Rosa26 locus can be targeted for genome modifications. Table 8 presents a portion of the mouse Rosa26 sequence in which potential target sites are shown in bold. Each target site comprises a protospacer.

TABLE 8

Mouse Rosa26 Sequence (SEQ ID NO: 20)
GAGCGGCTGCGGGGCGGGTGCAAGCACGTTTCCGACTTGAGTTGCCTCA

AGAGGGGCGTGCTGAGCCAGACCTCCATCGCGCACTCCGGGGAGTGGAG

GGAAGGAGCGAGGGCTCAGTTGGGCTGTTTTGGAGGCAGGAAGCACTTG

CTCTCCCAAAGTCGCTCTGAGTTGTTATCAGTAAGGGAGCTGCAGTGGA

GTAGGCGGGAGAAGGCCGCACCCTTCTCCGGAGGGGGGAGGGGAGTGT

TGCAATACCTTTCTGGGAGTTCTCTGCTGCCTCCTGGCTTCTGAGGACC

GCCCTGGGCCTGGGAGAATCCCTTCCCCCTCTTCCCTCGTGATCTGCAA

CTCCAGTCTTTCTAGAAGATGGGCGGGAGTCTTCTGGGCAGGCTTAAAG

GCTAACCTGGTGTGTGGGCGTTGTCCTGCAGGGGAATTGAACAGGTGTA

AAATTGGAGGGACAAGACTTCCCACAGATTTTCGGTTTTGTCGGGAAGT

TTTTTAATAGGGGCAAATAAGGAAAATGGGAGGATAGGTAGTCATCTGG

GGTTTTATGCAGCAAAACTACAGGTTATTATTGCTTGTGATCCGCCTCG

GAGTATTTTCCATCGAGGTAGATTAAAGACATGCTCACCCGAGTTTTAT

ACTCTCCTGCTTGAGATCCTTACTACAGTATGAAATTACAGTGTCGCGA

GTTAGACTATGTAAGCAGAATTTTA

Guide RNAs were designed to target each of the target sites in the mouse Rosa26 locus. The sequences are shown in Table 9, each is 42 nucleotides in length and the 5' region is complementary to the strand that is not presented in Table 8 (i.e., the strand that is complementary to the strand shown in Table 8).

TABLE 9

Mouse Rosa26 Guide RNAs

| RNA | 5'-3' Sequence | SEQ ID NO: |
|---|---|---|
| mRosa26-crRNA-1 | CUCCAGUCUUUCUAGAAGAUG UUUUAGAGCUAUGCUGUUUUG | 21 |
| mRosa26-crRNA-2 | UGAACAGGUGUAAAAUUGGAG UUUUAGAGCUAUGCUGUUUUG | 22 |
| mRosa26-crRNA-3 | UGUCGGGAAGUUUUUUAAUAG UUUUAGAGCUAUGCUGUUUUG | 23 |

The crRNAs were chemically synthesized and pre-annealed to the tracrRNA (SEQ ID NO:13; see Example 2). Pre-annealed crRNA/tracrRNA and in vitro transcribed mRNA encoding modified Cas9 protein (SEQ ID NO. 9; see Example 1) can be microinjected into the pronuclei of fertilized mouse embryos. Upon guidance to the target set by the crRNA, the Cas9 protein cleaves the target site, and the resultant double-stranded break can be repaired via a non-homologous end-joining (NHEJ) repair process. The injected embryos can be either incubated at 37° C., 5% $CO_2$ overnight or for up to 4 days, followed by genotyping analysis, or the injected embryos can be implanted into recipient female mice such that live born animals can be genotyped. The in vitro-incubated embryos or tissues from live born animals can be screened for the presence of Cas9-induced mutation at the Rosa locus using standard methods. For example, the embryos or tissues from fetus or live-born animals can be harvested for DNA extraction and analysis. DNA can be isolated using standard procedures. The targeted region of the Rosa26 locus can be PCR amplified using appropriate primers. Because NHEJ is error-prone, deletions of at least one nucleotide, insertions of at least one nucleotide, substitutions of at least one nucleotide, or combinations thereof can occur during the repair of the break. Mutations can be detected using PCR-based genotyping methods, such as Cel-I mismatch assays and DNA sequencing.

Example 7: Cas9-Based Genome Modification in Mouse Embryos

The Rosa26 locus can be modified in mouse embryos by co-injecting a donor polynucleotide, as detailed above in section (IV)(d), along with the pre-annealed crRNA/tracrRNA and mRNA encoding modified Cas9 as described above in Example 6. In vitro-incubated embryos or tissues from live born animals (as described in Example 6) can be screened for a modified Rosa26 locus using PCR-based genotyping methods, such as RFLP assays, junction PCR, and DNA sequencing.

Example 8: Cas9-Based Genome Editing in Rat Embryos

The rat Rosa26 locus can be targeted for genome modifications. Table 10 presents a portion of the rat sequence in which potential target sites are shown in bold. Each target site comprises a protospacer.

TABLE 10

Rat Rosa26 Sequence (SEQ ID NO: 24)
GGGATTCCTCCTTGAGTTGTGGCACTGAGGAACGTGCTGAACAAGACCT

ACATTGCACTCCAGGGAGTGGATGAAGGAGTTGGGGCTCAGTCGGGTTG

TATTGGAGACAAGAAGCACTTGCTCTCCAAAAGTCGGTTTGAGTTATCA

TTAAGGGAGCTGCAGTGGAGTAGGCGGAGAAAAGGCCGCACCCTTCTCA

GGACGGGGGAGGGGAGTGTTGCAATACCTTTCTGGGAGTTCTCTGCTGC

CTCCTGTCTTCTGAGGACCGCCCTGGGCCTGGAAGATTCCCTTCCCCT

TCTTCCCTCGTGATCTGCAACTGGAGTCTTTCTGGAAGATAGGCGGGAG

TCTTCTGGGCAGGCTTAAAGGCTAACCTGGTGCGTGGGGCGTTGTCCTG

CAGAGGAATTGAACAGGTGTAAAATTGGAGGGGCAAGACTTCCCACAGA

TTTTCGATTGTGTTGTTAAGTATTGTAATAGGGGCAAATAAGGGAAATA

GACTAGGCACTCACCTGGGGTTTTATGCAGCAAAACTACAGGTTATTAT

TGCTTGTGATCCGCCCTGGAGAATTTTTCACCGAGGTAGATTGAAGACA

TGCCCACCCAAATTTTAATATTCTTCCACTTGCGATCCTTGCTACAGTA

TGAAA

Guide RNAs were designed to target each of the target sites in the rat Rosa26 locus. The sequences are shown in Table 11, each is 42 nucleotides in length and the 5' region is complementary to the strand that is not presented in Table 10 (i.e., the strand that is complementary to the strand shown in Table 10).

TABLE 11

Rat Rosa26 Guide RNAs

| RNA | 5'-3' Sequence | SEQ ID NO: |
|---|---|---|
| rRosa26-crRNA-1 | AGGGGGAAGGGAAUCUUCCAG UUUUAGAGCUAUGCUGUUUUG | 25 |
| rRosa26-crRNA-2 | UCUGCAACUGGAGUCUUUCUG UUUUAGAGCUAUGCUGUUUUG | 26 |
| rRosa26-crRNA-3 | AGGCGGGAGUCUUCUGGGCAG UUUUAGAGCUAUGCUGUUUUG | 27 |

The crRNAs were chemically synthesized and pre-annealed to the tracrRNA (SEQ ID NO:13; see Example 2). Pre-annealed crRNA/tracrRNA and in vitro transcribed mRNA encoding modified Cas9 protein (SEQ ID NO. 9; see Example 1) can be microinjected into the pronuclei of fertilized rat embryos. Upon guidance to the target site by the crRNA, the Cas9 protein cleaves the target site, and the resultant double-stranded break can be repaired via a non-homologous end-joining (NHEJ) repair process. The injected embryos can be either incubated at 37° C., 5% $CO_2$ overnight or for up to 4 days, followed by genotyping analysis, or the injected embryos can be implanted into recipient female mice such that live born animals can be genotyped. The in vitro-incubated embryos or tissues from live born animals can be screened for the presence of Cas9-induced mutation at the Rosa locus using standard methods. For example, the embryos or tissues from fetus or live-born animals can be harvested for DNA extraction and analysis. DNA can be isolated using standard procedures. The targeted region of the Rosa26 locus can be PCR amplified using appropriate primers. Because NHEJ is error-prone, deletions of at least one nucleotide, insertions of at least one nucleotide, substitutions of at least one nucleotide, or combinations thereof can occur during the repair of the break. Mutations can be detected using PCR-based genotyping methods, such as Cel-I mismatch assays and DNA sequencing.

Example 9: Cas9-Based Genome Modification in Rat Embryos

The Rosa26 locus can be modified in rat embryos by co-injecting a donor polynucleotide, as detailed above in section (IV)(d), along with the pre-annealed crRNA/tracrRNA and mRNA encoding modified Cas9 as described above in Example 8. In vitro-incubated embryos or tissues from live born rats (as described in Example 8) can be screened for a modified Rosa26 locus using PCR-based genotyping methods, such as RFLP assays, junction PCR, and DNA sequencing.

What is claimed is:

1. A method for modifying a chromosomal sequence in a eukaryotic cell, the method comprising:
   introducing into the eukaryotic cell
   (i) at least one RNA-guided endonuclease or nucleic acid encoding at least one RNA-guided endonuclease, wherein the at least one RNA-guided endonuclease is a clustered regularly interspersed short palindromic repeats (CRISPR)/CRISPR associated (Cas) (CRISPR-Cas) type II system protein,
   wherein the nucleic acid encoding the CRISPR-Cas type II system protein is codon optimized for expression in the eukaryotic cell,
   wherein the CRISPR-Cas type II system protein is a *Streptococcus pyogenes* Cas9 protein including at least one nuclear localization signal consisting of SEQ ID NO:1 or SEQ ID NO:2 covalently attached to the C-terminal amino acid of the Cas9 protein sequence; and
   (ii) at least one engineered guide RNA or DNA encoding at least one engineered guide RNA, each guide RNA comprising
   (1) a first region at the 5' end that base pairs with a target site in the chromosomal sequence, and
   (2) a second region that forms a secondary structure which interacts with the at least one RNA-guided endonuclease; and, optionally,
   (iii) at least one donor polynucleotide;
   whereby the at least one guide RNA guides the at least one RNA-guided endonuclease to the target site in the chromosomal sequence where the RNA-guided endonuclease introduces a double-stranded break, the target site in the chromosomal sequence is immediately followed by a protospacer adjacent motif (PAM), and repair of the double-stranded break by a DNA repair process leads to modification of the chromosomal sequence.

2. The method of claim 1, wherein the optional donor polynucleotide comprises a donor sequence that has at least one nucleotide change relative to the chromosomal sequence near the target site in the chromosomal sequence.

3. The method of claim 2, wherein the donor sequence is flanked by sequences having substantial sequence identity to sequences on either side of the target site in the chromosomal sequence.

4. The method of claim 2, wherein the donor sequence further comprises a targeted cleavage site that is recognized by the at least one RNA-guided endonuclease.

5. The method of claim 1, wherein the nucleic acid encoding the at least one RNA-guided endonuclease is mRNA.

6. The method of claim 1, wherein the nucleic acid encoding the at least one RNA-guided endonuclease is DNA.

7. The method of claim 1, wherein the eukaryotic cell is a human cell, a nonhuman mammalian cell, or a plant cell.

8. The method of claim 1, wherein the eukaryotic cell is in vitro.

9. The method of claim 1, wherein the eukaryotic cell is in vivo.

10. The method of claim 1, wherein the optional donor polynucleotide is not introduced into the eukaryotic cell, and repair of the double-stranded break by a non-homologous end-joining repair process results in inactivation of the chromosomal sequence.

11. The method of claim 1, wherein the optional donor polynucleotide is introduced into the eukaryotic cell, and repair of the double-stranded break results in a change of at least one nucleotide in the chromosomal sequence.

12. The method of claim 1, wherein the at least one guide RNA is at least partially chemically synthesized.

13. The method of claim 1, wherein only (i) and (ii) are introduced into the eukaryotic cell.

14. The method of claim 1, wherein (i), (ii), and (iii) are introduced into the eukaryotic cell.

15. The method of claim 1, wherein the Cas9 protein is from *Streptococcus pyogenes* strain MGAS15252 and comprises SEQ ID NO:9.

16. The method of claim 1, wherein the at least one nuclear localization signal covalently attached to the C-terminal amino acid of the Cas9 protein sequence consists of SEQ ID NO:1.

17. The method of claim 1, wherein the at least one nuclear localization signal covalently attached to the C-terminal amino acid of the Cas9 protein sequence consists of SEQ ID NO:2.

18. The method of claim 1, wherein the nucleic acid encoding the at least one RNA-guided endonuclease is mRNA and the at least one guide RNA is comprised of two non-covalently bound RNA molecules.

19. The method of claim 1, wherein the nucleic acid encoding the at least one RNA-guided endonuclease is mRNA and the at least one guide RNA is comprised of a single RNA molecule.

20. The method of claim 1, wherein the nucleic acid encoding the at least one RNA-guided endonuclease is DNA, the at least one guide RNA is encoded by DNA, and the at least one guide RNA is comprised of a single RNA molecule.

21. The method of claim 1, wherein the optional donor polynucleotide is double stranded DNA.

22. The method of claim 1, wherein the optional donor polynucleotide is single stranded DNA.

* * * * *

SEQUENCE LISTING

<160> NUMBER OF SEQ ID NOS: 27

<210> SEQ ID NO 1
<211> LENGTH: 7

```
<212> TYPE: PRT
<213> ORGANISM: Artificial Sequence
<220> FEATURE:
<223> OTHER INFORMATION: SYNTHESIZED

<400> SEQUENCE: 1

Pro Lys Lys Lys Arg Lys Val
1               5

<210> SEQ ID NO 2
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 2

Pro Lys Lys Lys Arg Arg Val
1               5

<210> SEQ ID NO 3
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 3

Lys Arg Pro Ala Ala Thr Lys Lys Ala Gly Gln Ala Lys Lys Lys Lys
1               5                   10                  15

<210> SEQ ID NO 4
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 4

Gly Arg Lys Lys Arg Arg Gln Arg Arg Pro Pro Gln Pro Lys Lys
1               5                   10                  15

Lys Arg Lys Val
            20

<210> SEQ ID NO 5
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 5

Pro Leu Ser Ser Ile Phe Ser Arg Ile Gly Asp Pro Pro Lys Lys Lys
1               5                   10                  15

Arg Lys Val

<210> SEQ ID NO 6
<211> LENGTH: 24
<212> TYPE: PRT
<213> ORGANISM: Artificial Sequence
<220> FEATURE:
<223> OTHER INFORMATION: SYNTHESIZED

<400> SEQUENCE: 6

Gly Ala Leu Phe Leu Gly Trp Leu Gly Ala Ala Gly Ser Thr Met Gly
1               5                   10                  15
```

```
Ala Pro Lys Lys Lys Arg Lys Val
            20

<210> SEQ ID NO 7
<211> LENGTH: 27
<212> TYPE: PRT
<213> ORGANISM: Artificial Sequence
<220> FEATURE:
<223> OTHER INFORMATION: SYNTHESIZED

<400> SEQUENCE: 7

Gly Ala Leu Phe Leu Gly Phe Leu Gly Ala Ala Gly Ser Thr Met Gly
1               5                   10                  15

Ala Trp Ser Gln Pro Lys Lys Arg Lys Val
            20                  25

<210> SEQ ID NO 8
<211> LENGTH: 21
<212> TYPE: PRT
<213> ORGANISM: Artificial Sequence
<220> FEATURE:
<223> OTHER INFORMATION: SYNTHESIZED

<400> SEQUENCE: 8

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 9
<211> LENGTH: 1374
<212> TYPE: PRT
<213> ORGANISM: Artificial Sequence
<220> FEATURE:
<223> OTHER INFORMATION: SYNTHESIZED

<400> SEQUENCE: 9

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Gly Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175
```

```
Asp Asn Ser Asp Val Asp Lys Leu Phe Ile Gln Leu Val Gln Ile Tyr
            180                 185                 190

Asn Gln Leu Phe Glu Glu Asn Pro Ile Asn Ala Ser Arg Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Arg Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Ala Tyr His Asp Leu Leu Lys Ile Ile Lys Asp Lys Asp Phe Leu Asp
```

-continued

|     |     | 595 |     |     |     | 600 |     |     |     | 605 |     |
|---|---|---|---|---|---|---|---|---|---|---|---|

Asn Glu Glu Asn Glu Asp Ile Leu Glu Asp Ile Val Leu Thr Leu Thr
610               615               620

Leu Phe Glu Asp Arg Gly Met Ile Glu Glu Arg Leu Lys Thr Tyr Ala
625               630               635               640

His Leu Phe Asp Asp Lys Val Met Lys Gln Leu Lys Arg Arg Arg Tyr
               645               650               655

Thr Gly Trp Gly Arg Leu Ser Arg Lys Leu Ile Asn Gly Ile Arg Asp
               660               665               670

Lys Gln Ser Gly Lys Thr Ile Leu Asp Phe Leu Lys Ser Asp Gly Phe
               675               680               685

Ala Asn Arg Asn Phe Met Gln Leu Ile His Asp Asp Ser Leu Thr Phe
690               695               700

Lys Glu Asp Ile Gln Lys Ala Gln Val Ser Gly Gln Gly His Ser Leu
705               710               715               720

His Glu Gln Ile Ala Asn Leu Ala Gly Ser Pro Ala Ile Lys Lys Gly
               725               730               735

Ile Leu Gln Thr Val Lys Ile Val Asp Glu Leu Val Lys Val Met Gly
               740               745               750

His Lys Pro Glu Asn Ile Val Ile Glu Met Ala Arg Glu Asn Gln Thr
               755               760               765

Thr Gln Lys Gly Gln Lys Asn Ser Arg Glu Arg Met Lys Arg Ile Glu
770               775               780

Glu Gly Ile Lys Glu Leu Gly Ser Gln Ile Leu Lys Glu His Pro Val
785               790               795               800

Glu Asn Thr Gln Leu Gln Asn Glu Lys Leu Tyr Leu Tyr Tyr Leu Gln
               805               810               815

Asn Gly Arg Asp Met Tyr Val Asp Gln Glu Leu Asp Ile Asn Arg Leu
               820               825               830

Ser Asp Tyr Asp Val Asp His Ile Val Pro Gln Ser Phe Ile Lys Asp
               835               840               845

Asp Ser Ile Asp Asn Lys Val Leu Thr Arg Ser Asp Lys Asn Arg Gly
850               855               860

Lys Ser Asp Asn Val Pro Ser Glu Glu Val Val Lys Lys Met Lys Asn
865               870               875               880

Tyr Trp Arg Gln Leu Leu Asn Ala Lys Leu Ile Thr Gln Arg Lys Phe
               885               890               895

Asp Asn Leu Thr Lys Ala Glu Arg Gly Gly Leu Ser Glu Leu Asp Lys
               900               905               910

Ala Gly Phe Ile Lys Arg Gln Leu Val Glu Thr Arg Gln Ile Thr Lys
               915               920               925

His Val Ala Gln Ile Leu Asp Ser Arg Met Asn Thr Lys Tyr Asp Glu
               930               935               940

Asn Asp Lys Leu Ile Arg Glu Val Lys Val Ile Thr Leu Lys Ser Lys
945               950               955               960

Leu Val Ser Asp Phe Arg Lys Asp Phe Gln Phe Tyr Lys Val Arg Glu
               965               970               975

Ile Asn Asn Tyr His His Ala His Asp Ala Tyr Leu Asn Ala Val Val
               980               985               990

Gly Thr Ala Leu Ile Lys Lys Tyr Pro Lys Leu Glu Ser Glu Phe Val
               995              1000             1005

Tyr Gly Asp Tyr Lys Val Tyr Asp Val Arg Lys Met Ile Ala Lys
             1010               1015             1020

Ser Glu Gln Glu Ile Gly Lys Ala Thr Ala Lys Tyr Phe Phe Tyr
1025            1030            1035

Ser Asn Ile Met Asn Phe Phe Lys Thr Glu Ile Thr Leu Ala Asn
1040            1045            1050

Gly Glu Ile Arg Lys Arg Pro Leu Ile Glu Thr Asn Gly Glu Thr
1055            1060            1065

Gly Glu Ile Val Trp Asp Lys Gly Arg Asp Phe Ala Thr Val Arg
1070            1075            1080

Lys Val Leu Ser Met Pro Gln Val Asn Ile Val Lys Lys Thr Glu
1085            1090            1095

Val Gln Thr Gly Gly Phe Ser Lys Glu Ser Ile Leu Pro Lys Arg
1100            1105            1110

Asn Ser Asp Lys Leu Ile Ala Arg Lys Lys Asp Trp Asp Pro Lys
1115            1120            1125

Lys Tyr Gly Gly Phe Asp Ser Pro Thr Val Ala Tyr Ser Val Leu
1130            1135            1140

Val Val Ala Lys Val Glu Lys Gly Lys Ser Lys Lys Leu Lys Ser
1145            1150            1155

Val Lys Glu Leu Leu Gly Ile Thr Ile Met Glu Arg Ser Ser Phe
1160            1165            1170

Glu Lys Asn Pro Ile Asp Phe Leu Glu Ala Lys Gly Tyr Lys Glu
1175            1180            1185

Val Lys Lys Asp Leu Ile Ile Lys Leu Pro Lys Tyr Ser Leu Phe
1190            1195            1200

Glu Leu Glu Asn Gly Arg Lys Arg Met Leu Ala Ser Ala Gly Glu
1205            1210            1215

Leu Gln Lys Gly Asn Glu Leu Ala Leu Pro Ser Lys Tyr Val Asn
1220            1225            1230

Phe Leu Tyr Leu Ala Ser His Tyr Glu Lys Leu Lys Gly Ser Pro
1235            1240            1245

Glu Asp Asn Glu Gln Lys Gln Leu Phe Val Glu Gln His Lys His
1250            1255            1260

Tyr Leu Asp Glu Ile Ile Glu Gln Ile Ser Glu Phe Ser Lys Arg
1265            1270            1275

Val Ile Leu Ala Asp Ala Asn Leu Asp Lys Val Leu Ser Ala Tyr
1280            1285            1290

Asn Lys His Arg Asp Lys Pro Ile Arg Glu Gln Ala Glu Asn Ile
1295            1300            1305

Ile His Leu Phe Thr Leu Thr Asn Leu Gly Ala Pro Ala Ala Phe
1310            1315            1320

Lys Tyr Phe Asp Thr Thr Ile Asp Arg Lys Arg Tyr Thr Ser Thr
1325            1330            1335

Lys Glu Val Leu Asp Ala Thr Leu Ile His Gln Ser Ile Thr Gly
1340            1345            1350

Leu Tyr Glu Thr Arg Ile Asp Leu Ser Gln Leu Gly Gly Asp Pro
1355            1360            1365

Lys Lys Lys Arg Lys Val
1370

<210> SEQ ID NO 10
<211> LENGTH: 4122
<212> TYPE: DNA
<213> ORGANISM: Artificial Sequence
<220> FEATURE:

<223> OTHER INFORMATION: SYNTHESIZED

<400> SEQUENCE: 10

```
atggacaaga agtacagcat cggcctggac atcggcacca actctgtggg ctgggccgtg      60
atcaccgacg actacaaggt gcccagcaag aaattcaagg tgctgggcaa caccgaccgg     120
cacagcatca agaagaacct gatcggcgcc ctgctgttcg gctctggcga aacagccgag     180
gccacccggc tgaagagaac cgccagaaga agatacacca gacggaagaa ccggatctgc     240
tatctgcaag agatcttcag caacgagatg gccaaggtgg acgacagctt cttccacaga     300
ctggaagagt ccttcctggt ggaagaggat aagaagcacg agcggcaccc catcttcggc     360
aacatcgtgg acgaggtggc ctaccacgag aagtacccca ccatctacca cctgagaaag     420
aagctggccg acagcaccga caaggccgac ctgagactga tctacctggc cctggcccac     480
atgatcaagt tccggggcca cttcctgatc gagggcgacc tgaaccccga caacagcgac     540
gtggacaagc tgttcatcca gctggtgcag atctacaatc agctgttcga ggaaaacccc     600
atcaacgcca gcagagtgga cgccaaggcc atcctgagcg ccagactgag caagagcaga     660
cggctggaaa atctgatcgc ccagctgccc ggcgagaagc ggaatggcct gttcggcaac     720
ctgattgccc tgagcctggg cctgaccccc aacttcaaga gcaacttcga cctggccgag     780
gatgccaaac tgcagctgag caaggacacc tacgacgacg acctggacaa cctgctggcc     840
cagatcggcg accagtacgc cgacctgttt ctggccgcca gaaacctgtc cgacgccatc     900
ctgctgagcg acatcctgag agtgaacagc gagatcacca aggcccccct gtccgcctct     960
atgatcaaga gatacgacga gcaccaccag gacctgaccc tgctgaaagc tctcgtgcgg    1020
cagcagctgc ctgagaagta caaagagatt ttcttcgacc agagcaagaa cggctacgcc    1080
ggctacatcg atggcggagc cagccaggaa gagttctaca agttcatcaa gcccatcctg    1140
gaaaagatgg acggcaccga ggaactgctc gtgaagctga acagagagga cctgctgcgg    1200
aagcagcgga ccttcgacaa cggcagcatc ccccaccaga tccacctggg agagctgcac    1260
gccattctgc ggcggcagga agatttttac ccattcctga aggacaaccg ggaaaagatc    1320
gagaagatcc tgacctttag aatcccctac tacgtgggcc ctctggccag gggaaacagc    1380
agattcgcct ggatgaccag aaagagcgag gaaaccatca cccccctgga acttcgaggaa    1440
gtggtggaca agggcgccag cgcccagagc ttcatcgagc ggatgaccaa cttcgataag    1500
aacctgccca acgagaaggt gctgcccaag cacagcctgc tgtacgagta cttcaccgtg    1560
tacaacgagc tgaccaaagt gaaatacgtg accgagggaa tgcggaagcc cgccttttcg    1620
agcggcgagc agaaaaaggc catcgtggac ctgctgttca gaccaaccg gaaagtgacc    1680
gtgaagcagc tgaaagagga ctacttcaag aaaatcgagt gcttcgacag cgtggaaatc    1740
agcggcgtgg aagatcggtt caacgcctcc ctgggcgcct atcacgatct gctgaaaatt    1800
atcaaggaca aggacttcct ggacaatgag gaaaacgagg acattctgga agatatcgtg    1860
ctgaccctga cactgtttga ggaccggggc atgatcgagg aacggctgaa aacctatgcc    1920
cacctgttcg acgacaaagt gatgaagcag ctgaagcggc ggagatacac cggctggggc    1980
aggctgagcc ggaagctgat caacggcatc cgggacaagc agtccggcaa gacaatcctg    2040
gatttcctga agtccgacgg cttcgccaac agaaacttca tgcagctgat ccacgacgac    2100
agcctgacct ttaaagagga catccagaaa gcccaggtgt ccggccaggg acactctctg    2160
cacgagcaga tcgccaatct ggccggatcc ccgccattag agagggcat cctgcagaca    2220
gtgaagattg tggacgagct cgtgaaagtg atgggccaca gcccgagaa catcgtgatc    2280
```

```
gaaatggcca gagagaacca gaccacccag aagggacaga agaacagccg cgagagaatg    2340
aagcggatcg aagagggcat caaagagctg ggcagccaga tcctgaaaga acaccccgtg    2400
gaaaacaccc agctgcagaa cgagaagctg tacctgtact acctgcagaa tgggcgggat    2460
atgtacgtgg accaggaact ggacatcaac cggctgtccg actacgatgt ggaccacatt    2520
gtgccccagt ccttcatcaa ggacgactcc atcgataaca aagtgctgac tcggagcgac    2580
aagaaccggg gcaagagcga caacgtgccc tccgaagagg tcgtgaagaa gatgaagaac    2640
tactggcgcc agctgctgaa tgccaagctg attacccaga ggaagttcga caatctgacc    2700
aaggccgaga gaggcggcct gagcgaactg gataaggccg gcttcattaa gcggcagctg    2760
gtggaaaccc ggcagatcac aaagcacgtg gcacagatcc tggactcccg gatgaacact    2820
aagtacgacg agaacgacaa actgatccgg gaagtgaaag tgatcaccct gaagtccaag    2880
ctggtgtccg acttcagaaa ggatttccag ttttacaaag tgcgcgagat caacaactac    2940
caccacgccc acgacgccta cctgaacgcc gtcgtgggaa ccgccctgat caaaaagtac    3000
cctaagctgg aaagcgagtt cgtgtacggc gattacaagg tgtacgacgt gcggaagatg    3060
atcgccaaga gcgagcagga aatcggcaag gctaccgcca agtacttctt ctacagcaac    3120
atcatgaact tttcaagac cgagatcaca ctggccaacg gcgagatcag aaagcggcct    3180
ctgatcgaga caaacggcga aaccgggag atcgtgtggg ataagggccg ggattttgcc    3240
acagtgcgga aagtgctgtc catgccccaa gtgaatatcg tgaaaaagac cgaggtgcag    3300
accggcggct tcagcaaaga gtctatcctg cccaagagga actccgacaa gctgatcgcc    3360
agaaagaagg attgggaccc taagaagtac ggcggctttg acagccccac cgtggcctac    3420
tctgtgctgg tggtggccaa agtggaaaag ggcaagtcca agaaactgaa gagtgtgaaa    3480
gagctgctgg ggatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggccggaag cggatgctgg cttctgccgg cgaactgcag    3660
aagggaaacg agctggccct gcccctccaaa tatgtgaact tcctgtacct ggccagccac    3720
tatgagaagc tgaagggctc ccccgaggat aatgagcaga acagctgtt tgtggaacag    3780 cacaagcact acctggacga gatcatcgag cagattagcg agttctccaa gcgcgtgatc    3840
ctggccgatg ccaacctgga caaggtgctg agcgcctaca acaagcaccg ggataagccc    3900
atcagagagc aggccgagaa tatcatccac ctgtttaccc tgaccaacct gggagcccct    3960
gccgccttca gtactttga caccaccatc gaccggaaga ggtacaccag caccaaagag    4020
gtgctggacg ccaccctgat ccaccagagc atcaccggcc tgtacgagac acggatcgac    4080
ctgtctcagc tgggaggcga ccccaagaaa aagcgcaaag tg                      4122
```

<210> SEQ ID NO 11
<211> LENGTH: 4764
<212> TYPE: DNA
<213> ORGANISM: Homo sapiens

<400> SEQUENCE: 11

```
gcgggcgggc ggtgcgatgt ccggagagga tggcccggcg gctggcccgg gggcggcggc      60
ggcggctgcc cggagcggc gacgggagca gctgcggcag tgggggcgc gggcgggcgc     120 cgagcctggc cccggagagc gccgcgcccg caccgtccgc ttcgagcgcg ccgccgagtt     180
cctggcggcc tgtgcgggcg cgacctgga cgaggcgcgt ctgatgctgc gcgccgccga     240
```

-continued

```
ccctggcccc ggcgccgagc tcgaccccgc cgcgccgccg cccgcccgcg ccgtgctgga      300
ctccaccaac gccgacggta tcagcgccct gcaccaggtc agcgccccccc gcccggcgtc      360
tcccggggcc aggtccaccc tctgctgcgc cacctggggc atcctccttc cccgttgcca      420
gtctcgatcc gccccgtcgt tcctggccct gggctttgcc accctatgct gacaccccgt      480
cccagtcccc cttaccattc cccttcgacc accccacttc cgaattggag ccgcttcaac      540
tggccctggg cttagccact ctgtgctgac cactctgccc caggcctcct taccattccc      600
cttcgaccta ctctcttccg cattggagtc gctttaactg gccctggctt tggcagcctg      660
tgctgaccca tgcagtcctc cttaccatcc ctccctcgac ttcccctctt ccgatgttga      720
gcccctccag ccggtcctgg actttgtctc cttccctgcc ctgccctctc ctgaacctga      780
gccagctccc atagctcagt ctggtctatc tgcctggccc tggccattgt cactttgcgc      840
tgccctcctc tcgccccga gtgccttgc tgtgccgccg aactctgcc ctctaacgct      900
gccgtctctc tcctgagtcc ggaccacttt gagctctact ggcttctgcg ccgcctctgg      960
cccactgttt cccttccca ggcaggtcct gctttctctg acctgcattc tctccctgg     1020
gcctgtgccg ctttctgtct gcagcttgtg gcctgggtca cctctacggc tggcccagat     1080
ccttccctgc cgcctcctc aggttccgtc ttcctccact ccctcttccc cttgctctct     1140
gctgtgttgc tgcccaagga tgctctttcc ggagcacttc cttctcggcg ctgcaccacg     1200
tgatgtcctc tgagcggatc ctcccgtgt ctgggtcctc tccgggcatc tctcctccct     1260
cacccaaccc catgccgtct tcactcgctg ggttcccttt ccttctcct tctggggcct     1320
gtgccatctc tcgtttctta ggatggcctt ctccgacgga tgtctcccct tgcgtcccgcc     1380
tccccttctt gtaggcctgc atcatcaccg ttttctgga caaccccaaa gtacccgtc      1440
tccctggctt tagccaccct ccatcctct tgctttcttt gcctggacac cccgttctcc     1500
tgtggattcg ggtcacctct cactcctttc atttgggcag ctccctacc cccttacct      1560
ctctagtctg tgctagctct tccagccccc tgtcatggca tcttccaggg gtccgagagc     1620
tcagctagtc ttcttcctcc aacccgggcc ctatgtcca cttcaggaca gcatgtttgc     1680
tgcctccagg gatcctgtgt ccccgagctg ggaccacctt atattcccag ggccggttaa     1740
tgtggctctg gttctgggta ctttttatctg tccccctccac cccacagtgg ggccactagg     1800
gacaggattg gtgacagaaa agccccatcc ttaggcctcc tccttcctag tctcctgata     1860
ttgggtctaa cccccacctc ctgttaggca gattccttat ctggtgacac accccatttt     1920
cctggagcca tctctctcct tgccagaacc tctaaggttt gcttacgatg gagccagaga     1980
ggatcctggg agggagagct tggcagggg tgggagggaa gggggggatg cgtgacctgc     2040
ccggttctca gtgccaccc tgcgctaccc tctcccagaa cctgagctgc tctgacgcgg     2100
ccgtctggtg cgtttcactg atcctggtgc tgcagcttcc ttacacttcc caagaggaga     2160
agcagtttgg aaaacaaaa tcagaataag ttggtcctga gttctaactt tggctcttca     2220
cctttctagt ccccaattta tattgttcct ccgtgcgtca gttttacctg tgagataagg     2280
ccagtagcca gccccgtcct ggcagggctg tggtgaggag ggggtgtcc gtgtggaaaa     2340
ctcccttttgt gagaatggtg cgtcctaggt gttcaccagg tcgtggccgc ctctactccc     2400
tttctctttc tccatccttc tttccttaaa gagtccccag tgctatctgg gacatattcc     2460
tccgcccaga gcagggtccc gcttcctaa gccctgctc tgggcttctg ggtttgagtc     2520
cttggcaagc ccaggagagg cgctcaggct tccctgtccc ccttcctcgt ccaccatctc     2580
atgcccctgg ctctcctgcc ccttccctac aggggttcct ggctctgctc ttcagactga     2640
```

-continued

```
gccccgttcc cctgcatccc cgttccctg catccccctt ccctgcatc cccagaggc    2700 cccaggccac ctacttggcc tggacccac gagaggccac cccagccctg tctaccaggc   2760
tgccttttgg gtggattctc ctccaactgt ggggtgactg cttggcaaac tcactcttcg   2820
gggtatccca ggaggcctgg agcattgggg tgggctgggg ttcagagagg agggattccc   2880
ttctcaggtt acgtggccaa gaagcagggg agctgggttt gggtcaggtc tgggtgtggg   2940
gtgaccagct tatgctgttt gcccaggaca gcctagtttt agcactgaaa ccctcagtcc   3000
taggaaaaca gggatggttg gtcactgtct ctgggtgact cttgattccc ggccagtttc   3060
tccacctggg gctgtgtttc tcgtcctgca tccttctcca gcaggtccc caagcatcgc    3120 cccctgctg tggctgttcc caagttctta gggtacccca cgtgggttta tcaaccactt    3180
ggtgaggctg gtaccctgcc cccattcctg cacccaatt gccttagtgg ctaggggtt     3240 gggggctaga gtaggagggg ctggagccag gattcttagg gctgaacaga aagagctgg    3300 gggcctgggc tcctgggttt gagagaggag gggctgggc ctggactcct gggtccgagg    3360
gaggaggggc tggggcctgg actcctgggt ctgagggtgg agggactggg ggcctggact   3420
cctgggtccg agggaggagg ggctggggcc tggactcgtg gtctgagggg aggaggggct   3480
gggggcctgg acttctgggt cttagggagg cggggctggg cctggacccc tgggtctgaa   3540
tggggagagg ctgggggcct ggactccttc atctgagggc ggaagggctg gggcctggcc   3600
tcctgggttg aatggggagg ggttgggcct ggactctgga gtccctggtg cccaggcctc   3660
aggcatcttt cacagggatg cctgtactgg gcaggtcctt gaaagggaaa ggcccattgc   3720
tctccttgcc cccctcccct atcgccatga caactgggtg gaaataaacg agccgagttc   3780
atcccgttcc cagggcacgt gcggcccctt cacagcccga gtttccatga cctcatgctc   3840
ttggccctcg tagctccctc ccgcctcctc cagatgggca gctttggaga ggtgagggac   3900 ttgggggta atttatcccg tggatctagg agtttagctt cactccttcc tcagctccag   3960
ttcaggtccc ggagcccacc cagtgtccac aaggcctggg gcaagtccct cctccgaccc   4020
cctggacttc ggcttttgtc cccccaagtt ttggaccct aagggaagaa tgagaaacgg     4080
tggcccgtgt cagcccctgg ctgcagggcc ccgtgcagag ggggcctcag tgaactggag   4140
tgtgacagcc tggggcccag gcacacaggt gtgcagctgt ctcacccctc tgggagtccc   4200
gcccaggccc ctgagtctgt cccagcacag ggtggccttc ctccaccctg catagccctg   4260
ggcccacggc ttcgttcctg cagagtatct gctggggtgg tttccgagct tgacccttgg   4320
aaggacctgc tgggtttaa ggcaggaggg gctggggggcc aggactcctg gctctgaagg   4380
aggaggggct ggaacctctt ccctagtctg agcactggaa gcgccacctg tgggtggtga   4440
cgggggtttt gccgtgtcta acaggtacca tgtgggttc ccgcacccag atgagaagcc    4500
ccctcccttc cccgttcact tcctgtttgc agatagccag gagtcctttc gtggtttcca   4560
ctgagcactg aaggcctggc cggcctgacc actgggcaac caggcgtatc ttaaacagcc   4620
agtggccaga ggctgttggg tcattttccc cactgtccta gcaccgtgtc cctggatctg   4680
ttttcgtggc tccctctgga gtcccgactt gctgggacac cgtggctggg gtaggtgcgg   4740
ctgacggctg tttcccaccc ccag                                          4764
```

<210> SEQ ID NO 12
<211> LENGTH: 42
<212> TYPE: RNA
<213> ORGANISM: Artificial Sequence
<220> FEATURE:

<223> OTHER INFORMATION: SYNTHESIZED

<400> SEQUENCE: 12
accccacagu ggggccacua guuuuagagc uaugcuguuu ug                42

<210> SEQ ID NO 13
<211> LENGTH: 86
<212> TYPE: RNA
<213> ORGANISM: Artificial Sequence
<220> FEATURE:
<223> OTHER INFORMATION: SYNTHESIZED

<400> SEQUENCE: 13
ggaaccauuc aaaacagcau agcaaguuaa aauaaggcua guccguuauc aacuugaaaa    60
aguggcaccg agucggugcu uuuuuu                                        86

<210> SEQ ID NO 14
<211> LENGTH: 62
<212> TYPE: RNA
<213> ORGANISM: Artificial Sequence
<220> FEATURE:
<223> OTHER INFORMATION: SYNTHESIZED

<400> SEQUENCE: 14
accccacagu ggggccacua guuuuagagc uagaaauagc aaguuaaaau aaggcuaguc    60
cg                                                                  62

<210> SEQ ID NO 15
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 15
ctgacctctt ctcttcctcc cacag                                         25

<210> SEQ ID NO 16
<211> LENGTH: 1009
<212> TYPE: DNA
<213> ORGANISM: Artificial Sequence
<220> FEATURE:
<223> OTHER INFORMATION: SYNTHESIZED

<400> SEQUENCE: 16
gccaccatgg actacaaaga cgatgacgac aaggtcgact ctagagctgc agagagcgac    60
gagagcggcc tgcccgccat ggagatcgag tgccgcatca ccggcaccct gaacggcgtg   120
gagttcgagc tggtgggcgg cggagagggc accccgagc agggccgcat gaccaacaag   180
atgaagagca ccaaaggcgc cctgaccttc agcccctacc tgctgagcca cgtgatgggc   240
tacggcttct accacttcgg cacctacccc agcggctacg agaacccctt cctgcacgcc   300
atcaacaacg gcggctacac caacacccgc atcgagaagt acgaggacgg cggcgtgctg   360
cacgtgagct tcagctaccg ctacgaggcc ggccgcgtga tcggcgactt caaggtgatg   420
ggcaccggct cccccgagga cagcgtgatc ttcaccgaca agatcgtccg cagcaacgcc   480
accgtggagc acctgcaccc catgggcgat aacgatctgg atggcagctt cacccgcacc   540
ttcagcctgc gcgacggcgg ctactacagc tccgtggtgg acagccacat gcacttcaag   600
agcgccatcc accccagcat cctgcagaac ggggccccca tgttcgcctt ccgccgcgtg   660
gaggaggatc acagcaacac cgagctgggc atcgtggagt accagcacgc cttcaagacc   720

```
ccggatgcag atgccggtga agaatgaaga tctctgtgcc ttctagttgc cagccatctg    780
ttgtttgccc ctcccccgtg ccttccttga ccctggaagg tgccactccc actgtccttt    840
cctaataaaa tgaggaaatt gcatcgcatt gtctgagtag gtgtcattct attctggggg    900
gtggggtggg gcaggacagc aaggggagg attgggaaga caatagcagg catgctgggg    960
atgcggtggg ctctatggac tcgaggttta aacgtcgacg cggccgcgt              1009
```

<210> SEQ ID NO 17
<211> LENGTH: 355
<212> TYPE: PRT
<213> ORGANISM: Artificial Sequence
<220> FEATURE:
<223> OTHER INFORMATION: SYNTHESIZED

<400> SEQUENCE: 17

```
Met Ser Gly Glu Asp Gly Pro Ala Ala Gly Pro Ala Ala Ala Ala
1               5                   10                  15

Ala Ala Arg Glu Arg Arg Glu Gln Leu Arg Gln Trp Gly Ala Arg
                20                  25                  30

Ala Gly Ala Glu Pro Gly Pro Gly Glu Arg Arg Ala Arg Thr Val Arg
            35                  40                  45

Phe Glu Arg Ala Ala Glu Phe Leu Ala Ala Cys Ala Gly Gly Asp Leu
50                  55                  60

Asp Glu Ala Arg Leu Met Leu Arg Ala Ala Asp Pro Gly Pro Gly Ala
65                  70                  75                  80

Glu Leu Asp Pro Ala Ala Pro Pro Ala Arg Ala Val Leu Asp Ser
                85                  90                  95

Thr Asn Ala Asp Gly Ile Ser Ala Leu His Gln Ala Thr Met Asp Tyr
            100                 105                 110

Lys Asp Asp Asp Asp Lys Val Asp Ser Arg Ala Ala Glu Ser Asp Glu
        115                 120                 125

Ser Gly Leu Pro Ala Met Glu Ile Glu Cys Arg Ile Thr Gly Thr Leu
    130                 135                 140

Asn Gly Val Glu Phe Glu Leu Val Gly Gly Gly Glu Gly Thr Pro Glu
145                 150                 155                 160

Gln Gly Arg Met Thr Asn Lys Met Lys Ser Thr Lys Gly Ala Leu Thr
                165                 170                 175

Phe Ser Pro Tyr Leu Leu Ser His Val Met Gly Tyr Gly Phe Tyr His
            180                 185                 190

Phe Gly Thr Tyr Pro Ser Gly Tyr Glu Asn Pro Phe Leu His Ala Ile
        195                 200                 205

Asn Asn Gly Gly Tyr Thr Asn Thr Arg Ile Glu Lys Tyr Glu Asp Gly
    210                 215                 220

Gly Val Leu His Val Ser Phe Ser Tyr Arg Tyr Glu Ala Gly Arg Val
225                 230                 235                 240

Ile Gly Asp Phe Lys Val Met Gly Thr Gly Phe Pro Glu Asp Ser Val
                245                 250                 255

Ile Phe Thr Asp Lys Ile Val Arg Ser Asn Ala Thr Val Glu His Leu
            260                 265                 270

His Pro Met Gly Asp Asn Asp Leu Asp Gly Ser Phe Thr Arg Thr Phe
        275                 280                 285

Ser Leu Arg Asp Gly Gly Tyr Tyr Ser Ser Val Val Asp Ser His Met
    290                 295                 300

His Phe Lys Ser Ala Ile His Pro Ser Ile Leu Gln Asn Gly Gly Pro
```

```
            305                 310                 315                 320
Met Phe Ala Phe Arg Arg Val Glu Glu Asp His Ser Asn Thr Glu Leu
            325                 330                 335
Gly Ile Val Glu Tyr Gln His Ala Phe Lys Thr Pro Asp Ala Asp Ala
            340                 345                 350
Gly Glu Glu
        355

<210> SEQ ID NO 18
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 18
ccactctgtg ctgaccactc t                                              21

<210> SEQ ID NO 19
<211> LENGTH: 17
<212> TYPE: DNA
<213> ORGANISM: Artificial Sequence
<220> FEATURE:
<223> OTHER INFORMATION: SYNTHESIZED

<400> SEQUENCE: 19
gcggcactcg atctcca                                                   17

<210> SEQ ID NO 20
<211> LENGTH: 711
<212> TYPE: DNA
<213> ORGANISM: Mus musculus

<400> SEQUENCE: 20
gagcggctgc ggggcgggtg caagcacgtt tccgacttga gttgcctcaa gaggggcgtg    60
ctgagccaga cctccatcgc gcactccggg gagtggaggg aaggagcgag ggctcagttg   120
ggctgttttg gaggcaggaa gcacttgctc tcccaaagtc gctctgagtt gttatcagta   180
agggagctgc agtggagtag gcggggagaa ggccgcaccc ttctccggag ggggaggggg   240
agtgttgcaa tacctttctg ggagttctct gctgcctcct ggcttctgag accgccctg    300 ggcctgggag aatcccttcc ccctcttccc tcgtgatctg caactccagt ctttctagaa   360
gatgggcggg agtcttctgg gcaggcttaa aggctaacct ggtgtgtggg cgttgtcctg   420
caggggaatt gaacaggtgt aaaattggag ggacaagact tcccacagat tttcggtttt   480
gtcgggaagt tttttaatag gggcaaataa ggaaatggg aggataggta gtcatctggg    540
gttttatgca gcaaaactac aggttattat tgcttgtgat ccgcctcgga gtattttcca   600
tcgaggtaga ttaaagacat gctcacccga gttttatact ctcctgcttg agatccttac   660
tacagtatga aattacagtg tcgcgagtta gactatgtaa gcagaatttt a            711

<210> SEQ ID NO 21
<211> LENGTH: 42
<212> TYPE: RNA
<213> ORGANISM: Artificial Sequence
<220> FEATURE:
<223> OTHER INFORMATION: SYNTHESIZED

<400> SEQUENCE: 21
cuccagucuu ucuagaagau guuuuagagc uaugcuguuu ug                       42
```

```
<210> SEQ ID NO 22
<211> LENGTH: 42
<212> TYPE: RNA
<213> ORGANISM: Artificial Sequence
<220> FEATURE:
<223> OTHER INFORMATION: SYNTHESIZED

<400> SEQUENCE: 22
ugaacaggug uaaaauugga guuuuagagc uaugcuguuu ug          42

<210> SEQ ID NO 23
<211> LENGTH: 42
<212> TYPE: RNA
<213> ORGANISM: Artificial Sequence
<220> FEATURE:
<223> OTHER INFORMATION: SYNTHESIZED

<400> SEQUENCE: 23
ugucgggaag uuuuuuaaua guuuuagagc uaugcuguuu ug          42

<210> SEQ ID NO 24
<211> LENGTH: 642
<212> TYPE: DNA
<213> ORGANISM: Rattus rattus

<400> SEQUENCE: 24
gggattcctc cttgagttgt ggcactgagg aacgtgctga acaagaccta cattgcactc     60
cagggagtgg atgaaggagt tggggctcag tcgggttgta ttggagacaa gaagcacttg    120
ctctccaaaa gtcggtttga gttatcatta agggagctgc agtggagtag gcggagaaaa    180
ggccgcaccc ttctcaggac gggggagggg agtgttgcaa tacctttctg ggagttctct    240
gctgcctcct gtcttctgag gaccgccctg ggcctggaag attcccttcc cccttcttcc    300
ctcgtgatct gcaactggag tctttctgga agataggcgg gagtcttctg ggcaggctta    360
aaggctaacc tggtgcgtgg ggcgttgtcc tgcagaggaa ttgaacaggt gtaaaattgg    420
aggggcaaga cttcccacag attttcgatt gtgttgttaa gtattgtaat agggggcaaat    480 aagggaaata gactaggcac tcacctgggg ttttatgcag caaaactaca ggttattatt    540
gcttgtgatc cgccctggag aattttttcac cgaggtagat tgaagacatg cccacccaaa    600
ttttaatatt cttccacttg cgatccttgc tacagtatga aa                       642

<210> SEQ ID NO 25
<211> LENGTH: 42
<212> TYPE: RNA
<213> ORGANISM: Artificial Sequence
<220> FEATURE:
<223> OTHER INFORMATION: SYNTHESIZED

<400> SEQUENCE: 25
agggggaagg gaaucuucca guuuuagagc uaugcuguuu ug          42

<210> SEQ ID NO 26
<211> LENGTH: 42
<212> TYPE: RNA
<213> ORGANISM: Artificial Sequence
<220> FEATURE:
<223> OTHER INFORMATION: SYNTHESIZED

<400> SEQUENCE: 26
ucugcaacug gagucuuucu guuuuagagc uaugcuguuu ug          42
```

```
<210> SEQ ID NO 27
<211> LENGTH: 42
<212> TYPE: RNA
<213> ORGANISM: Artificial Sequence
<220> FEATURE:
<223> OTHER INFORMATION: SYNTHESIZED

<400> SEQUENCE: 27
aggcgggagu cuucugggca guuuuagagc uaugcuguuu ug            42
```